United States Patent
Zhu et al.

(10) Patent No.: US 9,315,779 B2
(45) Date of Patent: Apr. 19, 2016

(54) REPROGRAMMING CELLS

(71) Applicant: The Scripps Research Institute, La Jolla, CA (US)

(72) Inventors: Saiyong Zhu, San Diego, CA (US); Sheng Ding, Orinda, CA (US)

(73) Assignee: The Scripps Research Institute, La Jolla, CA (US)

(*) Notice: Subject to any disclaimer, the term of this patent is extended or adjusted under 35 U.S.C. 154(b) by 140 days.

(21) Appl. No.: 13/896,259

(22) Filed: May 16, 2013

(65) Prior Publication Data

US 2013/0323833 A1 Dec. 5, 2013

Related U.S. Application Data

(63) Continuation of application No. 13/637,334, filed as application No. PCT/US2011/030598 on Mar. 30, 2011, now abandoned.

(60) Provisional application No. 61/319,494, filed on Mar. 31, 2010, provisional application No. 61/406,892, filed on Oct. 26, 2010, provisional application No. 61/393,724, filed on Oct. 15, 2010.

(51) Int. Cl.
*C12N 5/074* (2010.01)

(52) U.S. Cl.
CPC ........ *C12N 5/0696* (2013.01); *C12N 2501/065* (2013.01); *C12N 2501/15* (2013.01); *C12N 2501/41* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2506/094* (2013.01); *C12N 2506/28* (2013.01)

(58) Field of Classification Search
CPC ................ C12N 5/074; C12N 5/0696; C12N 2501/065; C12N 2501/727; C12N 2501/41; C12N 2506/28; C12N 2501/602; C12N 2501/603; C12N 2506/094; C12N 2501/15
See application file for complete search history.

(56) References Cited

U.S. PATENT DOCUMENTS

| | | | |
|---|---|---|---|
| 5,824,837 A | 10/1998 | Chen et al. | |
| 5,843,780 A | 12/1998 | Thomson | |
| 6,200,806 B1 | 3/2001 | Thomson | |
| 7,029,913 B2 | 4/2006 | Thomson | |
| 7,265,138 B2 | 9/2007 | Doherty et al. | |
| 8,298,825 B1 | 10/2012 | Hochedlinger et al. | |
| 8,546,140 B2 | 10/2013 | Mack et al. | |
| 8,603,818 B1 | 12/2013 | Hochedlinger et al. | |
| 8,906,677 B2 | 12/2014 | Li et al. | |
| 2002/0142457 A1 | 10/2002 | Umezawa et al. | |
| 2004/0157324 A1 | 8/2004 | Spradling et al. | |
| 2006/0182724 A1 | 8/2006 | Riordan | |
| 2007/0032447 A1 | 2/2007 | Eilertsen | |
| 2007/0128719 A1 | 6/2007 | Tseng et al. | |
| 2007/0134215 A1 | 6/2007 | Fukuda et al. | |
| 2007/0141703 A1 | 6/2007 | Stanley et al. | |
| 2007/0161107 A1 | 7/2007 | Mummery et al. | |
| 2007/0172946 A1 | 7/2007 | Smith et al. | |
| 2007/0196919 A1 | 8/2007 | Reh et al. | |
| 2007/0254359 A1 | 11/2007 | Rezania et al. | |
| 2007/0259423 A1 | 11/2007 | Odorico et al. | |
| 2007/0264709 A1 | 11/2007 | Smith et al. | |
| 2007/0269412 A1 | 11/2007 | Kopyov | |
| 2007/0281355 A1 | 12/2007 | Dalton et al. | |
| 2008/0066197 A1 | 3/2008 | Ying et al. | |
| 2008/0242594 A1 | 10/2008 | McKay et al. | |
| 2008/0268533 A1 | 10/2008 | Dalton et al. | |
| 2009/0068742 A1 | 3/2009 | Yamanaka | |
| 2009/0117439 A1 | 5/2009 | Fujinami et al. | |
| 2009/0203690 A1 | 8/2009 | Akritopoulou-Zanze et al. | |
| 2009/0227032 A1 | 9/2009 | Yamanaka et al. | |
| 2010/0233804 A1 | 9/2010 | Zhou et al. | |
| 2010/0267141 A1 | 10/2010 | Shi et al. | |
| 2011/0033931 A1 | 2/2011 | Schwartz et al. | |
| 2011/0039332 A1 | 2/2011 | Sakurada et al. | |
| 2012/0122212 A1 | 5/2012 | Grskovic et al. | |
| 2012/0129172 A1 | 5/2012 | Okano et al. | |
| 2012/0196360 A1 | 8/2012 | Okita et al. | |
| 2013/0323833 A1 | 12/2013 | Zhu et al. | |
| 2015/0079675 A1 | 3/2015 | Li et al. | |

FOREIGN PATENT DOCUMENTS

| | | |
|---|---|---|
| CN | 101356270 | 1/2009 |
| EP | 1970446 A1 | 9/2008 |
| GB | 2 436 737 | 10/2007 |
| GB | 2 450 603 A | 12/2008 |
| JP | 2007/508026 | 4/2007 |
| JP | 2008/307007 | 12/2008 |
| JP | 2010/529851 | 9/2010 |
| WO | 03/095628 A2 | 11/2003 |
| WO | 2009/032456 A1 | 3/2006 |
| WO | 2007/016566 A2 | 2/2007 |

(Continued)

OTHER PUBLICATIONS

Engel et al., The EMBO Journal, 25: 5469-5480, 2006.*
Wang et al., Cell, 86: 35-444, 1996.*
Zhao et al., The Journal of Antibiotics, 52(12): 1086-1094, 1999.*
Stadtfeld. Science, 322: 945-949, 2008.*
Okita. Science, 322: 949-953, 2008.*
Gonzalez. PNAS, 106(22): 8918-8922, 2009.*
Pesce et al., Mechanisms of Development, 71: 89-98, 1998.*
Egler et al., Clin. Cancer Res., 14(10): 3132-3140, 2008.*
Watanabe et al., Oncogene, 25: 2697-2707, 2006.*

(Continued)

*Primary Examiner* — Thaian N Ton
(74) *Attorney, Agent, or Firm* — Kilpatrick Townsend & Stockton LLP

(57) ABSTRACT

The present invention provides for methods, compositions, and kits for producing an induced pluripotent stem cell from a non-pluripotent mammalian cell using a 3'-phosphoinositide-dependent kinase-1 (PDK1) activator or a compound that promotes glycolytic metabolism as well as other small molecules.

11 Claims, 11 Drawing Sheets

(56) References Cited

FOREIGN PATENT DOCUMENTS

| WO | 2007/069666 | | 6/2007 |
|---|---|---|---|
| WO | 2007/113505 | | 10/2007 |
| WO | 2008/015418 | A2 | 2/2008 |
| WO | 2008/056173 | A2 | 5/2008 |
| WO | 2008/088882 | | 7/2008 |
| WO | 2008/089351 | | 7/2008 |
| WO | 2008/105630 | A1 | 9/2008 |
| WO | 2009/006422 | A1 | 1/2009 |
| WO | 2009/032194 | A1 | 3/2009 |
| WO | 2009/057831 | | 5/2009 |
| WO | 2009/067756 | A1 | 6/2009 |
| WO | 2009/067757 | A1 | 6/2009 |
| WO | 2009/073523 | A2 | 6/2009 |
| WO | 2009/117439 | A1 | 9/2009 |
| WO | 2011/047300 | A1 | 4/2011 |
| WO | 2011/109695 | A1 | 9/2011 |

OTHER PUBLICATIONS

Chen et al., "Self-renewal of embryonic stem cells by a small molecule," PNAS, 103(46):17266-17271, 2006.

Watanabe et al., "A ROCK inhibitor permits survival of dissociated human embryonic stem cells," Nature Biotechnology, 25(6):681-868, 2007.

Condorelli, G. et al., "Cardiomyocytes induce endothelial cells to trans-differentiate into cardiac muscle: Implications for myocardium regeneration," PNAS, vol. 98, No. 19, Sep. 11, 2001, pp. 10733-10738.

Dravida, S. et al., "The transdifferentiation potential of limbal fibroblast-like cells," Developmental Brain Research, vol. 160, No. 2, Dec. 7, 2005, pp. 239-251.

Efe, Jem E. et al., "Conversion of mouse fibroblasts into cardiomyocytes using a direct reprogramming strategy," Nature Cell Biology, vol. 13, No. 3, Mar. 1, 2011, pp. 215-222.

Kaji et al., "Virus free induction of pluripotency and subsequent excision of reprogramming factors," Nature, Apr. 2009, vol. 458(7239), pp. 771-775.

Kim et al., "Pluripotent stem cells induced from adult neural stem cells by reprogramming with two factors," 2008, Nature 454:646-651.

Loh et al., "Generation of induced pluripotent stem cells from human blood," Blood, May 2009, vol. 113(22), pp. 5476-5479.

Takei, Shunsuke et al., "Bone morphogenetic protein-4 promotes induction of cardiomyocytes from human embryonic stem cells in serum-based embryoid body development," AJP Heart and Circulatory Physiology, vol. 296, No. 6, Jun. 2009, pp. H1793-H1803.

Takeuchi, Jun K. et al., "Directed transdifferentiation of mouse mesoderm to heart tissue by defined factors," Nature, vol. 459, No. 7247, Jun. 4, 2009, pp. 708-711.

Frodin et al., "A phosphoserine/threonine-binding pocket in AGC kinases and PDK1 mediates activation by hydrophobic motif phosphorylation," The EMBO Journal, 2002, vol. 21(20), pp. 5396-5407.

Si-Tayeb et al., "Generation of human induced pluripotent stem cells by simple transient transfection of plasmid DNA encoding reprogramming factors," BMC Developmental Biology, 2010, vol. 10, pp. 81.

Woltjen et al., "*piggyBac* transposition reprograms fibroblasts to induced pluripotent stem cells," Nature, 2009, vol. 458, pp. 766-770.

Yu et al., "Human Induced Pluripotent Stem Cells Free of Vector and Transgene Sequences," Science 2009, vol. 324(5928), pp. 797-801.

Yusa et al., "Generation of transgene-free induced pluripotent mouse stem cells by the *piggyBac* transposon," Nature Methods, 2009, vol. 6(5), pp. 363-369.

Zhou et al., "Adenoviral Gene Delivery Can Reprogram Human Fibroblasts to Induced Pluripotent Stem Cells," Stem Cells, 2009, vol. 27, pp. 2667-2674.

Aoi et al., "Generation of Pluripotent Stem Cells from Adult Mouse Liver and Stomach Cells," Sciencexpress, Feb. 2008, DOI 10.1126/science.1154884, 8 pages.

Lin et al., Nat Methods 6:805-808 (2009), Supplemental Information, 7 pages.

Noggle et al., "A Molecular Basis for Human Embryonic Stem Cell Pluripotency," Stem Cell Reviews and Reports, Jan. 2005, vol. 1(2), pp. 1550-8943; DOI: 10.1385/scr:1:2:111.

Stadtfeld et al., "Reprogramming of Pancreatic β Cells into Pluripotent Stem Cells," Curr. Biol., Jun. 2008, vol. 18(12): 890, doi: 10.1016/j.cub.2008.05.010.

Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.

Wenlin et al., "Generation of novel rat and human pluripotent stem cells by reprogramming and chemical approaches," Methods in Molecular Biology, Jan. 2010, vol. 636, pp. 293-300.

Xiong et al., "Histone deacetylase inhibitors DNA methyltransferase-3B messenger RNA stability and down-regulate de novo DNA methyltransferase activity in human endometrial cells," Cancer Res., Apr. 2005, vol. 65(7), pp. 2684-2689.

Zhou et al., "Conversion of Mouse Epiblast Stem Cells to an Earlier Pluripotency State by Small Molecules," Journal of Biological Chemistry, Sep. 2010, vol. 285(39), pp. 29676-29680; DOI: 10.1074/jbc.C110.150599.

Feldman et al., "G9a-mediated irreversible epigenetic inactivation of Oct. 3/4 during early embryogenesis," Nature Cell Biology, 2006, vol. 8(2), pp. 188-194.

Wu et al., "Cellular senescence is an important mechanism of tumor regression upon c-Myc inactivation," PNAS, 2007, vol. 104(32), pp. 13028-13033.

Tighe et al., BMC 8:34 doi///:www.biomedcentral.com/1471-2121/8/34, printout pp. 1-17.

Artyomov et al., PLoS Comput Biol 6, e1000785 (2010).

Brambrink et al., Cell Stem Cell 2, 151-9 (2008).

Christen et al., BMC Biol 8, 5 (2010).

Ernst et al., "gp130-mediated Signal Transduction in Embryonic Stem Cells Involves Activation of Jak and Ras/Mitogen-activated Protein Kinase Pathways," J. Biol. Chem., Nov. 22, 1996, vol. 271, No. 47, pp. 30163-30143.

Graf et al., Nature 462(7273):587-594 (2009).

Han et al., Nat Cell Biol 13(1):66-71 (2011).

Hanna et al., Cell 133, 250-64.

Hanna et al., Nature 462, 595-601 (2009).

Hochedlinger et al., Development 136, 509-23 (2009).

Ieda et al., Cell 142, 375-86 (2010).

Jia et al., Nat Methods 7(3):197-199 (2010).

Kim et al., "Direct reprogramming of mouse fibroblasts to neural progenitors," Proc. Natl. Acad. Sci., USA, May 10, 2011, vol. 108, No. 9, pp. 7838-7843.

Kuzmenkin et al., FASEB J. 23, 4168-80 (2009).

Mikkelsen et al., Nature 454(7200):49-55 (2008).

Okada et al., Biochem Biophys Acta 1800, 956-63 (2010).

Okita et al., Nature 448, 313-317 (2007).

Schenke-Layland et al., Stem Cell 26, 1537-46 (2008).

Silva et al., Cell 138, 722-37 (2009).

Sridharan et al., Cell 136(2):364-377 (2009).

Stadtfeld et al., Cell Stem Cell 2, 230-40 (2008).

Stadtfeld et al., Nat Methods 7, 53-55 (2010).

Szabo et al., Nature 468(7323):521-526 (2010).

Takahashi et al., Nat Protoc 2, 3081-9 (2007).

Vierbuchen et al., "Direct conversion of fibroblasts to functional neurons by defined factors," Nature, Feb. 25, 2010, vol. 463, No. 7284, pp. 1035-1042.

Warren et al., Cell Stem Cell 7(5):618-630 (2010).

Wernig et al., Nat Biotechnol 26, 916-24 (2008).

Yamanaka, S. Cell 126, 663-676 (2006).

Zhou et al., Nature 455(7213):627-632 (2008).

Aasen et al., Nat Biotechnol 26:1276-1284 (2008).

Beaujean et al., Dev. Biol., 2000, vol. 221, pp. 337-354.

Brons et al., Nature, 2007, vol. 448, pp. 191-195.

Chambers et al., Nature, 2007, vol. 450, pp. 1230-1234.

Chen et al., Proc Natl Acad Sci USA, 2007, vol. 104, pp. 10482-10487.

Chou et al., Cell, 2008, vol. 135, pp. 449-461.

(56) References Cited

OTHER PUBLICATIONS

Classen et al., "ROCK inhibition enhances the recovery and growth of cryopreserved human embryonic stem cells and human induced pluripotent stem cells," Molecular Reproduction and Developments, 2009, vol. 76, No. 8, pp. 722-732.
Collas et al., Reporductive BioMedicine Online: 762-770, 2006.
D'Amour et al., Nat Biotechnol, 2005, vol. 23, pp. 1534-1541.
Debs et al., J. Biol. Chem., 1990, vol. 265, pp. 10189-10192.
Demers et al., Cloning Stem Cells, 2007, vol. 9, pp. 512-522.
Dimos et al., Science, 2008, vol. 321, pp. 1218-1221.
Djuric et al., 202, Stem Cell Research and Therapy, 2010, 1:3.
Dvorak et al., Stem Cells, 2005, vol. 23, pp. 1200-1211.
Feng et al, "Molecules that Promote or Enhance Reprogramming of Somatic Cells to Induced Pluripotent Stem Cells," Cell Stem Cell, 2009, 4, 301-12.
Guo et al., Development, 2009, vol. 136, pp. 1063-1069.
Han et al., Curr Stem Cell Res Ther, 2008, vol. 3, pp. 66-74.
Hanna et al, "Treatment of Sickle Cell Anemia Mouse Model with iPS Cells Generated from Autologous Skin," Science, Dec. 21, 2007, vol. 318, pp. 1920-1922.
Hayashi et al., Cell Stem Cell, 2008, vol. 3, pp. 391-401.
Hindie et al., "Structure and allosteric effects of low-molecular-weight activators on the protein kinase PDK1," Nat Chem Biol, Oct. 2009, vol. 5, No. 10, pp. 758-764.
Ho et al., Cancer Res., 2001, vol. 61, pp. 474-77.
Hockedlinger, et al., "Nuclear reprogramming and pluripotency," Nature, Jun. 2006, vol. 441, pp. 1061-1067.
Huangfu et al., "Induction of pluripotent stem cells by defined factors is greatly improved by small-molecule compounds," Nat Biotechnol, Jul. 2008, vol. 26, No. 7, pp. 795-799.
Huangfu et al., "Induction of pluripotent stem cells from primary human fibroblasts with only Oct4 and Sox2," 2008, Nature Biotechnology, 26:11, pp. 1269-1275.
Hudecz et al., Medicinal Research Reviews, 25(6): 679-736, 2005.
Kanatsu-Shinohara et al., Cell, 2004, vol. 119, pp. 1001-1012.
Kim et al., Cell, 2009, vol. 136, pp. 411-419.
Kim et al., Cell Stem Cell, 4(6):472-476, 2009.
Krippl et al., Proc. Natl. Acad. Sci. USA, 1984, vol. 81, pp. 6988-6992.
Kubicek, et al., "Reversal of H3K9me2 by a Small-Molecule Inhibitor for the G9a Histone Methyltransferase," Molecular Cell, Feb. 2007, vol. 25, No. 3, pp. 473-481.
Li et al., "Generation of rat and human induced pluripotent stem cells by combining genetic reprogramming and chemical inhibitors," Cell Stem Cell, 2009, vol. 4, pp. 16-19.
Li et al., Differentiation, 2007, vol. 75, pp. 299-307.
Li et al., "Small molecules that modulate embryonic stem cell fate and somatic cell reprogramming," Trends Pharmacol Sci, Jan. 2010, vol. 31, No. 1, pp. 36-45.
Li et al., Stem Cells 27:2992-3000 (2009).
Lin et al., Nat Methods 6:805-808 (2009).
Lowry et al., Proc Natl Acad Sci USA, 2008, vol. 105, pp. 2883-2888.
Maherali et al., "Directly Reprogrammed Fibroblasts Show Global Epigenetic Remodeling and Widespread Tissue Contribution," Cell Stem Cell, 2007, 1, pp. 55-70.
Maherali et al., "TgfβSignal Inhibition Cooperates in the Induction of iPSCs and Replaces Sox2 and cMyc," Current Biology, 2009, vol. 19, pp. 1718-1723.
Meissner, et al., "Direct reprogramming of genetically unmodified fibroblasts into pluripotent stem cells," Nature Biotechnology, Oct. 2007, vol. 25, No. 10, pp. 1177-1181.
Mi et al., Mol. Ther., 2001, vol. 4, pp. 339-347.
Muller et al., "Upping the Ante: Recent Advances in Direct Reprogramming," Mol. Ther., 2009, vol. 17, pp. 947-953.
Nakagawa et al., Nat Biotechnol, 2008, vol. 26, pp. 101-106.
Okita et al., Science 322:949-953, 2008.
Oliveri et al., Regenerative Medicine, 2(5): 795-816, Sep. 2007.
Pan et al., J. Biol. Chem., 2004, vol. 279, pp. 37013-37020.
Peerani et al., EMBO J., 2007, vol. 26, pp. 4744-4755.
Plath et al., Nature Reviews, 12: 253-265, 2011.
Plews, et al., "Activation of Pluripotency Genes in Human Fibroblast Cells by a Novel mRNA Based Approach," PLoS One, Dec. 2010, vol. 5, No. 12, pp. 1-10.
Roberts et al., "PD98059 Enhanced Insulin, Cytokine, and Growth Factor Activation of Xanthine Oxidoreductase in Epithelial Cells Involves STAT3 and the Glucocoticoid Receptor," Journal of Cellular Biochemistry 2007, 101: 1567-1587.
Ruhnke et al., Stem Cells, 2003, vol. 21, pp. 428-436.
Saha et al., Biophys. J., 2008, vol. 94, pp. 4123-4133.
Sato et al., Dev. Biol., 2003, vol. 260, pp. 404-413.
Schugar et al., Gene Ther, 2008, vol. 15, pp. 126-135.
Schulze et al., Methods Mol Biol, 2006, vol. 329, pp. 45-58.
Sells et al., BioTechniques, 1995, vol. 19, pp. 72-78.
Shi, et al., "A Combined Chemical and Genetic Approach for the Generation of Induced Pluripotent Stem Cells," Cell Stem Cell, Jun. 2008, vol. 2, No. 6, pp. 525-528.
Shi "Induction of Pluripotent Stem Cells from Mouse Embryonic Fibroblasts by Oct4 and Klf4 with Small-Molecule Compounds," Cell Stem Cell, 2008, vol. 3, pp. 568-574.
Shields et al., J. Biol. Chem., 1997, vol. 272, pp. 18504-18507.
Silva et al., PLoS Biology, 6(10): 2237-2247, Oct. 2008.
Singh et al., Stem Cells, 2007, vol. 25, pp. 2534-2542.
Stacey et al., Mol. Cell. Biol., 1987, vol. 7, pp. 523-527.
Stadtfeld et al., Science 322:945-949, 2008.
Sullivan et al., Reproductive BioMed. Online, 16(1): 41-50, Nov. 2008.
Sylvester et al. (Arch Surg. 136:93-99, 2004).
Tada, et al., "Nuclear reprogramming of somatic cells by in vitro hybridization with ES cells," Current Biology, 2001, vol. 11, pp. 1553-1558.
Takahashi, et al., "Induction of Pluripotent Stem Cells from Mouse Embryonic and Adult Fibroblast Cultures by Defined Factors," Cell, Aug. 2006, vol. 126, No. 4, pp. 663-676.
Takahashi et al.; "Induction of Pluripotent Stem Cells from Adult Human Fobroblasts by Defined Factors"; Cell, 2007 131, pp. 861-872.
Taranger et al., "Induction of Dedifferentiation, Genomewide Transcriptional Programming, and Epigenetic Reprogramming by Extracts of Carcinoma and Embryonic Stem Cells," Molecular Biology of the Cell, 2005, vol. 16, pp. 5719-5735.
Tesar et al., Nature, 2007, vol. 448, pp. 196-199.
Tojo, et al., "The ALK-5 inhibitor A-83-01 inhibits Smad signaling and epithelia-to-mesenchymal transition by transforming growth factor-β," Cancer Sci, Nov. 2005, vol. 96, No. 11, pp. 791-800.
Toyooka et al., Development, 2008, vol. 135, pp. 909-918.
Ueda et al., PLoS One 3, 2008, e2800.
Wadia et al., Curr. Opin. Biotechnol., 2002, vol. 13, pp. 52-56.
Wering et al., "c-Myc is Dispensable for Direct Reprogramming of Mouse Fibroblasts," Cell Stem Cell, 2008, 2, 10-12.
Wernig, et al., "In vitro reprogramming of fibroblasts into a pluripotent ES-cell-like state," Nature, Jul. 2007, vol. 448, No. 7151, pp. 318-324.
Yamanaka, "Strategies and New Developments in the Generation of Patient-Specific Pluripotent Stem Cells," Cell Stem Cell, Jul. 2007, vol. 1, pp. 39-49.
Ying et al, Nature, 2008, vol. 453, pp. 519-523.
Ying et al., Cell, 2003, vol. 115, pp. 281-292.
Yu et al., Science, 2007, vol. 318, pp. 1917-1920.
Xu et al., Nature 453, 338-44 (2008).
Xu et al., Nat. Biotechnol, 2002, vol. 20, pp. 1261-1264.
Zhao et al., Cell Death and Differentiation, 2007, vol. 14, pp. 489-499.
Zheng et al., Cancer Res., 2003, vol. 63, pp. 6909-6913.
Zhou, "Hongyan et al.; Generation of Induced Pluripotent Stem Cells Using Recombinant Proteins"; Cell Stem Cell, 4: 381-384 (2009).
Zhu et al., "Reprogramming of human primary somatic cells by OCT4 and chemical compounds," Cell Stem Cell, Dec. 3, 2010, vol. 7, No. 6, pp. 651-655.
Hakelien et al., "Transient alteration of cell fate using a nuclear and cytoplasmic extract of an insulinoma cell line," BBRC, vol. 316, pp. 834-841.
Xu et al., "Revealing a core signaling regulatory mechanism for pluripotent stem cell survival and self-renewal by small molecules," PNAS, 2010, vol. 107(8), pp. 8129-8134.

* cited by examiner

REPROGRAMMING CELLS

CROSS-REFERENCES TO RELATED APPLICATIONS

This application is a continuation of application U.S. Ser. No. 13/637,334, filed Sep. 25, 2012, which is a U.S. National Stage entry under 35 U.S.C. §371 of PCT/US2011/030598, filed Mar. 30, 2011, which claims priority to U.S. Provisional Application No. 61/319,494, filed Mar. 31, 2010, U.S. Provisional Application No. 61/393,724, filed Oct. 15, 2010, and U.S. Provisional Application No. 61/406,892, filed Oct. 26, 2010, the contents of each of which is incorporated by reference in its entirety.

BACKGROUND OF THE INVENTION

Reference to a "Sequence Listing," a Table, or a Computer Program Listing Appendix Submitted as an Ascii Text File The Sequence Listing written in file-40-2.TXT, created on Jul. 1, 2013, 16,384 bytes, machine format IBM-PC. MS-Windows operating system, is hereby incorporated by reference in its entirety for all purposes.

Induced pluripotent stem cell (iPSC) technology, i.e. reprogramming somatic cells into pluripotent cells that closely resemble embryonic stem cells (ESCs) by introduction of defined factors, holds great potential in biomedical research and regenerative medicine (Takahashi, K., and Yamanaka, S., Cell 126, 663-676 (2006); Takahashi et al., Cell 131, 861-872 (2007); Yu et al., Science 318, 1917-1920 (2007); Zhou et al., Cell Stem Cell 4, 381-384 (2009); Kim et al., Cell Stem Cell 4, 472-476 (2009); Maherali, N., and Hochedlinger, K., Cell Stem Cell 3, 595-605 (2009a); Daley et al., Cell Stem Cell 4, 200-201 (2009)). Various strategies have been developed to generate iPSCs with less or no exogenous genetic manipulations, which represent a major hurdle for iPSC applications (Yamanaka et al., 2009; Saha, K., Jaenisch, R., Cell Stem Cell 5, 584-595 (2009)). Toward an ultimate goal of generating iPSCs with a defined small molecule cocktail that would offer significant advantages over genetic manipulations or more difficult-to-manufacture/use biologics, substantial efforts have been made in identifying chemical compounds that can functionally replace exogenous reprogramming transcription factors (TFs) and/or enhance reprogramming efficiency and kinetics (Shi et al., Cell Stem Cell 2, 525-528 (2008a); Shi et al., Cell Stem Cell 3, 568-574 (2008b); Huangfu et al., Nat Biotechnol 26, 795-797 (2008a); Huangfu et al., Nat Biotechnol 26, 1269-1275 (2008b); Silva et al., Plos Bio 6, e253. doi: 10.1371/journal.pbio.0060253 (2008); Lyssiotis et al., PNAS 106, 8912-8917 (2009); Ichida et al., Cell Stem Cell 5, 491-503 (2009); Maherali, N., Hochedlinger, K., Curr Biol 19, 1718-1723 (2009b); Esteban et al., Cell Stem Cell 6, 71-79 (2010); Feng et al., Cell Stem Cell 4, 301-312 (2009)). However, further reducing the number of exogenous TFs has been extraordinarily challenging as (1) most reprogramming enabling or enhancing conditions (e.g., exploiting a specific cell type or using small molecules) are context dependent, i.e., such specific conditions (e.g., a reprogramming small molecule) typically would be much less effective or even harmful in a different cell type with different exogenous factors and used in a different window of treatment; and (2) high throughput screening is technically challenging when the reprogramming efficiency and speed further decrease exponentially due to fewer exogenous TFs used. To date, only neural stem cells (NSCs) that endogenously express Sox2 and cMyc at a high level were shown to be reprogrammed to iPSCs by exogenous expression of only Oct4 (Kim et al., Cell 136, 411-419 (2009a); Kim et al., Nature 461, 643-649 (2009b)). However, human fetal NSCs are rare and practically difficult to obtain (Nunes et al., Nat Med 9, 439-447 (2003)). Consequently, it would be beneficial to develop chemical reprogramming conditions applicable to other more accessible and abundant somatic cells.

BRIEF SUMMARY OF THE INVENTION

The present invention provides for a method of inducing a non-pluripotent mammalian cell into an induced pluripotent stem cell. In some embodiments, the method comprises contacting the non-pluripotent cell with a 3'-phosphoinositide-dependent kinase-1 (PDK1) activator under conditions sufficient to induce the cell to become a pluripotent stem cell. In some embodiments, the PDK1 activator is an allosteric PDK1 activator, e.g., (Z)-5-(4-Chlorophenyl)-3-phenylpent-2-enoic acid ("PS48"), (Z)-5-(4-Bromo-2-fluorophenyl)-3-phenylpent-2-enoic acid ("PS08"), 2-(3-(4-Chlorophenyl)-3-oxo-1-phenylpropylthio)acetic acid, (Z)-5-(Napthalen-2-yl)-3-phenylpent-2-enoic acid ("12Z"), or (Z)-5-(1H-Indol-3-yl)-3-phenylpent-2-enoic acid ("13Z").

In some embodiments, the method further comprises contacting the non-pluripotent cell with a TGFβ receptor/ALK5 inhibitor, e.g., A-83-01. In some embodiments, the method further comprises contacting the non-pluripotent cell with a MEK inhibitor, e.g., PD0325901. In some embodiments, the method further comprises contacting the non-pluripotent cell with a histone deacetylase (HDAC) inhibitor, e.g., sodium butyrate (NaB), or valproic acid (VPA).

In some embodiments, the method comprises contacting the non-pluripotent cell with a 3'-phosphoinositide-dependent kinase-1 (PDK1) activator under conditions sufficient to induce the cell to become a pluripotent stem cell. In some embodiments, the conditions comprise introducing at least one exogenous transcription factor into the non-pluripotent cell. In some embodiments, the exogenous transcription factor comprises a polypeptide. In some embodiments, the exogenous transcription factor comprises an Oct polypeptide. In some embodiments, the exogenous transcription factor comprises a protein selected from the group consisting of an Oct polypeptide and a Klf polypeptide. In some embodiments, the exogenous transcription factor comprises a protein selected from the group consisting of an Oct polypeptide, a Klf polypeptide, a Myc polypeptide, and a Sox polypeptide. In some embodiments, the condition comprises introducing at least two, three or four exogenous transcription factors into the non-pluripotent cell, wherein the exogenous transcription factors each comprise a different protein selected from the group consisting of an Oct polypeptide, a Klf polypeptide, a Myc polypeptide, and a Sox polypeptide. In some embodiments, the exogenous transcription factor is introduced by introducing a polynucleotide into the non-pluripotent cell, wherein the polynucleotide encodes the exogenous transcription factor, thereby expressing the transcription factor(s) in the non-pluripotent cell. In some embodiments, the exogenous transcription factor is introduced by contacting the exogenous transcription factor to the non-pluripotent cell. In some embodiments, the exogenous transcription factor comprises an amino acid sequence that enhances transport across cell membranes.

In some embodiments, the non-pluripotent cell is a human cell. In some embodiments, the PDK1 activator is present in a concentration sufficient to improve by at least 10% the efficiency of induction of the non-pluripotent cell into an induced pluripotent stem cell, under conditions sufficient to induce conversion of the non-pluripotent cell into the induced pluripotent stem cell.

In some embodiments, the method comprises contacting the non-pluripotent cell with a 3'-phosphoinositide-dependent kinase-1 (PDK1) activator under conditions sufficient to induce the cell to become a pluripotent stem cell. In some embodiments, the method comprises contacting the non-pluripotent cell with a PDK1 activator in the absence of a MEK inhibitor, followed by contacting the non-pluripotent cell with a PDK1 activator and a MEK inhibitor. In some embodiments, the method comprises contacting the non-pluripotent cell with a PDK1 activator, a TGFβ receptor/ALK5 inhibitor, and a histone deacetylase (HDAC) inhibitor in the absence of a MEK inhibitor, followed by contacting the non-pluripotent cell with a PDK1 activator, a TGFβ receptor/ALK5 inhibitor, a histone deacetylase (HDAC) inhibitor and a MEK inhibitor.

In some embodiments, the method further comprises purifying the pluripotent cells to generate a homogenous population of the pluripotent cells. In some embodiments, wherein a plurality of pluripotent stem cells are induced, the method further comprises purifying the pluripotent stem cells to generate a homogenous population of pluripotent stem cells.

In another aspect, the present invention provides for a mixture comprising: mammalian cells, a PDK1 activator, and one or more of (1) a TGFβ receptor/ALK5 inhibitor; (2) a MEK inhibitor; (3) a histone deacetylase (HDAC) inhibitor; or (4) one or more exogenous transcription factors selected from the group consisting of an Oct polypeptide, a Klf polypeptide, a Myc polypeptide, and a Sox polypeptide.

In some embodiments, at least 99% of the cells in the mixture are non-pluripotent cells. In some embodiments, essentially all of the cells are non-pluripotent cells. In some embodiments, the cells are human cells. In some embodiments, the PDK1 activator is an allosteric PDK1 activator, e.g., (Z)-5-(4-Chlorophenyl)-3-phenylpent-2-enoic acid ("PS48"), (Z)-5-(4-Bromo-2-fluorophenyl)-3-phenylpent-2-enoic acid ("PS08"), 2-(3-(4-Chlorophenyl)-3-oxo-1-phenylpropylthio)acetic acid, (Z)-5-(Napthalen-2-yl)-3-phenylpent-2-enoic acid ("12Z"), or (Z)-5-(1H-Indol-3-yl)-3-phenylpent-2-enoic acid ("13Z"). In some embodiments, the mixture further comprises a TGFβ receptor/ALK5 inhibitor, e.g., A-83-01. In some embodiments, the mixture further comprises a MEK inhibitor, e.g., PD0325901. In some embodiments, the mixture further comprises a histone deacetylase (HDAC) inhibitor, e.g., sodium butyrate (NaB), or valproic acid (VPA).

In some embodiments, the mixture further comprises an exogenous transcription factor selected from an Oct polypeptide, a Klf polypeptide, a Myc polypeptide, and a Sox polypeptide. In some embodiments, the exogenous transcription factor comprises an amino acid sequence that enhances transport across cell membranes. In some embodiments, the PDK1 activator in the mixture is present in a concentration sufficient to improve by at least 10% the efficiency of induction of non-pluripotent cells in the mixture into induced pluripotent stem cells under conditions sufficient to induce conversion of the cells into induced pluripotent stem cells.

In still another aspect, the present invention provides for a kit for inducing pluripotency in a non-pluripotent mammalian cell, the kit comprising a PDK1 activator, and one or more of (1) a TGFβ receptor/ALK5 inhibitor; (2) a MEK inhibitor; (3) a histone deacetylase (HDAC) inhibitor; or (4) one or more transcription factors selected from the group consisting of an Oct polypeptide, a Klf polypeptide, a Myc polypeptide, and a Sox polypeptide. In some embodiments, the PDK1 activator is an allosteric PDK1 activator, e.g., (Z)-5-(4-Chlorophenyl)-3-phenylpent-2-enoic acid ("PS48"), (Z)-5-(4-Bromo-2-fluorophenyl)-3-phenylpent-2-enoic acid ("PS08"), 2-(3-(4-Chlorophenyl)-3-oxo-1-phenylpropylthio)acetic acid, (Z)-5-(Napthalen-2-yl)-3-phenylpent-2-enoic acid ("12Z"), or (Z)-5-(1H-Indol-3-yl)-3-phenylpent-2-enoic acid ("13Z"). In some embodiments, the kit further comprises a TGFβ receptor/ALK5 inhibitor, e.g., A-83-01. In some embodiments, the kit further comprises a MEK inhibitor, e.g., PD0325901. In some embodiments, the kit further comprises a histone deacetylase (HDAC) inhibitor, e.g., sodium butyrate (NaB), or valproic acid (VPA).

In some embodiments, the kit further comprises an exogenous transcription factor selected from an Oct polypeptide, a Klf polypeptide, a Myc polypeptide, and a Sox polypeptide. In some embodiments, the exogenous transcription factor comprises an amino acid sequence that enhances transport across cell membranes.

In yet another aspect, the present invention provides a method of inducing a non-pluripotent mammalian cell into an induced pluripotent stem cell. In some embodiments, the method comprises contacting the non-pluripotent cell with a compound that promotes glycolytic metabolism under conditions sufficient to induce the cell to become a pluripotent stem cell, thereby inducing the non-pluripotent mammalian cell into an induced pluripotent stem cell. In some embodiments, the compound that promotes glycolytic metabolism is a PDK1 activator. In some embodiments, the PDK1 activator is an allosteric PDK1 activator, e.g., PS48, PS08, 12Z, or 13Z. In some embodiments, the compound that promotes glycolytic metabolism is a glycolysis activator, e.g., fructose 2,6-bisphosphate. In some embodiments, the compound that promotes glycolytic metabolism is a substrate for glycolysis, e.g., fructose 6-phosphate. In some embodiments, the compound that promotes glycolytic metabolism is a glycolytic intermediate or its metabolic precursors, e.g., nicotinic acid, NADH, or fructose 6-phosphate. In some embodiments, the compound that promotes glycolytic metabolism is a glucose uptake transporter activator. In some embodiments, the compound that promotes glycolytic metabolism is a mitochondrial respiration modulator. In some embodiments, the mitochondrial respiration modulator is an oxidative phosphorylation inhibitor, e.g., 2,4-dinitrophenol, or 2-hydroxyglutaric acid. In some embodiments, the compound that promotes glycolytic metabolism is a hypoxia-inducible factor activator, e.g., N-oxaloylglycine, or quercetin. In some embodiments, the method further comprises contacting the non-pluripotent cell with a TGFβ receptor/ALK5 inhibitor, e.g., A-83-01. In some embodiments, the method further comprises contacting the non-pluripotent cell with a MEK inhibitor, e.g., PD0325901. In some embodiments, the method further comprises contacting the non-pluripotent cell with a histone deacetylase (HDAC) inhibitor, e.g., sodium butyrate (NaB), or valproic acid (VPA).

In some embodiments, the method comprises contacting the non-pluripotent cell with a compound that promotes glycolytic metabolism under conditions sufficient to induce the cell to become a pluripotent stem cell. In some embodiments, the conditions comprise introducing at least one exogenous transcription factor into the non-pluripotent cell. In some embodiments, the exogenous transcription factor comprises a polypeptide. In some embodiments, the exogenous transcription factor comprises an Oct polypeptide. In some embodiments, the exogenous transcription factor comprises a protein selected from the group consisting of an Oct polypeptide and a Klf polypeptide. In some embodiments, the exogenous transcription factor comprises a protein selected from the group consisting of an Oct polypeptide, a Klf polypeptide, a Myc polypeptide, and a Sox polypeptide. In some embodiments, the condition comprises introducing at least two, three or four exogenous transcription factors into the non-pluripotent cell, wherein the exogenous transcription factors each comprise a different protein selected from the group consisting of an Oct polypeptide, a Klf polypeptide, a Myc polypeptide, and a Sox polypeptide. In some embodiments, the exogenous transcription factor is introduced by introducing a polynucleotide into the non-pluripotent cell, wherein the polynucleotide encodes the exogenous transcription factor, thereby expressing the transcription factor(s) in the non-pluripotent cell. In some embodiments, the exogenous transcription factor is introduced by contacting the exogenous transcription factor to the non-pluripotent cell. In some embodiments, the exogenous transcription factor comprises an amino acid sequence that enhances transport across cell membranes.

In some embodiments, the non-pluripotent cell is a human cell. In some embodiments, the compound that promotes glycolytic metabolism is present in a concentration sufficient to improve by at least 10% the efficiency of induction of the non-pluripotent cell into an induced pluripotent stem cell, under conditions sufficient to induce conversion of the non-pluripotent cell into the induced pluripotent stem cell.

In some embodiments, the method comprises contacting the non-pluripotent cell with a compound that promotes glycolytic metabolism under conditions sufficient to induce the cell to become a pluripotent stem cell. In some embodiments, the method comprises contacting the non-pluripotent cell with a compound that promotes glycolytic metabolism and a MEK inhibitor. In some embodiments, the method comprises contacting the non-pluripotent cell with a compound that promotes glycolytic metabolism in the absence of a MEK inhibitor, followed by contacting the non-pluripotent cell with a compound that promotes glycolytic metabolism and a MEK inhibitor. In some embodiments, the method comprises contacting the non-pluripotent cell with a compound that promotes glycolytic metabolism, a TGFβ receptor/ALK5 inhibitor, and a histone deacetylase (HDAC) inhibitor in the absence of a MEK inhibitor, followed by contacting the non-pluripotent cell with a compound that promotes glycolytic metabolism, a TGFβ receptor/ALK5 inhibitor, a histone deacetylase (HDAC) inhibitor and a MEK inhibitor.

In some embodiments, the method further comprises purifying the pluripotent cells to generate a homogenous population of the pluripotent cells. In some embodiments, wherein a plurality of pluripotent stem cells are induced, the method further comprises purifying the pluripotent stem cells to generate a homogenous population of pluripotent stem cells.

In still another aspect, the present invention provides for a mixture comprising: mammalian cells, a compound that promotes glycolytic metabolism, and one or more of (1) a TGFβ receptor/ALK5 inhibitor; (2) a MEK inhibitor; (3) a histone deacetylase (HDAC) inhibitor; or (4) one or more exogenous polypeptides selected from the group consisting of an Oct polypeptide, a Klf polypeptide, a Myc polypeptide, and a Sox polypeptide. In some embodiments, at least 99% of the cells in the mixture are initially non-pluripotent cells. In some embodiments, essentially all of the cells are initially non-pluripotent cells. In some embodiments, the cells are human cells. In some embodiments, the compound that promotes glycolytic metabolism is a PDK1 activator. In some embodiments, the PDK1 activator is an allosteric PDK1 activator, e.g., PS48, PS08, 12Z, or 13Z. In some embodiments, the compound that promotes glycolytic metabolism is a glycolysis activator, e.g., fructose 2,6-bisphosphate. In some embodiments, the compound that promotes glycolytic metabolism is a substrate for glycolysis, e.g., fructose 6-phosphate. In some embodiments, the compound that promotes glycolytic metabolism is a glycolytic intermediate or its metabolic precursors, e.g., nicotinic acid, NADH, or fructose 6-phosphate. In some embodiments, the compound that promotes glycolytic metabolism is a glucose uptake transporter activator. In some embodiments, the compound that promotes glycolytic metabolism is a mitochondrial respiration modulator. In some embodiments, the mitochondrial respiration modulator is an oxidative phosphorylation inhibitor, e.g., 2,4-dinitrophenol, or 2-hydroxyglutaric acid. In some embodiments, the compound that promotes glycolytic metabolism is a hypoxia-inducible factor activator, e.g., N-oxaloylglycine, or quercetin. In some embodiments, the mixture further comprises a TGFβ receptor/ALK5 inhibitor, e.g., A-83-01. In some embodiments, the mixture further comprises a MEK inhibitor, e.g., PD0325901. In some embodiments, the mixture further comprises a histone deacetylase (HDAC) inhibitor, e.g., sodium butyrate (NaB), or valproic acid (VPA).

In some embodiments, the exogenous transcription factor comprises an amino acid sequence that enhances transport across cell membranes. In some embodiments, the compound that promotes glycolytic metabolism in the mixture is present in a concentration sufficient to improve by at least 10% the efficiency of induction of non-pluripotent cells in the mixture into induced pluripotent stem cells under conditions sufficient to induce conversion of the cells into induced pluripotent stem cells.

In yet another aspect, the present invention provides for a kit for inducing pluripotency in a non-pluripotent mammalian cell, the kit comprising a compound that promotes glycolytic metabolism, and one or more of (1) a TGFβ receptor/ALK5 inhibitor; (2) a MEK inhibitor; (3) a histone deacetylase (HDAC) inhibitor; or (4) one or more transcription factors selected from the group consisting of an Oct polypeptide, a Klf polypeptide, a Myc polypeptide, and a Sox polypeptide; or a polynucleotide encoding a transcription factor selected from an Oct polypeptide, a Klf polypeptide, a Myc polypeptide, and a Sox polypeptide. In some embodiments, the compound that promotes glycolytic metabolism is a PDK1 activator. In some embodiments, the PDK1 activator is an allosteric PDK1 activator, e.g., PS48, PS08, 12Z, or 13Z. In some embodiments, the compound that promotes glycolytic metabolism is a glycolysis activator, e.g., fructose 2,6-bisphosphate. In some embodiments, the compound that promotes glycolytic metabolism is a substrate for glycolysis, e.g., fructose 6-phosphate. In some embodiments, the compound that promotes glycolytic metabolism is a glycolytic intermediate or its metabolic precursors, e.g., nicotinic acid, NADH, or fructose 6-phosphate. In some embodiments, the compound that promotes glycolytic metabolism is a glucose uptake transporter activator. In some embodiments, the compound that promotes glycolytic metabolism is a mitochondrial respiration modulator. In some embodiments, the mitochondrial respiration modulator is an oxidative phosphorylation inhibitor, e.g., 2,4-dinitrophenol, or 2-hydroxyglutaric acid. In some embodiments, the compound that promotes glycolytic metabolism is a hypoxia-inducible factor activator, e.g., N-oxaloylglycine, or quercetin. In some embodiments, the kit further comprises a TGFβ receptor/ALK5 inhibitor, e.g., A-83-01. In some embodiments, the kit further comprises a MEK inhibitor, e.g., PD0325901. In some embodiments, the kit further comprises a histone deacetylase (HDAC) inhibitor, e.g., sodium butyrate (NaB), or valproic acid (VPA). In some embodiments, the exogenous transcription factor comprises an amino acid sequence that enhances transport across cell membranes.

DEFINITIONS

An "Oct polypeptide" refers to any of the naturally-occurring members of Octamer family of transcription factors, or variants thereof that maintain transcription factor activity, e.g., within at least 50%, 80%, or 90% activity compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g. Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G. *Genes Dev.* 11, 1207-1225 (1997). In some embodiments, variants have at least 85%, 90%, or 95% amino acid sequence identity across their whole sequence compared to a naturally occurring Oct polypeptide family member such as those listed above or such as listed in Genbank accession number NP_002692.2 (human Oct4) or NP_038661.1 (mouse Oct4). Oct polypeptides (e.g., Oct3/4) can be from human, mouse, rat, bovine, porcine, or other animals. Generally, the same species of protein will be used with the species of cells being manipulated.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity, similar e.g., within at least 50%, 80%, or 90% activity compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W. *Cell* Biol. 32, 1103-1121 (2000). Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., *Nature Biotechnology* 26:101-106 (2007). In some embodiments, variants have at least 85%, 90%, or 95% amino acid sequence identity across their whole sequence compared to a naturally occurring Klf polypeptide family member such as those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described.

A "Myc polypeptide" refers any of the naturally-occurring members of the Myc family (see, e.g., Adhikary, S. & Eilers, M. *Nat. Rev. Mol. Cell. Biol.* 6:635-645 (2005)), or variants thereof that maintain transcription factor activity, e.g., within at least 50%, 80%, or 90% activity compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated. To the extent a Myc polypeptide is described herein, it can be replaced with a Wnt polypeptide, e.g., Wnt 3A (e.g., NP_149122.1), or agent that stimulates the Wnt signaling pathway, e.g., a glycogen synthase kinase alpha or beta inhibitor. Thus, it is intended that for each Myc polypeptide embodiment described herein, a corresponding embodiment using a Wnt polypeptide or agent that stimulates the Wnt signaling pathway in the place of a Myc polypeptide is equally described.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity, e.g., within at least 50%, 80%, or 90% activity compared to the closest related naturally occurring family member or polypeptides comprising at least the DNA-binding domain of the naturally occurring family member, and can further comprise a transcriptional activation domain. See, e.g., Dang, D. T., et al., *Int. J. Biochem. Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., *Nature Biotechnology* 26:101-106 (2007). In some embodiments, variants have at least 85%, 90%, or 95% amino acid sequence identity across their whole sequence compared to a naturally occurring Sox polypeptide family member such as those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated.

An "exogenous transcription factor," as used herein, refers to a transcription factor that is not naturally (i.e., endogenously) expressed in a cell of interest. Thus, an exogenous transcription factor can be expressed from an introduced expression cassette (e.g., under control of a promoter other than a native transcription factor promoter) or can be introduced as a protein from outside the cell. In some embodiments, the exogenous transcription factor comprises an Oct polypeptide (e.g., Oct4), a Klf polypeptide (e.g., Klf4), a Myc polypeptide (e.g., c-Myc), or a Sox polypeptide (e.g., Sox2).

"H3K9" refers to histone H3 lysine 9. H3K9 modifications associated with gene activity include H3K9 acetylation and H3K9 modifications associated with heterochromatin, include H3K9 di-methylation or tri-methylation. See, e.g., Kubicek, et al., *Mol. Cell.* 473-481 (2007). "H3K4" refers to histone H3 lysine 4. See, e.g., Ruthenburg et al., *Mol. Cell.* 25:15-30 (2007).

The term "pluripotent" or "pluripotency" refers to cells with the ability to give rise to progeny that can undergo differentiation, under the appropriate conditions, into cell types that collectively demonstrate characteristics associated with cell lineages from all of the three germinal layers (endoderm, mesoderm, and ectoderm). Pluripotent stem cells can contribute to many or all tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least one, two, or three, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acids.

"Expression cassette" refers to a polynucleotide comprising a promoter or other regulatory sequence operably linked to a sequence encoding a protein.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Inhibitors," "activators," and "modulators" of expression or of activity are used to refer to inhibitory, activating, or modulating molecules, respectively, identified using in vitro and in vivo assays for expression or activity of a described target protein, e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100% Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

The term "allosteric" is used to refer to an effect that affects the activity of one part of an enzyme (such as an active site) by the binding of a molecule at a different site (regulatory site) at a different location on the enzyme. The binding of non-substrate molecules at allosteric sites effects the binding kinetics of the substrate-binding (active) site. "Allosteric binding sites" are contained in many enzymes and receptors. As a result of binding to allosteric binding sites, the interaction with the normal ligand may be either enhanced or reduced. For example, an allosteric binding site in 3'-phosphoinositide-dependent kinase-1 (PDK1) is the PDK1 interacting fragment (PIF) binding pocket located between helix C, helix B and the −4 and −5 sheets (Pearl et al., *Curr. Opin. Struct. Biol.* 12, 761-767 (2002); Biondi et al., *Biochem. J.* 372, 1-13 (2003); Newton et al., *Chem. Rev.* 101, 2353-2364 (2001)).

As used herein, "promote" or "increase," or "promoting" or "increasing" are used interchangeably herein. These terms refer to the increase in a measured parameter (e.g., activity, expression, glycolysis, glycolytic metabolism, glucose uptake, biosynthesis downstream of glycolysis) in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit," "prevent" or "reduce," or "inhibiting," "preventing" or "reducing" are used interchangeably herein. These terms refer to the decrease in a measured parameter (e.g., activity, expression, mitochondrial respiration, mitochondrial oxidation, oxidative phosphorylation) in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is undetectable (i.e., completely inhibited) in the treated cell in comparison to the untreated cell.

and HUVECs (b) were used as negative controls, while vectors were used as positive controls.

Figure 9:
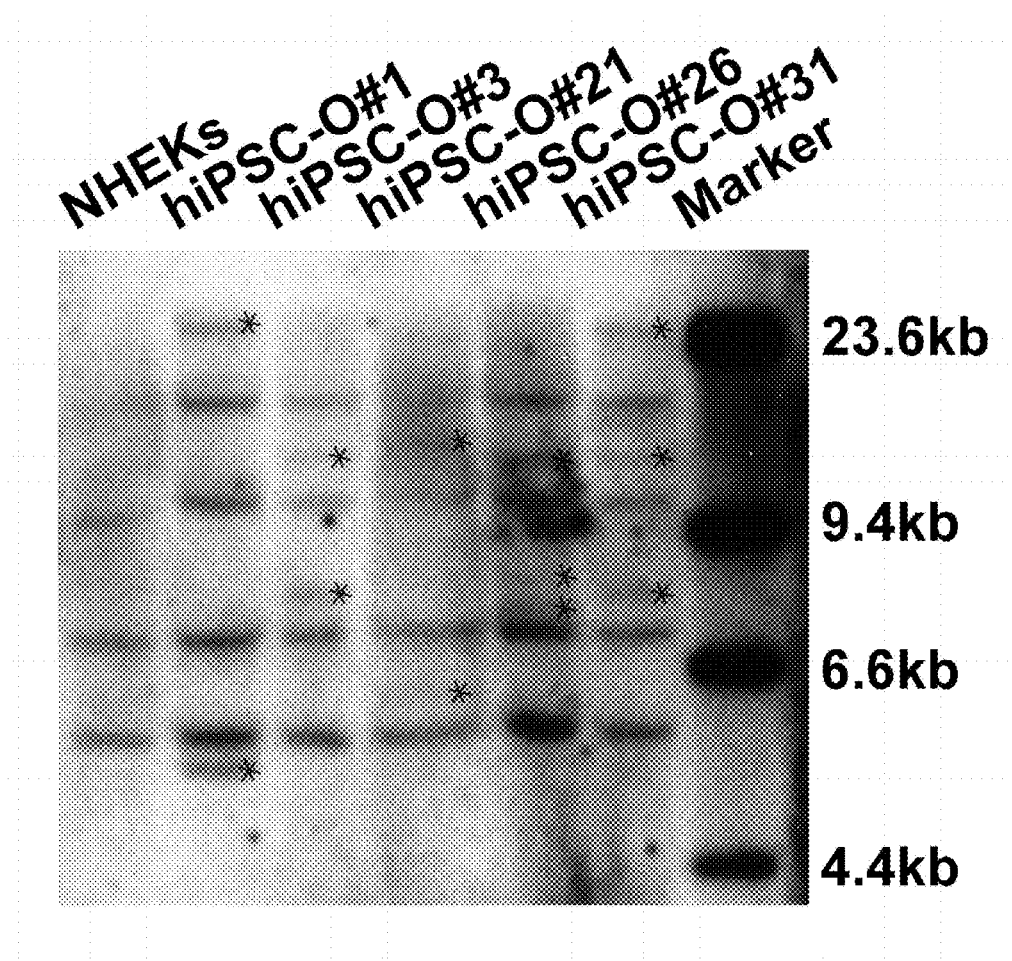

FIG. 9. Integration of the OCT4 transgene in hiPSCs. Genomic DNA (10 μg) were digested with EcoRI and hybridized with the OCT4 cDNA probe (an EcoRI/SpeI fragment of pSin-EF2-OCT4-Pur). Multiple transgenic integrations were detected.

Figure 10:
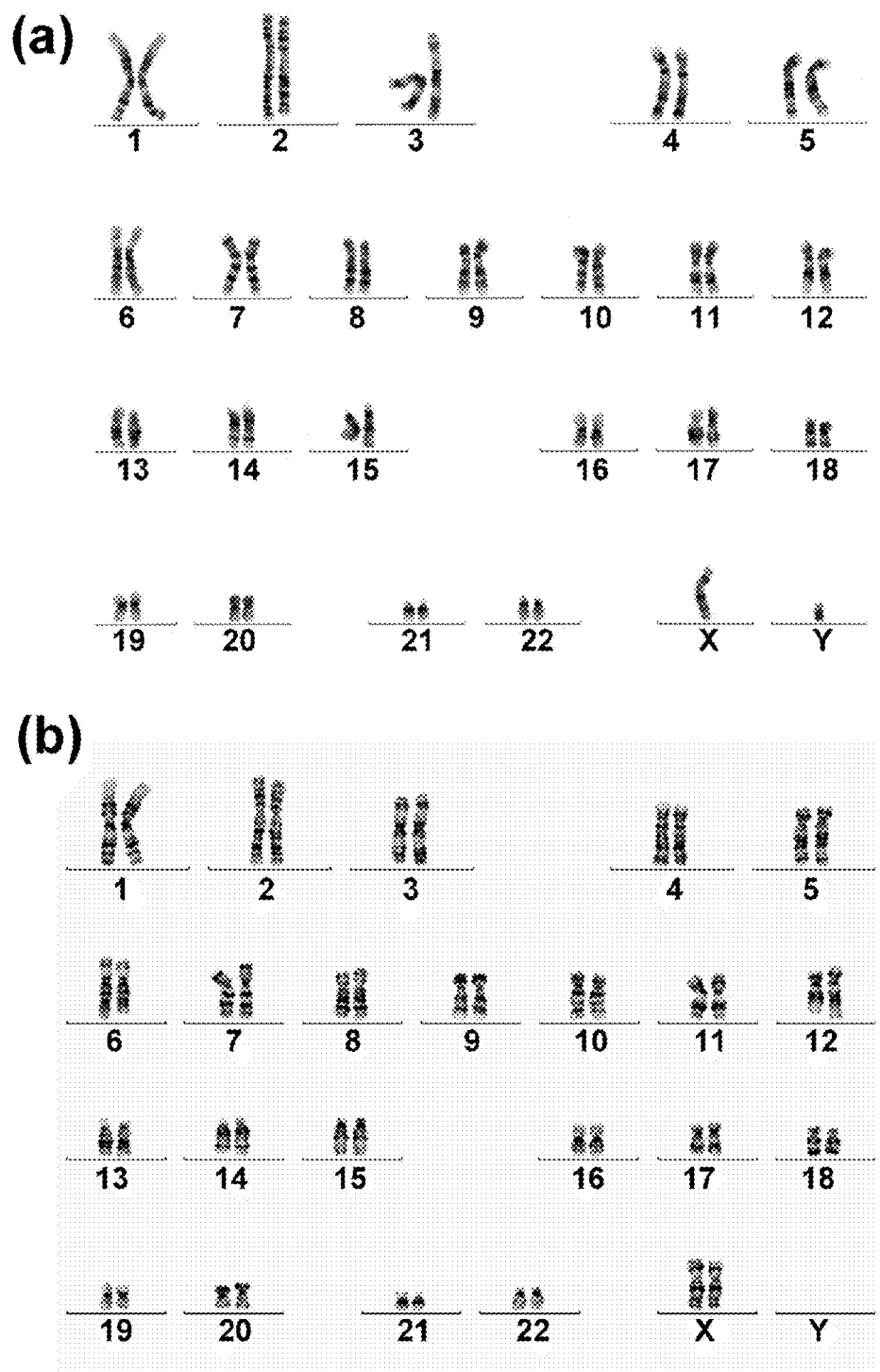

FIG. 10. Karyotyping for hiPSC cell lines. Metaphase spread of hiPSC-O#1 (a) and hiPSC-O#21 (b) show normal karyotype after passage 15.

Figure 11:
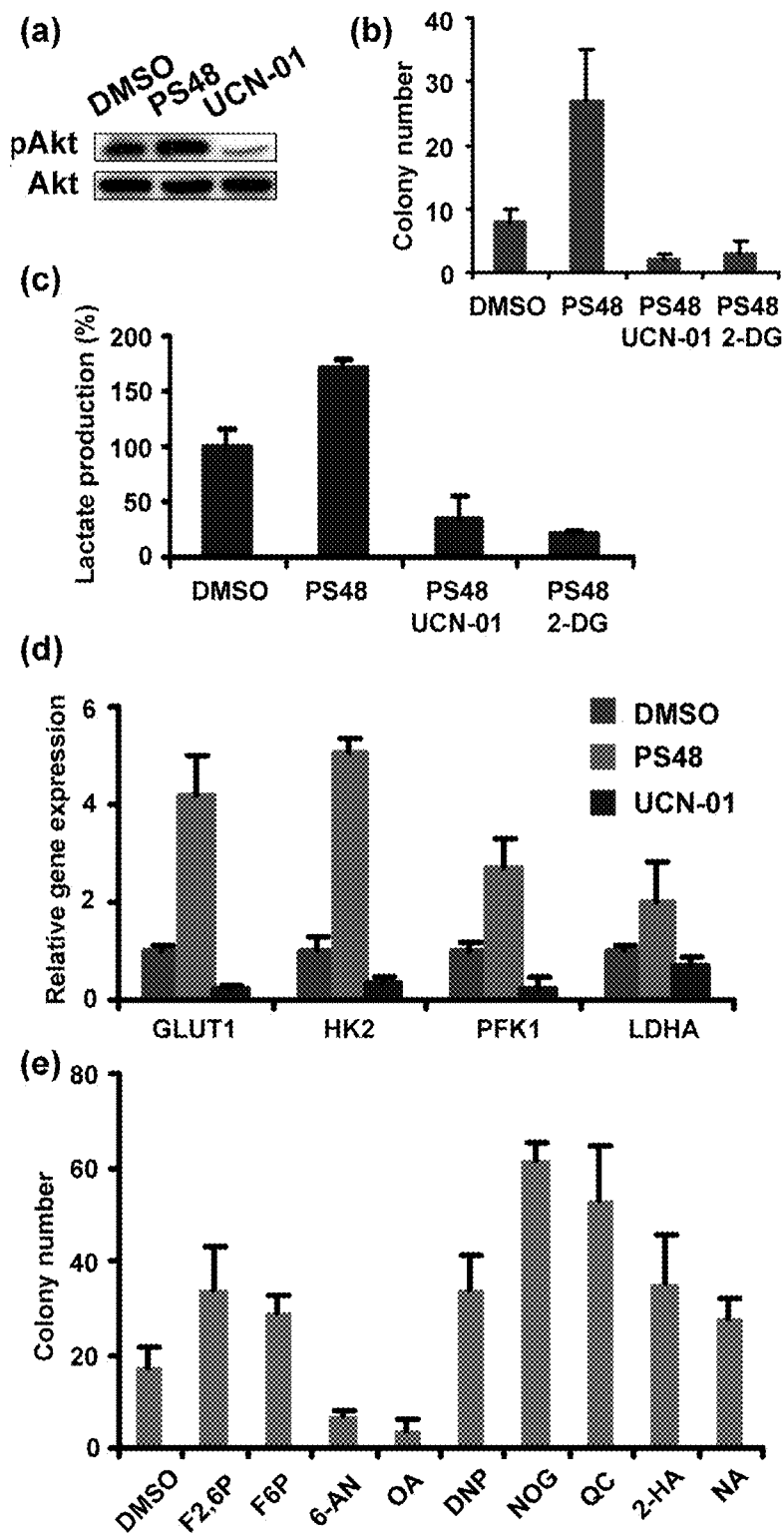

FIG. 11. PS48 enhances reprogramming process by facilitating a metabolic switch toward glycolysis. (a) PS48 treatment activated PDK1 activity. Western blotting analysis of phosphorylation of Akt (Thr-308) after PS48 (5 μM) or UCN-01(20 nM) treatment. (b) PS48 enhanced reprogramming of NHEKs, while UCN-01 (a PDK1 inhibitor) or 2-Deoxy-D-glucose (10 mM) (2-DG, a glycolysis inhibitor) inhibited reprogramming process. Three factor (Klf, Sox, and Oct)-transduced NHEKs were seeded at a density of 100,000 transduced cells per well, treated with compounds for four weeks, and then TRA-1-81 positive colonies were counted. (c) PS48 treatment facilitated/activated a metabolic switch to glycolysis, while treatment of UCN-01 or 2-DG inhibited glycolysis. NHEKs were treated with either PS48, PS48 and UCN-01, or PS48 and 2-DG for 8 d and then lactate production in the medium was measured as a typical index of glycolysis by using the Lactate Assay Kit (BioVision, Mountain View, Calif., USA). (d) PS48 treatment up-regulated the expression of several key glycolytic genes, including GLUT1, HK2, PFK1 and LDHA. (e) Known small molecules that have been widely used to modulate mitochondrial respiration, glycolysis metabolism or HIF activation also showed corresponding consistent effects on reprogramming. Four factor (Klf, Sox, Myc, and Oct)-transduced HUVECs were seeded at a density of 20,000 transduced cells per well, treated with metabolism modulating compounds for three weeks and TRA-1-81 positive colonies were counted. F2, 6P, 10 mM Fructose 2,6-bisphosphate; F6P, 10 mM Fructose 6-phosphate; 6-AN, 10 μM 6-aminonicotinamide; OA, 10 μM oxalate; DNP, 1 μM 2,4-dinitrophenol; NOG, 1 μM N-oxaloylglycine; QC, 1 μM Quercetin; 2-HA, 10 μM 2-Hydroxyglutaric acid; NA, 10 μM nicotinic acid; DMSO was used as a control.

DETAILED DESCRIPTION OF THE INVENTION

I. Introduction

The present invention is based on the surprising discovery that a 3'-phosphoinositide-dependent kinase-1 (PDK1) activator greatly improves efficiency of induction of pluripotency in non-pluripotent mammalian cells. Accordingly, the present invention provides for methods of inducing pluripotency in non-pluripotent mammalian cells wherein the method comprises contacting the non-pluripotent cells with a PDK1 activator.

The present invention is also based on the surprising discovery that compounds that promote glycolytic metabolism as described herein greatly improve efficiency of induction of pluripotency in non-pluripotent mammalian cells. It was discovered in the present invention that compounds that promote glycolytic metabolism facilitate the metabolic reprogramming from mitochondrial oxidation (mainly used by adult somatic cells) to glycolysis (mainly used by embryonic stem cells (ESCs)), thereby inducing pluripotency in non-pluripotent mammalian cells. Compounds that promote glycolysis or compounds that inhibit or impede mitochondrial respiration/oxidation are therefore useful in inducing pluripotency in non-pluripotent mammalian cells. Further, it was discovered that compounds that promote a process either upstream (e.g., PDK1 pathway, hypoxia-inducible factor pathway, glucose uptake transporter pathway) or downstream of glycolysis (e.g., fatty acids synthesis, lipids synthesis, nucleotides synthesis, and amino acids synthesis) are useful in inducing pluripotency in non-pluripotent mammalian cells. Accordingly, the present invention provides for methods of inducing pluripotency in non-pluripotent mammalian cells wherein the method comprises contacting the non-pluripotent cells with one or more compounds that promote glycolytic metabolism as described herein.

To date, a large number of different methods and protocols have been established for inducing non-pluripotent mammalian cells into induced pluripotent stem cells (iPSCs). It is believed that the agents described herein can be used in combination with essentially any protocol for generating iPSCs and thereby improve the efficiency of the protocol. Thus, the present invention provides for incubation of non-pluripotent cells with at least a PDK1 activator, including but not limited to an allosteric PDK1 activator, in combination with any protocol for generating iPSCs. In other embodiments, the present invention provides for incubation of non-pluripotent cells with at least a compound that promotes glycolytic metabolism in combination with any protocol for generating iPSCs.

As used herein, "efficiency of induction," with respect to induction of a non-pluripotent cell into an induced pluripotent stem cell, refers to the number of non-pluripotent cells that can be converted into iPSCs in a defined time frame, or the amount of time it takes to convert a defined number of non-pluripotent cells into iPSCs, under conditions sufficient for inducing pluripotent stem cells. The improvement in efficiency of an iPSC generation protocol will depend on the protocol and which agents of the invention are used. In some embodiments, the efficiency is improved by at least 10%, 20%, 50%, 75%, 100%, 150%, 200%, 300% or more compared to the same protocol without inclusion of the agents of the invention (e.g., a PDK1 activator, e.g., an allosteric PDK1 activator, or a compound that promotes glycolytic metabolism, e.g., PDK1 activators, glycolysis activators, glycolysis substrates, glycolytic intermediates and their metabolic precursors thereof, glucose uptake transporter activators, mitochondrial respiration modulators such as oxidative phosphorylation inhibitors, and hypoxia-inducible factor activators). In some embodiments, efficiency is measured with regard to improvement of the number of iPSCs generated in a particular time frame (e.g., by comparing the number of iPSCs generated from non-pluripotent cells in a defined time frame under conditions comprising the introduction of one or more agents of the invention to the number of iPSCs generated from non-pluripotent cells in the defined time frame under conditions which do not comprise the introduction of one or more agents of the invention). In some embodiments, efficiency is measured with regard to improvement in the speed by which iPSCs are generated (e.g., by comparing the length of time it takes to generate a defined number of iPSCs from non-pluripotent cells under conditions comprising the introduction of one or more agents of the invention to the length of time it takes to generate a defined number of iPSCs from non-pluripotent cells under conditions which do not comprise the introduction of one or more agents of the invention). In some embodiments, efficiency of induction is measured under conditions comprising transducing non-pluripotent cells (e.g., normal human epidermal keratinocytes) with Oct4 and Klf4, then culturing the transduced cells in the absence or presence of one or more agents of the invention (e.g., a PDK1 activator), as described in the Examples section below. Induction of iPSCs from non-pluripotent cells can be measured according to any method known in the art, including but not limited to marker analysis (e.g., using pluripotency markers Tra-1-81 and/or OCT4).

According to the methods of the present invention, specific, context-dependent, treatment regimes can improve reprogramming efficiency. The effectiveness of a certain treatment regime can depend, in some embodiments, on cell types, cell passage numbers, and exogenous transcription factors used. For example, in some embodiments, a more significant improvement in reprogramming efficiency by a specific treatment regime can be observed when reprogramming cells transduced with or in contact with fewer than four exogenous transcription factors, i.e., with one, two, or three exogenous transcription factors, as compared to reprogramming cells transduced with or in contact with four exogenous transcription factors.

In general, human cells can take considerably longer (e.g., 6-8 weeks) to be reprogrammed than mouse cells (e.g., about 2 weeks). The effects of a specific treatment regime, in some embodiments, can be more exaggerated when reprogramming human cells as compared to mouse cells. Accordingly, when relatively longer periods (e.g., at least 3, 4, 5, 6, or more weeks) are used in reprogramming, a treatment regime, e.g., one that uses an epigenetic modifier, can be used to improve reprogramming efficiency.

The inventors have found that epigenetic modifiers can improve reprogramming efficiency. As defined herein, the term "epigenetic modifier" refers to a methylation modifying agent (i.e., agents that induce methylation changes to DNA or histones) and/or an acetylation modifying agent (i.e., agents that induce acetylation changes to DNA or histones). In some embodiments, the methylation modifying agent is a DNA methylation inhibitor (e.g., a DNA methyltransferase (DNMT) inhibitor such as RG108)), histone methylation inhibitor and/or histone demethylation inhibitor. In some embodiments, the acetylation modifying agent is a histone deacetylase (HDAC) inhibitor (e.g., valproic acid (VPA), sodium butyrate (NaB), trichostatin A (TSA), or suberoylanilide hydroxamic acid (SAHA)), a histone acetyltransferase (HAT) inhibitor, histone deacetylase and histone acetyltransferase. In some embodiments, epigenetic modifiers are agents that inhibit methyltranferases or demethylases or agents that activate methyltranferases or demethylases. In some embodiments, the epigenetic modifier is an agent that inhibits histone H3K9 methylation or promotes H3K9 demethylation, e.g., a G9a histone methyltransferase such as BIX01294.

Some epigenetic modifiers, however, may also induce cell differentiation. Accordingly, in some embodiments of the invention, epigenetic modifiers are used only in the earlier stage of the treatment, e.g., in the first 1, 2, 3, or 4 weeks, in the first half, the first ⅓, the first quarter, or the first ⅕ of the treatment period. By omitting epigenetic modifiers in the later stage of the treatment, e.g., in the last 1, 2, 3, or 4 weeks, in the last half, the last ⅓, the last quarter, or the last ⅕ of the treatment period, the side effects of inducing cell differentiation by these epigenetic modifiers can be, at least partially, avoided.

Alternatively, epigenetic modifiers that do not induce differentiation, or only minimally induce differentiation can be used. For example, when HDAC inhibitor is used in a treatment regime, a HDAC inhibitor that does not induce differentiation, or only minimally induces differentiation, e.g., sodium butyrate, is used.

It is further discovered in the present invention that a treatment regime using MEK inhibitors can improve reprogramming efficiency. MEK inhibitors also support cell self-renewal of the induced pluripotent cells. Some MEK inhibitors, however, may inhibit cell proliferation. Accordingly, in some embodiments of the invention, MEK inhibitors are used only in the later stage of the treatment, e.g., in the last 1, 2, 3, or 4 weeks, in the last half, the last ⅓, the last quarter, or the last ⅕ of the treatment period. By omitting MEK inhibitors in the earlier stage of the treatment, e.g., in the first 1, 2, 3, or 4 weeks, in the first half, the first ⅓, the first quarter, or the first ⅕ of the treatment period, cell proliferation is not inhibited in the earlier stage. For example, pluripotency can be induced by contacting a non-pluripotent mammalian cell with a PDK1 activator or with a compound that promotes glycolytic metabolism (e.g., a PDK1 activator) in the absence of a MEK inhibitor in the earlier stage, followed by contacting the non-pluripotent cell with a PDK1 activator or a compound that promotes glycolytic metabolism (e.g., a PDK1 activator) and a MEK inhibitor in the later stage. In some embodiments, the method of inducing pluripotency comprises contacting the non-pluripotent cell with a PDK1 activator or with a compound that promotes glycolytic metabolism (e.g., a PDK1 activator), a TGFβ receptor/ALK5 inhibitor, and a histone deacetylase (HDAC) inhibitor in the earlier stage, followed by contacting the non-pluripotent cell with a PDK1 activator or with a compound that promotes glycolytic metabolism (e.g., a PDK1 activator), a TGFβ receptor/ALK5 inhibitor, a histone deacetylase (HDAC) inhibitor and a MEK inhibitor in the later stage.

II. PDK1 Activators

3'-phosphoinositide-dependent kinase-1 or "PDK1" is a master kinase associated with the activation of AKT/PKB and many other AGC kinases including PKC, S6K, SGK. An important role for PDK1 is in the signaling pathways activated by several growth factors and hormones including insulin signaling. The structure of PDK1 can be divided into two domains; the kinase or catalytic domain and the PH domain. The PH domain functions mainly in the interaction of PDK1 with phosphatidylinositol (3,4)-bisphosphate and phosphatidylinositol (3,4,5)-trisphosphate which is important in localization and activation of some membrane associated PDK1 substrates including AKT. The kinase domain has three ligand binding sites; the substrate binding site, the ATP binding site, and the PIF binding pocket. Several PDK1 substrates including S6K and Protein kinase C require binding at this PIF binding pocket. Small molecule allosteric activators of PDK1 were shown to selectively inhibit activation of substrates that require docking site interaction. These compounds do not bind to the active site and allow PDK1 to activate other substrates that do not require docking site interaction. PDK1 is constitutively active and at present, there are no known inhibitor proteins for PDK1. The activation of PDK1's main effector, AKT, is believed to require a proper orientation of the kinase and PH domains of PDK1 and AKT at the membrane. Phosphoinositide-dependent kinase-1 has been shown to interact with SGK, PRKACA, Sodium-hydrogen exchange regulatory cofactor 2, PRKCD, Protein kinase Mζ (PKMzeta), PKN2, PRKCI, Protein kinase N1, YWHAH and AKT1.

Exemplary PDK1 activators include sphingosine (King et al., Journal of Biological Chemistry, 275:18108-18113, 2000). Exemplary allosteric activators of PDK1 include PS48 ((Z)-5-(4-Chlorophenyl)-3-phenylpent-2-enoic acid), PS08 ((Z)-5-(4-Bromo-2-fluorophenyl)-3-phenylpent-2-enoic acid) (Hindie et al., Nature Chemical Biology, 5:758-764, 2009; Huse & Kuriyan, Cell 109: 275-282, 2002; Johnson & Lewis, Chem. Rev. 101:2209-2242, 2001), and compound I (2-(3-(4-Chlorophenyl)-3-oxo-1-phenylpropylthio)acetic acid) (Engel et al., EMBO J. 25: 5469-5480, 2006); 3,5-diphenylpent-2-enoic acids such as compound 12Z and compound 13Z (12Z: 2-(3-(4-Chlorophenyl)-3-oxo-1-phenylpropylthio)acetic acid, (Z)-5-(Napthalen-2-yl)-3-phenylpent-2-enoic acid; 13Z: (Z)-5-(1H-Indol-3-yl)-3-phenylpent-2-enoic acid (Stroba et al., J. Med. Chem. 52, 4683-4693 (2009)). PS48 has the following formula:

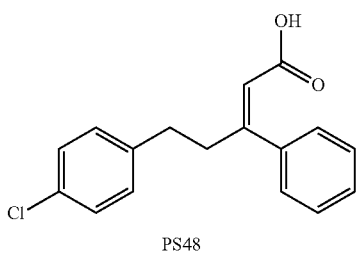 [SMILES: "PS48" ; O=C(O)/C=C(/CCc1ccc(Cl)cc1)c1ccccc1]

PS48

As shown in the Examples, inclusion of a PDK1 activator in cell reprogramming can increase efficiency greatly when used alone and results in even further efficiency increases when used in combination with an HDAC inhibitor. Additional inhibitors, including but not limited to an ALK5 inhibitor and/or a Mek inhibitor, as shown in the Examples, can also be included in reprogramming, particularly where fewer than the four transcription factors (Oct4, Klf4, Sox2, and c-Myc) are introduced into the cell during reprogramming.

III. Compounds that Promote Glycolytic Metabolism

As defined herein, a metabolism modulating compound refers to a compound that modulates (e.g., promotes or inhibits) metabolism of carbohydrate or other molecules. Metabolism modulating compounds include compounds that promote glycolytic metabolism. As defined herein, a compound that promotes glycolytic metabolism refers to a compound that facilitates cellular metabolic reprogramming from mitochondrial oxidation (mainly used by adult somatic cells) to glycolysis (mainly used by ESCs). In some embodiments, a compound that promotes glycolytic metabolism is a compound that promotes glycolysis or a compound that promotes a process upstream of glycolysis (e.g., PDK1 pathway, hypoxia-inducible factor pathway, glucose uptake transporter pathway). In some embodiments, a compound that promotes glycolytic metabolism is a compound that inhibits or impedes mitochondrial respiration. In some embodiments, a compound that promotes glycolytic metabolism is a compound that promotes a process downstream of glycolysis (e.g., fatty acids synthesis, lipids synthesis, nucleotides synthesis, and amino acids synthesis). Examples of compounds that promote glycolytic metabolism include PDK1 activators, glycolysis activators, glycolysis substrates, glycolytic intermediates and their metabolic precursors thereof, glucose uptake transporter activators, mitochondrial respiration modulators such as oxidative phosphorylation inhibitors, and hypoxia-inducible factor activators. In some embodiments, a compound that promotes glycolytic metabolism is not a simple sugar (e.g., a simple sugar commonly used in cell culture medium). Examples of simple sugars include aldoses such as D-glucose, D-mannose and D-galactose, and ketoses such as D-fructose.

1. Glycolysis Activators

Glycolysis activators (e.g., activators of the glycolytic pathway) are known in the art. Enzymes associated with glycolysis pathway are known in the art and include hexokinase, glucokinase, phosphoglucose isomerase, phosphofructokinase, aldolase, triose phosphate isomerase, glyceraldehyde 3-phosphate dehydrogenase, phosphoglycerate kinase, phosphoglyceromutase, enolase, pyruvate kinase and lactate dehydrogenase. In some embodiments, the glycolysis activator (e.g., an activator of the glycolysis pathway) is an activator of an enzyme associated with the glycolytic pathway. In some embodiments, a glycolysis activator is an activator of one of three particular enzymes uniquely associated with the glycolytic pathway: hexokinase, phosphofructokinase, and pyruvate kinase.

Examples of hexokinase activators include phosphate, citrate, D-malate, 3-phosphoglycerate, catecholamines and catecholamines derivatives. In some embodiments, the hexokinase activator is an allosteric activator. In some embodiments, the hexokinase activators do not include phosphate or citrate.

Examples of glucokinase activators include GKA1 (6-[(3-isobutoxy-5-isopropoxybenzoyl)amino]nicotinic acid; Brocklehurst et al., Diabetes 53:535-541, 2004), GKA2 (5-({3-isopropoxy-5-[2-(3-thienyl)ethoxy]benzoyl}amino)-1, 3,4-thiadiazole-2-carboxylic acid; Brocklehurst et al., Diabetes 53:535-541, 2004), RO-28-1675 (Grimsby et al., Science 301:370-373, 2003), and compound A (N-Thiazol-2-yl-2-amino-4-fluoro-5-(1-methylimidazol-2-yl)thiobenzamide; Kamata et al., Structure 12, 429-438, 2004), LY2121260 (2-(S)-cyclohexyl-1-(R)-(4-methanesulfonylphenyl)-cyclopropanecarboxylic acid thiazol-2-ylamide; Efanov et al., Endocrinology, 146:3696-3701, 2005). In some embodiments, the glucokinase activator is an allosteric activator. Additional glucokinase activators are disclosed in WO 00/058293, WO 01/44216, WO 01/83465, WO 01/83478, WO 01/85706, WO 01/85707 and WO 02/08209, WO07/075,847, WO07/061,923, WO07/053,345, WO07/104,034, WO07/089,512, WO08/079,787, WO08/111,473, WO09/106,203, WO09/140,624, WO09/140,624, WO08/079,787, WO02/046173, WO07/006,814, WO07/006,760, WO06/058923, WO02/048106, WO07/125,103, WO07/125,105, WO08/012,227, WO08/074,694, WO08/078,674, WO08/084,043, WO08/084,044, WO09/127,544, WO09/127,546, WO07/125,103, WO07/125,105, WO02/014312, WO04/063179, WO07/006,761, WO07/031,739, WO08/091,770, WO08/116,107, WO08/118,718, WO09/083,553, WO04/052869, WO05/123132, WO04/072066, WO07/117,381, WO07/115,967, WO08/005,964, WO08/154,563, WO09/022,179, WO09/046,784, WO08/005,964, WO/10/080,333, WO/03/095438, WO/06/016194, WO/05/066145, WO/07/115,968, WO/07/143,434, WO/08/005,914, WO/08/149,382, WO/09/018,065, WO/09/047,798, WO/09/046,802, WO/10/029,461, WO/08/005,914, WO/08/149,382, WO/07/143,434, WO/10/103,438, WO/03/047626, WO/05/095418, WO/08/104,994, WO/09/082,152, WO/09/082,152, WO/05/049019, WO/07/048,717, WO/09/042,435, and WO/09/042,435.

Examples of phosphofructokinase (or fructose-6-P kinase) activators include fructose 2,6-bisphosphate.

Examples of pyruvate kinase activators include xylulose 5-P, ceramide, an agonist of the A1 adenosine receptors such as N-6-cyclopentyladenosine. Additional pyruvate kinase activators are disclosed in are disclosed in WO10/042867, WO10/042867, WO99/048490, and WO09/025,781.

Examples of phosphoglucoisomerase activators, aldolase activators, glyceraldehyde 3P dehydrogenase activators, triose phosphate isomerase activators, phosphoglycerate kinase, enolase, phosphoglycerate mutase, and lactate dehydrogenase are known in the art.

2. Glycolysis Substrates

Examples of glycolysis substrates include glucose 6-phosphate, fructose 6-phosphate, fructose 1,6-bisphosphate, glyceraldehyde 3-phosphate, 1,3-bisphosphoglycerate, 3-phosphoglycerate, 2-phosphoglycerate, and phosphoenolpyruvate. In some embodiments, a compound that promotes glycolytic metabolism is not a simple sugar (e.g., glucose).

3. Glycolytic Intermediates and the Metabolic Precursors Thereof.

Glycolytic intermediates are all variously utilized as for biosynthesis of other important molecules such as fatty acids, lipids, nucleotides, and amino acids. Therefore, as defined herein, compounds that promote glycolytic metabolism include compounds that promote a process that is downstream of glycolysis (e.g., fatty acids synthesis, lipids synthesis, nucleotides synthesis, and amino acids synthesis). In some embodiments, compounds that promote glycolytic metabolism include glycolytic intermediates, e.g., glycolytic intermediates that were utilized in these downstream biosynthesis pathways. In some embodiments, compounds that promote glycolytic metabolism include metabolic precursors of glycolytic intermediates. As defined herein, the term "metabolic precursors" refers to compounds from which glycolytic intermediates are metabolically converted, e.g., in a cell, a tissue, or human body.

Examples of glycolytic intermediates include glucose 6-phosphate, fructose 6-phosphate, fructose 1,6-bisphosphate, dihydroxyacetone phosphate, glyceraldehyde 3-phosphate, 1,3-bisphosphoglycerate, 3-phosphoglycerate, 2-phosphoglycerate, phosphoenolpyruvate, oxaloacetate, pyruvate, and metabolite precursors thereof. In some embodiments, the glycolytic intermediate is nicotinamide adenine dinucleotide (NADH). In some embodiments, the compound that promotes glycolytic metabolism is a metabolic precursor of NADH. In some embodiments, the compound that promotes glycolytic metabolism is nicotinic acid or nicotinamide.

4. Glucose Uptake Transporter Activators

As defined herein, the term "glucose uptake transporter activator" refers to compounds that stimulate or otherwise promote the expression or activity of a glucose uptake transporter. As defined herein, the term "glucose transporter" refers to proteins that transport compounds (whether glucose, glucose analogs, other sugars such as fructose or inositol, or non-sugars such as ascorbic acids) across a cell membrane and are members of the glucose transporter "family" based on structural similarity (e.g., homology to other glucose transport proteins). As defined herein, glucose transporters also include transporter proteins that have a primary substrate other than glucose. For example, the glucose transporter GLUT5 is primarily a transporter of fructose, and is reported to transport glucose itself with low affinity. Similarly, the primary substrate for the glucose transporter HMIT is myo-inositol (a sugar alcohol). As used herein, the term "glucose transporter," unless otherwise specified, includes transporters of fructose and inositol. Examples of glucose uptake transporters include a glucose transporter selected from the groups of GLUT1-12, HMIT and SGLT1-6 transporters.

Examples of glucose uptake transporter activators include insulin, pinitol (see, e.g., WO/2000/071111), 8-bromo-cyclic AMP (see, e.g., Ogura et al., Journal of Endocrinology, 164: 171-178, 2000), arachidonic acid (Fong et al., Cellular Signalling, 8:179-183, 1996), phorbol esters such as 12-O-tetradecanoyl-phorbol 13-acetate (see, e.g., Molecular Brain Research, 15:221-226, 1992).

5. Mitochondrial Respiration Modulators (Oxidative Phosphorylation Inhibitors)

As defined herein, the term "mitochondrial respiration" or "mitochondrial oxidation" refers to the oxidation of substrate molecules (e.g., sugars, organic acids, pyruvate, etc.) inside mitochondria. In some embodiments, a compound that promotes glycolytic metabolism is a mitochondrial respiration modulator. A compound that can affect the degree of mitochondria respiration/oxidation is generally referred to herein as a "mitochondrial respiration modulator" or other similar term. In some embodiments, mitochondrial respiration modulator useful for the methods of the invention is a compound that inhibits or impedes mitochondrial respiration or mitochondrial oxidation. In some embodiments, mitochondrial respiration modulator useful for the methods of the invention is an oxidative phosphorylation inhibitor.

An oxidative phosphorylation inhibitor of the invention can be any inhibitor of one or more enzymes of oxidative phosphorylation or an oxidative phosphorylation uncoupler. The oxidative phosphorylation enzymes are known in the art and include enzyme complex I (NADH coenzyme Q reductase), II (succinate-coenzyme Q reductase), III (coenzyme Q cytochrome C reductase), IV (cytochrome oxydase), and V (F0-F1, ATP synthase).

Inhibitors of enzyme complex I are any known in the art and can include, but are not limited to any of the following: tritylthioalanine, caminomycin, and piperazinedione, rotenone, amytal, 1-methyl-4-phenylpyridinium (MPP+), paraquat, methylene blue, and ferricyanide (the latter 2 are electron acceptors) Inhibitors of enzyme complex II are any known in the art. Inhibitors of coenzyme Q are any known in the art. Inhibitors of enzyme complex III are any known in the art and can include, but are not limited to myxothiazol, antimycin A, ubisemiquinone, cytochrome C, 4,6-diaminotriazine derivatives, metothrexate or electron acceptors such as phenazine methosulfate and 2,6-Dichlorophenol-indophenol. Inhibitors of enzyme complex IV are any known in the art and can include, but are not limited to cyanide, hydrogen sulfide, azide, formate, phosphine, carbon monoxide and electon acceptor ferricyanide. Inhibitors of enzyme complex V are any known in the art and can include, but are not limited to 2-hydroxyglutaric acid, VM-26 (4'-demethyl-epipodophyllotoxin thenylidene glucoside), tritylthioalanine, caminomycin, piperazinedione, dinitrophenol, dinitrocresol, 2-hydroxy-3-alkyl-1,4-naphtoquinones, apoptolidin aglycone, oligomycin, ossamycin, cytovaricin, naphtoquinone derivatives (e.g., dichloroallyl-lawsone and lapachol), rhodamine, rhodamine 123, rhodamine 6G, carbonyl cyanide p-trifluoromethoxyphenylhydrazone, rothenone, safranine O, cyhexatin, DDT, chlordecone, arsenate, pentachlorophenol, benzonitrile, thiadiazole herbicides, salicylate, cationic amphilic drugs (amiodarone, perhexyline), gramicidin, calcimycin, pentachlorobutadienyl-cysteine (PCBD-cys), and trifluorocarbonylcyanide phenylhydrazone (FCCP). Other inhibitors of oxidative phorphorylation may include atractyloside, DDT, free fatty acids, lysophospholipids, n-ethylmaleimide, mersanyl, and p-benzoquinone.

Oxidative phosphorylation uncouplers refer to compounds that act as uncouplers of oxidative phosphorylation from electron transport. Examples of oxidative-phosphorylation uncouplers include, but are not limited to, DNP, 5-chloro-3-tert-butyl-2'-chloro-4'-nitrosalicylanilide (S-13), sodium 2,3,4,5,6-pentachlorophenolate (PCP), 4,5,6,7-tetrachloro-2-(trifluoromethyl)-1H-benzimidazole (TTFB), Flufenamic acid (2-[3-(trifluoromethyl)anilino]benzoic acid), 3,5-di-tert-butyl-4-hydroxy-benzylidenemalononitrile (SF6847), carbonyl cyanide m-chloro phenyl hydrazone (CCCP), Carbonyl cyanide p-[trifluoromethoxy]-phenyl-hydrazone (FCCP), and alpha-(phenylhydrazono)phenylacetonitrile derivatives phenylacetonitrile derivatives; and weak acids comprising: Weakly Acidic Phenols, benzimidazoles, N-phenylanthranilates, salicylanilides, phenylhydrazones, salicylic acids, acyldi-thiocarbazates, cumarines, and aromatic amines.

6. Hypoxia-Inducible Factor Activators

Activators of hypoxia-inducible factor pathway are known in the art and include alkaloids and other amino acid derivatives, inhibitors of HIF asparaginyl hydroxylase (factor-inhibiting HIF, or F1H) and HIF prolyl hydroxylases (HPH or PHD), inhibitors of glycogen synthase kinase 3β (GSK3β), nitric oxide (NO) donors, microtubule-depolymerizing agents (MDA), phenolic compounds, terpenes/steroids, and prostaglandin E2 (PGE2). Examples of alkaloids and other amino acid derivatives include deferoxamine and desferriexochelin DFE 722 SM, Ciclopirox olamine [Loprox®, 6-cyclohexyl-1-hydroxy-4-methyl-2(1H)-pyridone 2-aminoethanol], and 8-methyl-pyridoxatin. Examples of inhibitors of glycogen synthase kinase 3β (GSK3β) include indirubin, derivatives of indirubin such as 5-iodoindirubin-3'-oxime and 5-methylindirubin-3'-oxime. Examples of nitric oxide (NO) donors include S-nitroso-N-acetyl-D,L-penicillamine (SNAP), 3-(hydroxy-1-(1-methylethyl)-2-nitrosohydrazino)-1-propanamine (NOC5), diazen-1-ium-1,2-diolate (NOC-18), S-nitrosoglutathione (GSNO), spermine NONOate (a complex of NO with the natural product spermine), diethylamine NONOate, and diethyltryamine NONOate. Examples of microtubule-depolymerizing agents (MDA) include plant alkaloids vinblastine, colchicine, and synthetic MDAs such as nocodazole. Examples of phenolic compounds include dibenzoylmethane (DBM), the flavonoid quercetin (3,3',4',5,7-pentahydroxyflavone), (−)-epicatechin-3-gallate (ECG), and (−)-epigallocatechin-3-gallate (EGCG). Examples of terpenes and steroids include sesquiterpene-tropolones (e.g., pycnidione, epolone A and epolone B), 4-hydroxy estradiol (4-OHE2), dihydrotestosterone, methyltrienolone (R1881), and diterpene ester phorbol 12-O-myristate 13-acetate (PMA, also known as 12-O-tetradecanoylphorbol 13-acetate or TPA).

Examples of inhibitors of HIF asparaginyl hydroxylase (factor-inhibiting HIF, or F1H) and HIF prolyl hydroxylases (HPH or PHD) include analogues of 2-oxoglutarate (2OG) such as N-oxaloylglycine (5, NOG), ester derivatives of NOG (e.g., DMOG (dimethyl-oxalylglycine)), N-((3-hydroxy-6-chloroquinolin-2-yl)carbonyl)-glycine, 3-hydroxypyridine-2-carbonyl-glycine, 3,4-dihydroxybenzoate, pyridine-2,5-dicarboxylate, pyridine-2,4-dicarboxylate, N-oxalyl-2S-alanine, additional analogues of 2OG as described in Mole et al., Bioorg Med Chem. Lett. 13:2677-80, 2003, alahopcin and dealanylalahopcin, dealanylalahopcin analogues 3-carboxymethylene N-hydroxy succinimide, 3-carboxy-N-hydroxy pyrollidone, 1-mimosine (L-Mim), ethyl 3,4-dihydroxybenzoate (3,4-DHB), and 6-chlor-3-hydroxychinolin-2-carbonic acid-N-carboxymethylamid (S956711). Additional HIF asparaginyl hydroxylase and HIF prolyl hydroxylases inhibitors are described in, e.g., Ivan et al., Proc Natl Acad Sci USA 99: 13459-13464, 2002, WO03/049686, WO03/080566, and WO06/084210, WO10/056,767.

Other activators of HIF pathway include iron chelators (e.g., deferoxamine, 2,2'-pyridyl, 1,10-phenanthroline, Ca2+ chelator BAPTA (1,2-bis(2-aminophenoxy)ethane-N,N,N',N'-tetraacetic acid), transition metals (e.g., cobalt, nickel, chromium (VI), and copper), the organomercurial compound mersalyl, and FG-0041 (a compound that is structurally related to 1,10-phenanthroline).

Additional activators of HIF pathway include proteins that up-regulate HIF-1 translation. Protein kinase C (PKC) increases the rate of HIF-1α transcription of and functions in conjunction with the phosphatidylinositol 3-kinase (PI3K) pathway, which also enhances HIF-1α translation. The PKC pathway activates expression of the S6 ribosomal protein, which specifically recognizes mRNA transcripts such as HIF-1α. Via phosphorylation of the S6 protein in normoxic conditions, the rates of HIF-1α mRNA translation can be greatly increased, effectively countering the effects of the proteasome degradation of this subunit and increasing levels of the HIF-1 complex within the cell. The PI3K pathway has been identified as the primary means by which various mediators, such as lipopolysaccharides, affect activation of HIF-1α in vascular smooth muscle cells and macrophages (Dery et al., Int J Biochem Cell Bio. 37:535-540, 2004; Page et al., J Biol. Chem. 277:48403-48409, 2002).

The macrophage-derived peptide PR39 has been shown to stabilize HIF-1α by decreasing its degradation, resulting in accelerated formation of vascular structures in vitro and increased myocardial vasculature in mice (Li et al., Nat Med 6: 49-55. 2000). Direct induction of HIF-1 has been achieved by using the N- or C-terminal of ODDD polypeptides that block VHL-mediated degradation (Maranchie et al., Cancer Cell 1: 247-255, 2002).

HIF pathway activators further include other non-hypoxic physiological stimuli such as growth factors, cytokines, and hormones. Examples of growth factors that activate HIF pathway include insulin-like growth factor (IGF)-1 and IGF-2, IGF-binding protein (IGFBP)-2 and IGFBP-3, EGF, basic fibroblast growth factor (bFGF), and heregulin. Examples of cytokines that activate HIF pathway include tumor necrosis factor alpha (TNFα), interleukin-1 beta (IL-1β), and IL-1. Examples of hormones that activate HIF pathway include the vascular hormones angiotensin II and thrombin, thyroid hormone and follicle-stimulating hormone. Other physiological factors such as the redox protein thioredoxin-1 (Trx-1) and oxidized low-density lipoprotein (oxLDL) can also induce HIF-1α protein and activate HIF-1.

7. PDK1 Activators

In some embodiments, compounds that promote glycolytic metabolism are PDK1 activators. Exemplary PDK1 activators are described herein in section II, supra.

IV. HDAC Inhibitors

Exemplary HDAC inhibitors can include antibodies that bind, dominant negative variants of, and siRNA and antisense nucleic acids that target HDAC. HDAC inhibitors include, but are not limited to, TSA (trichostatin A) (see, e.g., Adcock, British Journal of Pharmacology 150:829-831 (2007)), VPA (valproic acid) (see, e.g., Munster et al., Journal of Clinical Oncology 25:18S (2007): 1065), sodium butyrate (NaBu) (see, e.g., Han et al., Immunology Letters 108:143-150 (2007)), SAHA (suberoylanilide hydroxamic acid or vorinostat) (see, e.g., Kelly et al., Nature Clinical Practice Oncology 2:150-157 (2005)), sodium phenylbutyrate (see, e.g., Gore et al., Cancer Research 66:6361-6369 (2006)), depsipeptide (FR901228, FK228) (see, e.g., Zhu et al., Current Medicinal Chemistry 3(3):187-199 (2003)), trapoxin (TPX) (see, e.g., Furumai et al., PNAS 98(1):87-92 (2001)), cyclic hydroxamic acid-containing peptide 1 (CHAP1) (see, Furumai supra), MS-275 (see, e.g., Carninci et al., WO2008/126932, incorporated herein by reference)), LBH589 (see, e.g., Goh et al., WO2008/108741 incorporated herein by reference) and PXD101 (see, Goh, supra). In general at the global level, pluripotent cells have more histone acetylation, and differentiated cells have less histone acetylation. Histone acetylation is also involved in histone and DNA methylation regulation. In some embodiments, HDAC inhibitors facilitate activation of silenced pluripotency genes.

V. ALK5 Inhibitors

TGFβ receptor (e.g., ALK5) inhibitors can include antibodies to, dominant negative variants of, and antisense nucleic acids that suppress expression of, TGFβ receptors (e.g., ALK5). Exemplary TGFβ receptor/ALK5 inhibitors include, but are not limited to, SB431542 (see, e.g., Inman, et al., *Molecular Pharmacology* 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo et al., *Cancer Science* 96(11):791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton et al., WO2008/094597, herein incorporated by reference), BMP4 (see, Dalton, supra), GW788388 (-{4-[3-(pyridin-2-yl)-1H-pyrazol-4-yl]pyridin-2-yl}-N-(tetrahydro-2H-pyran-4-yl)benzamide) (see, e.g., Gellibert et al., *Journal of Medicinal Chemistry* 49(7):2210-2221 (2006)), SM16 (see, e.g., Suzuki et al., *Cancer Research* 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim et al., *Xenobiotica* 38(3):325-339 (2008)), GW6604 M (2-phenyl-4-(3-pyridin-2-yl-1H-pyrazol-4-yl)pyridine) (see, e.g., de Gouville et al., *Drug News Perspective* 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta et al., *Molecular Pharmacology* 65(3):744-752 (2004)) and pyrimidine derivatives (see, e.g., those listed in Stiefl et al., WO2008/006583, herein incorporated by reference), SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; and soluble TBR2-Fc (see, e.g., Wrzesinski et al., *Clinical Cancer Research* 13(18):5262-5270 (2007); Kaminska et al., *Acta Biochimica Polonica* 52(2):329-337 (2005); and Chang et al., *Frontiers in Bioscience* 12:4393-4401 (2007)). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman et al., *J. Mol. Phamacol.* 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate the MET (i.e., reprogramming) process.

In view of the data herein showing the effect of inhibiting ALK5, it is believed that inhibition of the TGFβ/activin pathway will have similar effects. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD2/3 phosphorylation, inhibitors of the interaction of SMAD2/3 and SMAD4, and activators/agonists of SMAD6 and SMAD7. Furthermore, the categorizations described below are merely for organizational purposes and one of skill in the art would know that compounds can affect one or more points within a pathway, and thus compounds may function in more than one of the defined categories.

Inhibitors of SMAD2/3 phosphorylation can include antibodies to, dominant negative variants of, and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). See, e.g., Wrzesinski, supra; Kaminska, supra; Shimanuki, et al., *Oncogene* 26:3311-3320 (2007); and Kataoka et al., EP1992360, the contents of each of which is incorporated herein by reference.

Inhibitors of the interaction of SMAD2/3 and SMAD4 can include antibodies to, dominant negative variants of, and antisense nucleic acids that target SMAD2, SMAD3 and/or SMAD4. Specific examples of inhibitors of the interaction of SMAD2/3 and SMAD4 include, but are not limited to, Trx-SARA, Trx-xFoxH1b and Trx-Lef1. (See, e.g., Cui et al., *Oncogene* 24:3864-3874 (2005) and Zhao et al., *Molecular Biology of the Cell*, 17:3819-3831 (2006).)

Activators/agonists of SMAD6 and SMAD7 include, but are not limited to, antibodies to, dominant negative variants of, and antisense nucleic acids that target SMAD 6 or SMAD 7. Specific examples of inhibitors include, but are not limited to, smad7-as PTO-oligonucleotides. See, e.g., Miyazono et al., U.S. Pat. No. 6,534,476, and Steinbrecher et al., US2005119203, both incorporated herein by reference.

VI. MEK Inhibitors

Inhibitors of MEK can include antibodies to, dominant negative variants of, and siRNA and antisense nucleic acids that suppress expression of, MEK. Specific examples of MEK inhibitors include, but are not limited to, PD0325901, (see, e.g., Rinehart, et al., *Journal of Clinical Oncology* 22: 4456-4462 (2004)), PD98059 (available, e.g., from Cell Signaling Technology), U0126 (available, for example, from Cell Signaling Technology), SL 327 (available, e.g., from Sigma-Aldrich), ARRY-162 (available, e.g., from Array Biopharma), PD184161 (see, e.g., Klein et al., *Neoplasia* 8:1-8 (2006)), PD184352 (CI-1040) (see, e.g., Mattingly et al., *The Journal of Pharmacology and Experimental Therapeutics* 316:456-465 (2006)), sunitinib (see, e.g., Voss et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluated in Phase I and II clinical trials for cancer (see, e.g., Rinehart et al., *Journal of Clinical Oncology* 22(22):4456-4462 (2004)). Other MEK inhibitors being evaluated in clinical trials include PD184352 (see, e.g., English et al., *Trends in Pharmaceutical Sciences* 23(1):40-45 (2002)), BAY 43-9006 (see, e.g., Chow et al., *Cytometry* (*Communications in Clinical Cytometry*) 46:72-78 (2001)), PD-325901 (also PD0325901), GSK1120212, ARRY-438162, RDEA119, AZD6244 (also ARRY-142886 or ARRY-886), RO5126766, XL518 and AZD8330 (also ARRY-704). See, e.g., information from the National Institutes of Health located on the World Wide Web at clinicaltrials.gov as well as information from the National Cancer Institute located on the World Wide Web at cancer.gov/clinicaltrials.

VII. Reprogramming

To date, a large number of different methods and protocols have been established for inducing non-pluripotent mammalian cells into induced pluripotent stem cells (iPSCs). iPSCs are similar to ESCs in morphology, proliferation, and pluripotency, judged by teratoma formation and chimaera contribution. It is believed that PDK1 activators or compounds that promote glycolytic metabolism (e.g., PDK1 activators), optionally in combination with an HDAC inhibitor, and optionally an ALK5 inhibitor and optionally a Mek inhibitor, will improve essentially any reprogramming protocol for generating iPSCs. Reprogramming protocols that can be improved are believed to include those involving introduction of one or more reprogramming transcription factors selected from an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc). Thus, in some embodiments, conditions sufficient to induce a cell to become a pluripotent stem cell comprise conditions in which one or more reprogramming transcription factors selected from an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc) are introduced into the cell. As noted in the Examples, PDK1 activators have been shown to improve reprogramming with as few as one reprogramming transcription factor (e.g., Oct4 alone). Thus, in some embodiments, conditions sufficient to induce a cell to become a pluripotent stem cell comprise conditions in which one reprogramming transcription factor (e.g., Oct4 alone) is introduced into the cell.

In some embodiments, conditions sufficient to induce a cell to become a pluripotent stem cell comprise introducing reprogramming factors into the cells, for example, by expression from a recombinant expression cassette that has been introduced into the target cell, or by incubating the cells in the presence of exogenous reprogramming transcription factor polypeptides such that the polypeptides enter the cell.

Studies have shown that retroviral transduction of mouse fibroblasts with four transcription factors that are highly expressed in ESCs (Oct-3/4, Sox2, KLF4 and c-Myc) generate induced pluripotent stem (iPS) cells. See, Takahashi, K. & Yamanaka, S. *Cell* 126, 663-676 (2006); Okita, K., Ichisaka, T. & Yamanaka, S, *Nature* 448, 313-317 (2007); Wernig, M. et al. *Nature* 448, 318-324 (2007); Maherali, N. et al. *Cell Stem Cell* 1, 55-70 (2007); Meissner, A., Wernig, M. & Jaenisch, R. *Nature Biotechnol.* 25, 1177-1181 (2007); Takahashi, K. et al. *Cell* 131, 861-872 (2007); Yu, J. et al. *Science* 318, 1917-1920 (2007); Nakagawa, M. et al. *Nature Biotechnol.* 26, 101-106 (2007); Wernig, M., Meissner, A., Cassady, J. P. & Jaenisch, R. *Cell Stem Cell.* 2, 10-12 (2008). Studies have also demonstrated reprogramming of human somatic cells with transcription factors that are highly expressed in ESCs: Hockemeyer et al. *Cell Stem Cell.* 11; 3(3):346-53 (2008); Lowry et al. *Proc Natl Acad Sci USA.* 105(8):2883-8 (2008); Park et al. *Nature.* 10; 451(7175):141-6 (2008); Nakagawa et al. *Nat Biotechnol.* January; 26(1):101-6 (2008); Takahashi et al. *Cell.* 131(5):861-72 (2007); and Yu et al. *Science.* 318(5858): 1917-20 (2007). Such methods are believed to be improved with the inclusion of a PDK1 activator or one or more compounds that promote glycolytic metabolism (e.g., a PDK1 activator) and optionally other agents as described herein.

To address the safety issues that arise from target cell genomes harboring integrated exogenous sequences, a number of modified genetic protocols have been further developed and can be used according to the present invention. These protocols produce iPS cells with potentially reduced risks, and include non-integrating adenoviruses to deliver reprogramming genes (Stadtfeld, M., et al. (2008) *Science* 322, 945-949), transient transfection of reprogramming plasmids (Okita, K., et al. (2008) *Science* 322, 949-953), piggy-Bac transposition systems (Woltjen, K., et al. (2009). *Nature* 458, 766-770, Yusa et al. (2009) *Nat. Methods* 6:363-369, Kaji, K., et al. (2009) *Nature* 458, 771-775), Cre-excisable viruses (Soldner, F., et al. (2009) *Cell* 136, 964-977), and oriP/EBNA1-based episomal expression system (Yu, J., et al. (2009) *Science* DOI: 10.1126); the contents of each of which is incorporated by reference herein in its entirety. Thus, in some embodiments, conditions sufficient to induce a cell to become a pluripotent stem cell comprise conditions in which reprogramming factors are delivered by non-integrating adenoviruses, transient transfection of reprogramming plasmids, piggyBac transposition systems, re-excisable viruses (Soldner, F., et al. (2009) *Cell* 136, 964-977), and/or oriP/EBNA1-based episomal expression systems, according to any of the protocols described above. In some embodiments, a PDK1 activator or one of more compounds that promote glycolytic metabolism (e.g., a PDK1 activator) and optionally other agents as described herein are incubated with cells in any of the protocols described above.

As noted above, reprogramming can involve culturing target cells in the presence of one or more proteins under conditions to allow for introduction of the proteins into the cell. See, e.g., Zhou H et al., *Cell Stem Cell.* 2009 May 8; 4(5): 381-4; WO/2009/117439. One can introduce an exogenous polypeptide (i.e., a protein provided from outside the cell and/or that is not produced by the cell) into the cell by a number of different methods that do not involve introduction of a polynucleotide encoding the polypeptide. In some embodiments, conditions sufficient to induce a cell to become a pluripotent stem cell comprise introducing into the cell one or more exogenous proteins, each exogenous protein comprising a transcription factor polypeptide of interest linked (e.g., linked as a fusion protein or otherwise covalently or noncovalently linked) to a polypeptide that enhances the ability of the transcription factor to enter the cell (and in some embodiments the cell nucleus).

Examples of polypeptide sequences that enhance transport across membranes include, but are not limited to, the *Drosophila* homeoprotein antennapedia transcription protein (AntHD) (Joliot et al., *New Biol.* 3: 1121-34,1991; Joliot et al., *Proc. Natl. Acad. Sci. USA*, 88: 1864-8,1991; Le Roux et al., *Proc. Natl. Acad. Sci. USA,* 90: 9120-4, 1993), the herpes simplex virus structural protein VP22 (Elliott and O'Hare, *Cell* 88: 223-33, 1997); the HIV-1 transcriptional activator TAT protein (Green and Loewenstein, *Cell* 55: 1179-1188, 1988; Frankel and Pabo, *Cell* 55: 1289-1193, 1988); Kaposi FGF signal sequence (kFGF); protein transduction domain-4 (PTD4); Penetratin, M918, Transportan-10; a nuclear localization sequence, a PEP-1 peptide; an amphipathic peptide (e.g., an MPG peptide); delivery enhancing transporters such as described in U.S. Pat. No. 6,730,293 (including but not limited to a peptide sequence comprising at least 5-25 or more contiguous arginines (SEQ ID NO:11 or 5-25 or more arginines in a contiguous set of 30, 40, or 50 amino acids; including but not limited to an peptide having sufficient, e.g., at least 5, guanidino or amidino moieties); and commercially available Penetratin™ 1 peptide, and the Diatos Peptide Vectors ("DPVs") of the Vectocell® platform available from Daitos S. A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes. A number of polypeptides capable of mediating introduction of associated molecules into a cell have been described previously and can be adapted to the present invention. See, e.g., Langel (2002) Cell Penetrating Peptides CRC Press, Pharmacology and Toxicology Series.

Exemplary polypeptide sequences that enhance transport across membranes include:

```
VP22:
                                        (SEQ ID NO: 2)
G S P P T A P T R S K T P A Q G L A R K L H F S T
A P P N P D A P W T P R V A G F N K R V F R F S P
Q T A R R A T T T R I;

kFGF:
                                        (SEQ ID NO: 3)
A G S G G A A V A L L P A V L L A L L A P G G E F
A;

PTD4:
                                        (SEQ ID NO: 4)
A G S G G Y A R A A A R Q A R A G G E F A;

PENETRATIN:
                                        (SEQ ID NO: 5)
R Q I K I W F Q G R R M K W K K;

TAT:
                                        (SEQ ID NO: 6)
Y G R K K R R Q R R R;

M918:
                                        (SEQ ID NO: 7)
M V T V L F R R L R I R R A C G P P R V R V;

TRANSPORTAN-10:
                                        (SEQ ID NO: 8)
A G Y L L G K I G L K A L A A L A K K I L.
```

In some embodiments, the polypeptide that enhances transport across membranes is a peptide sequence comprising at least 5 or more contiguous or non-contiguous arginines (e.g., a an 8-arginine peptide; SEQ ID NO:9). In some embodiments, the polypeptide that enhances transport across membranes is a peptide sequence comprising at least 7 or more contiguous or non-contiguous arginines. For example, the polypeptide that enhances transport across membranes is a peptide sequence comprising 11 contiguous arginines (SEQ ID NO:10), e.g., ESGGGGSPGRRRRRRRRRRR (SEQ ID NO:11). As noted above, the arginines in the transport enhancing sequence need not all be contiguous. In some embodiments, the polyarginine (e.g., the contiguous or non-contiguous) region is at least 5, 8, 10, 12, 15, 20, or more amino acids long and has at least e.g., 40%, 50%, 60%, 70%, 80%, 90%, or more arginines.

In some embodiments, conditions sufficient to induce a cell to become a pluripotent stem cell comprise conditions in which one or more exogenous polypeptides, e.g., an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc), is introduced into cells by traditional methods such as lipofection, electroporation, calcium phosphate precipitation, particle bombardment and/or microinjection, or can be introduced into cells by a protein delivery agent. For example, the exogenous polypeptide can be introduced into cells by covalently or noncovalently attached lipids, e.g., by a covalently attached myristoyl group. Lipids used for lipofection are optionally excluded from cellular delivery modules in some embodiments. In some embodiments, the transcription factor polypeptides described herein are exogenously introduced as part of a liposome, or lipid cocktail (such as commercially available Fugene6 and Lipofectamine). In another alternative, the transcription factor proteins can be microinjected or otherwise directly introduced into the target cell. In some embodiments, the transcription factor polypeptides are delivered into cells using Profect protein delivery reagents, e.g., Profect-P1 and Profect-P2 (Targeting Systems, El Cajon, Calif.), or using Pro-Ject® transfection reagents (Pierce, Rockford Ill., USA). In some embodiments, the transcription factor polypeptides are delivered into cells using a single-wall nano tube (SWNT).

As discussed in the Examples of WO/2009/117439, incubation of cells with the transcription factor polypeptides of the invention for extended periods can be toxic to the cells. Therefore, in some embodiments of the invention, conditions sufficient to induce the non-pluripotent mammalian cell to become a pluripotent stem cell comprise incubating a PDK1 activator or one or more compounds that promote glycolytic metabolism (e.g., a PDK1 activator) and optionally an HDAC inhibitor, an ALK5 inhibitor and/or a Mek inhibitor, and intermittently incubating the non-pluripotent mammalian cell with one or more of an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc) with intervening periods of incubation of the cell in the absence of the one or more polypeptides. In some embodiments, the cycle of incubation with and without the polypeptides can be repeated for 2, 3, 4, 5, 6, or more times and is performed for sufficient lengths of time (i.e., the incubations with and without proteins) to achieve the development of pluripotent cells.

The various agents (e.g., PDK1 activator or compounds that promote glycolytic metabolism, HDAC inhibitor, TGFβ receptor/ALK5 inhibitor, MEK/ERK pathway inhibitor, and/or Rho GTPase/ROCK inhibitor, etc.) can be contacted to non-pluripotent cells either prior to, simultaneously with, or after delivery of, programming transcription factors (for example, delivered via expression cassette or as proteins). For convenience, the day the reprogramming factors are delivered is designated "day 1." In some embodiments, the inhibitors are contacted to cells in aggregate (i.e., as a "cocktail") at about days 3-7 and continued for 7-14 days. Alternatively, in some embodiments, the cocktail is contacted to the cells at day 0 (i.e., a day before the preprogramming factors) and incubated for about 14-30 days.

The cell into which a protein of interest is introduced can be a mammalian cell. The cells can be human or non-human (e.g., primate, rat, mouse, rabbit, bovine, dog, cat, pig, etc.). The cell can be, e.g., in culture or in a tissue, fluid, etc. and/or from or in an organism. Cells that can be induced to pluripotency include, but are not limited to, keratinocyte cells, hair follicle cells, HUVEC (Human Umbilical Vein Endothelial Cells), cord blood cells, neural progenitor cells and fibroblasts.

In some embodiments, small molecules can improve the efficiency of a process for generating pluripotent cells (e.g., iPS cells). For example, improved efficiency can be manifested by speeding the time to generate such pluripotent cells (e.g., by shortening the time to development of pluripotent cells by at least a day compared to a similar or same process without the small molecule). Alternatively, or in combination, a small molecule can increase the number of pluripotent cells generated by a particular process (e.g., increasing the number in a given time period by at least 10%, 30%, 50%, 100%, 200%, 500%, etc. compared to a similar or same process without the small molecule).

Optionally, or in addition, small molecules can "complement" or replace what is generally otherwise understood as a necessary expression of one of these proteins to result in pluripotent cells. By contacting a cell with an agent that functionally replaces one of the transcription factors, it is possible to generate pluripotent cells with all of the above-listed transcription factors except for the transcription factor replaced or complemented by the agent.

VIII. Transformation

This invention employs routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)). In some embodiments, expression cassettes for expression of one or more reprogramming transcription factor is introduced into a cell.

In some embodiments, the species of cell and protein to be expressed is the same. For example, if a mouse cell is used, a mouse ortholog is introduced into the cell. If a human cell is used, a human ortholog is introduced into the cell.

It will be appreciated that where two or more proteins are to be expressed in a cell, one or multiple expression cassettes can be used. For example, where one expression cassette expresses multiple polypeptides, a polycistronic expression cassette can be used.

Any type of vector can be used to introduce an expression cassette of the invention into a cell. Exemplary vectors include but are not limited to plasmids and viral vectors. Exemplary viral vectors include, e.g., adenoviral vectors, AAV vectors, and retroviral (e.g., lentiviral) vectors.

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art (e.g., Stadtfeld and Hochedlinger, *Nature Methods* 6(5):329-330 (2009); Yusa et al., *Nat. Methods* 6:363-369 (2009); Woltjen, et al., *Nature* 458, 766-770 (9 Apr. 2009)). Such methods include, but are not limited to, direct delivery of DNA such as by ex vivo transfection (Wilson et al., *Science,* 244:1344-1346, 1989, Nabel and Baltimore, *Nature* 326:711-713, 1987), optionally with Fugene6 (Roche) or Lipofectamine (Invitrogen), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, *J. Cell Biol.,* 101: 1094-1099, 1985; U.S. Pat. No. 5,789,215, incorporated herein by reference); by electroporation (U.S. Pat. No. 5,384, 253, incorporated herein by reference; Tur-Kaspa et al., *Mol. Cell Biol.,* 6:716-718, 1986; Potter et al., *Proc. Nat'l Acad. Sci. USA,* 81:7161-7165, 1984); by calcium phosphate precipitation (Graham and Van Der Eb, Virology, 52:456-467, 1973; Chen and Okayama, *Mol. Cell. Biol.,* 7(8):2745-2752, 1987; Rippe et al., *Mol. Cell Biol.,* 10:689-695, 1990); by using DEAE-dextran followed by polyethylene glycol (Gopal, *Mol. Cell Biol.,* 5:1188-1190, 1985); by direct sonic loading (Fechheimer et al., *Proc. Nat'l Acad. Sci. USA,* 84:8463-8467, 1987); by liposome mediated transfection (Nicolau and Sene, *Biochim. Biophys. Acta,* 721:185-190, 1982; Fraley et al., *Proc. Nat'l Acad. Sci. USA,* 76:3348-3352, 1979; Nicolau et al., *Methods Enzymol.,* 149:157-176, 1987; Wong et al., *Gene,* 10:87-94, 1980; Kaneda et al., *Science,* 243:375-378, 1989; Kato et al., *J Biol. Chem.,* 266: 3361-3364, 1991) and receptor-mediated transfection (Wu and Wu, Biochemistry, 27:887-892, 1988; Wu and Wu, *J. Biol. Chem.,* 262:4429-4432, 1987); and any combination of such methods, each of which is incorporated herein by reference.

IX. Mixtures

As discussed herein, the present invention provides for mammalian cells in a mixture with a PDK1 activator or a compound that promotes glycolytic metabolism, and one or more of (a) a TGFβ receptor/ALK5 inhibitor; (b) a MEK inhibitor; (c) a histone deacetylase (HDAC) inhibitor; or (d) an exogenous polypeptide selected from an Oct polypeptide, a Klf polypeptide, a Myc polypeptide, and a Sox polypeptide. In some embodiments, the compound that promotes glycolytic metabolism is a PDK1 activator. In some embodiments, the PDK1 activator is an allosteric PDK1 activator, e.g., PS48. In some embodiments, the compound that promotes glycolytic metabolism is a glycolysis activator, e.g., fructose 2,6-bisphosphate. In some embodiments, the compound that promotes glycolytic metabolism is a substrate for glycolysis, e.g., fructose 6-phosphate. In some embodiments, the compound that promotes glycolytic metabolism is a glycolytic intermediate or its metabolic precursors, e.g., nicotinic acid, NADH, or fructose 6-phosphate. In some embodiments, the compound that promotes glycolytic metabolism is a glucose uptake transporter activator. In some embodiments, the compound that promotes glycolytic metabolism is a mitochondrial respiration modulator. In some embodiments, the mitochondrial respiration modulator is an oxidative phosphorylation inhibitor, e.g., 2,4-dinitrophenol, or 2-hydroxyglutaric acid. In some embodiments, the compound that promotes glycolytic metabolism is a hypoxia-inducible factor activator, e.g., N-oxaloylglycine, or quercetin.

In some embodiments, the mixture further comprises a TGFβ receptor/ALK5 inhibitor. TGFβ receptor/ALK5 inhibitors include but are not limited to A-83-01. In some embodiments, the mixture further comprises a MEK inhibitor. MEK inhibitors include but are not limited to PD0325901. In some embodiments, the mixture further comprises a histone deacetylase (HDAC) inhibitor. HDAC inhibitors include but are not limited to sodium butyrate (NaB) and valproic acid (VPA). In some embodiments, the mixture further comprises an exogenous transcription factor, e.g., an exogenous transcription factor selected from an Oct polypeptide, a Klf polypeptide, a Myc polypeptide, and a Sox polypeptide. In some embodiments, the exogenous transcription factor comprises an amino acid sequence that enhances transport across cell membranes.

In some embodiments, the compound (e.g., the PDK1 activator or the compound that promotes glycolytic metabolism) is present in the mixture at a concentration sufficient to induce or improve efficiency of induction to pluripotency. For example, in some embodiments, the compounds are in a concentration of at least 0.1 nM, e.g., at least 1, 10, 100, 1000, 10000, or 100000 nM, e.g., between 0.1 nM and 100000 nM, e.g., between 1 nM and 10000 nM, e.g., between 10 nM and 10000 nM. In some embodiments, the mixtures are in a synthetic vessel (e.g., a test tube, Petri dish, etc.). Thus, in some embodiments, the cells are isolated cells (not part of an animal). In some embodiments, the cells are isolated from an animal (human or non-human), placed into a vessel, contacted with one or more compound as described herein. The cells can be subsequently cultured and optionally, inserted back into the same or a different animal, optionally after the cells have been stimulated to become a particular cell type or lineage. In some embodiments, the concentration of the inhibitors is sufficient to improve by at least 10%, 20%, 50%, 75%, 100%, 150%, 200%, 300% or more, the efficiency of induction of non-pluripotent cells in the mixture into induced pluripotent stem cells when the mixture is submitted to conditions sufficient to induce conversion of the cells into induced pluripotent stem cells.

As explained herein, in some embodiments, the cells comprise an expression cassette for heterologous expression of at least one or more of an Oct polypeptide, a Myc polypeptide, a Sox polypeptide and a Klf polypeptide. In some embodiments, the cells do not include an expression cassette to express one or more (including in some embodiments, any) of the Oct, Myc, Sox, or Klf polypeptides.

The cells according to the present invention can be human or non-human (e.g., primate, rat, mouse, rabbit, bovine, dog, cat, pig, etc.). Examples of non-pluripotent cells include those described herein, including but not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, T-cells, keratinocyte cells, hair follicle cells, human umbilical vein endothelial cells (HUVEC), cord blood cells, and neural progenitor cells. In some embodiments, at least 99% of the cells in the mixture are initially non-pluripotent cells. In some embodiments, essentially all of the cells in the mixture are initially non-pluripotent cells.

In some embodiments, at least 0.001%, at least 0.002%, at least 0.005%, at least 0.01%, at least 0.05%, at least 0.1%, at least 0.5%, least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, or at least 90% of the cells in the mixture are induced into pluripotent cells. In some embodiments, at least 99% of the cells in the mixture are induced into pluripotent cells. In some embodiments, essentially all of the cells are induced into non-pluripotent cells.

X. Kits

The present invention provides a kit for inducing pluripotency in a non-pluripotent mammalian cell comprising a PDK1 activator or a compound that promotes glycolytic metabolism, and one or more of (a) a TGFβ receptor/ALK5 inhibitor; (b) a MEK inhibitor; (c) a histone deacetylase (HDAC) inhibitor; or (d) an exogenous polypeptide selected from an Oct polypeptide, a Klf polypeptide, a Myc polypeptide, and a Sox polypeptide. In some embodiments, the compound that promotes glycolytic metabolism is a PDK1 activator. In some embodiments, the PDK1 activator is an allosteric PDK1 activator, e.g., PS48. In some embodiments, the compound that promotes glycolytic metabolism is a glycolysis activator, e.g., fructose 2,6-bisphosphate. In some embodiments, the compound that promotes glycolytic metabolism is a substrate for glycolysis, e.g., fructose 6-phosphate. In some embodiments, the compound that promotes glycolytic metabolism is a glycolytic intermediate or its metabolic precursors, e.g., nicotinic acid, NADH, or fructose 6-phosphate. In some embodiments, the compound that promotes glycolytic metabolism is a glucose uptake transporter activator. In some embodiments, the compound that promotes glycolytic metabolism is a mitochondrial respiration modulator. In some embodiments, the mitochondrial respiration modulator is an oxidative phosphorylation inhibitor, e.g., 2,4-dinitrophenol, or 2-hydroxyglutaric acid. In some embodiments, the compound that promotes glycolytic metabolism is a hypoxia-inducible factor activator, e.g., N-oxaloylglycine, or quercetin.

In some embodiments, the kit further comprises a TGFβ receptor/ALK5 inhibitor, e.g., A-83-01. In some embodiments, the kit further comprises a MEK inhibitor, e.g., PD0325901. In some embodiments, the kit further comprises a histone deacetylase (HDAC) inhibitor, e.g., sodium butyrate (NaB), or valproic acid (VPA). In some embodiments, the kit further comprises an exogenous transcription factor, e.g., an exogenous transcription factor selected from an Oct polypeptide, a Klf polypeptide, a Myc polypeptide, and a Sox polypeptide. In some embodiments, the exogenous transcription factor comprises an amino acid sequence that enhances transport across cell membranes.

In some embodiments, the kits further comprise non-pluripotent cells. Examples of non-pluripotent cells include those described herein, including but not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, T-cells, keratinocyte cells, hair follicle cells, human umbilical vein endothelial cells (HUVEC), cord blood cells, and neural progenitor cells.

EXAMPLES

The following examples are offered to illustrate, but not to limit the claimed invention.

Example 1

Reprogramming of Human Primary Somatic Cells by OCT4 and Chemical Compounds Here we report a novel small molecule cocktail that enables reprogramming of human primary somatic cells to iPSCs with exogenous expression of only OCT4.

Results

Among several readily available primary human somatic cell types, keratinocytes that can be easily isolated from human skin or hair follicle represent an attractive cell source for reprogramming, because they endogenously express KLF4 and cMYC, and were reported to be reprogrammed more efficiently using the conventional four TFs or three TFs (without MYC) (Aasen, T. et al., *Nat Biotechnol* 26:1276-1284 (2008); Maherali, N. et al., *Cell Stem Cell* 3, 340-345 (2008)). More recently, we reported that dual inhibition of TGFβ and MAPK/ERK pathways using small molecules (i.e., SB431542 and PD0325901, respectively) provides a drastically enhanced condition for reprogramming of human fibroblasts with four exogenous TFs (i.e., Oct4, Sox2, Klf4, and c-Myc TFs, or "OSKM") (Lin, T. et al., *Nat Methods* 6:805-808 (2009)). Furthermore, we have shown that such dual pathway inhibition could also enhance reprogramming of human keratinocytes by two exogenous TFs (i.e., Oct4 and Klf4, or "OK") with two small molecules, Parnate (an inhibitor of lysine-specific demethylase 1) and CHIR99021 (a GSK3 inhibitor) (Li, W. et al., *Stem Cells* 27:2992-3000 (2009)). However, such a 2-TFs reprogramming process was very inefficient and complex (e.g., involving two exogenous TFs and four chemicals), and reprogramming with even one less TF appeared daunting. Toward the OCT4 only reprogramming, we developed a step-wise strategy in refining reprogramming condition and identifying new reprogramming chemical entities.

Figure 1:
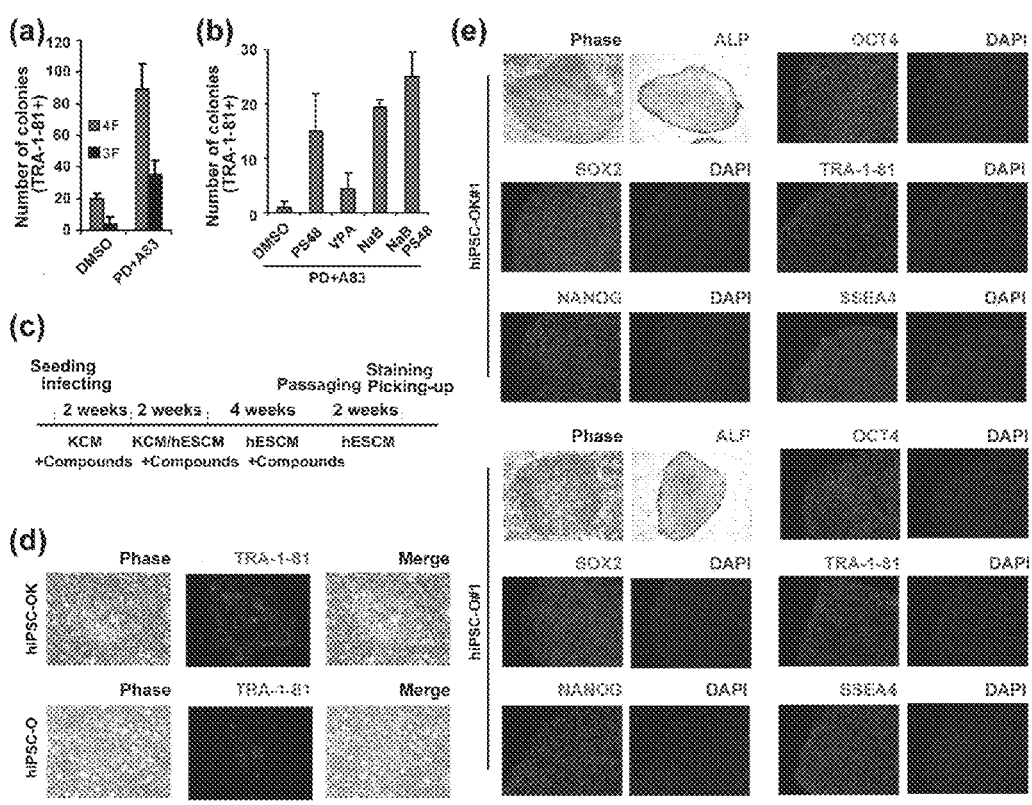
FIG. 1. Generation of human induced pluripotent stem cells from primary keratinocytes by single gene, OCT4, and small molecules. (a) Treatment with 0.5 µM PD0325901 (PD) and 0.5 µM A-83-01 (A83) significantly improved generation of iPSCs from primary human keratinocytes transduced with either 4TFs (4F, OKSM) or 3TFs (3F, OKS). NHEKs were seeded at a density of 100,000 transduced cells per 10 cm dish. (b) Further chemical screens identified PS48, NaB, and their combination that can substantially enhance reprogramming of primary human keratinocytes transduced with 2TFs (OK). NHEKs were seeded at a density of 100,000 transduced cells per 10 cm dish. (c) Experimental scheme for generation of human iPSCs from primary human keratinocytes transduced by a single reprogramming gene, OCT4. KCM, keratinocyte culture medium; hESCM, human ESC culture media. (d) Live immunostaining with TRA-1-81 of iPSC colonies that were generated from primary human keratinocytes transduced with 2TFs/OK or 1TF/OCT4 before picking-up of colonies. (e) The established human iPSC-OK and iPSC-O cells express typical pluripotency markers, including ALP (alkaline phosphatase), OCT4, SOX2, NANOG, SSEA-4 and TRA-1-81. Nuclei were stained with DAPI.

We first attempted to further optimize the reprogramming process under the four or three TFs (i.e., OSKM or OSK) condition in neonatal human epidermal keratinocytes (NHEKs) by testing various inhibitors of TGFβ and MAPK pathways at different concentrations using previously reported human iPSC characterization methods (Lin, T. et al., *Nat Methods* 6:805-808 (2009)). We found that the combination of 0.5 µM PD0325901 and 0.5 µM A-83-01 (a more potent and selective TGFβ receptor inhibitor) was more effective in enhancing reprogramming of human keratinocytes transduced with OSKM or OSK (FIG. 1a). Remarkably, when we further reduced viral transductions to only two factors/OK, we could still generate iPSCs from NHEKs when they were treated with 0.5 µM PD0325901 and 0.5 µM A-83-01, although with low efficiency. Then we began screening additional small molecules from a collection of known bioactive compounds at various concentrations as previously reported. Among dozens of compounds tested so far, surprisingly we found that a small molecule activator of PDK1 (3'-phosphoinositide-dependent kinase-1), PS48 (5 µM) that has never been reported in reprogramming, can significantly enhance the reprogramming efficiency about fifteen fold. Interestingly, we also found that 0.25 mM sodium butyrate (NaB, a histone deacetylase inhibitor) turned out to be much more reliable and efficient than the previously reported 0.5 mM VPA for the generation of iPSCs under OK condition (FIG. 1b). Subsequent follow-up studies demonstrated that the combination of 5 µM PS48 and 0.25 mM NaB could further enhance the reprogramming efficiency over twenty-five fold (FIG. 1b and Table 3).

Figure 2:
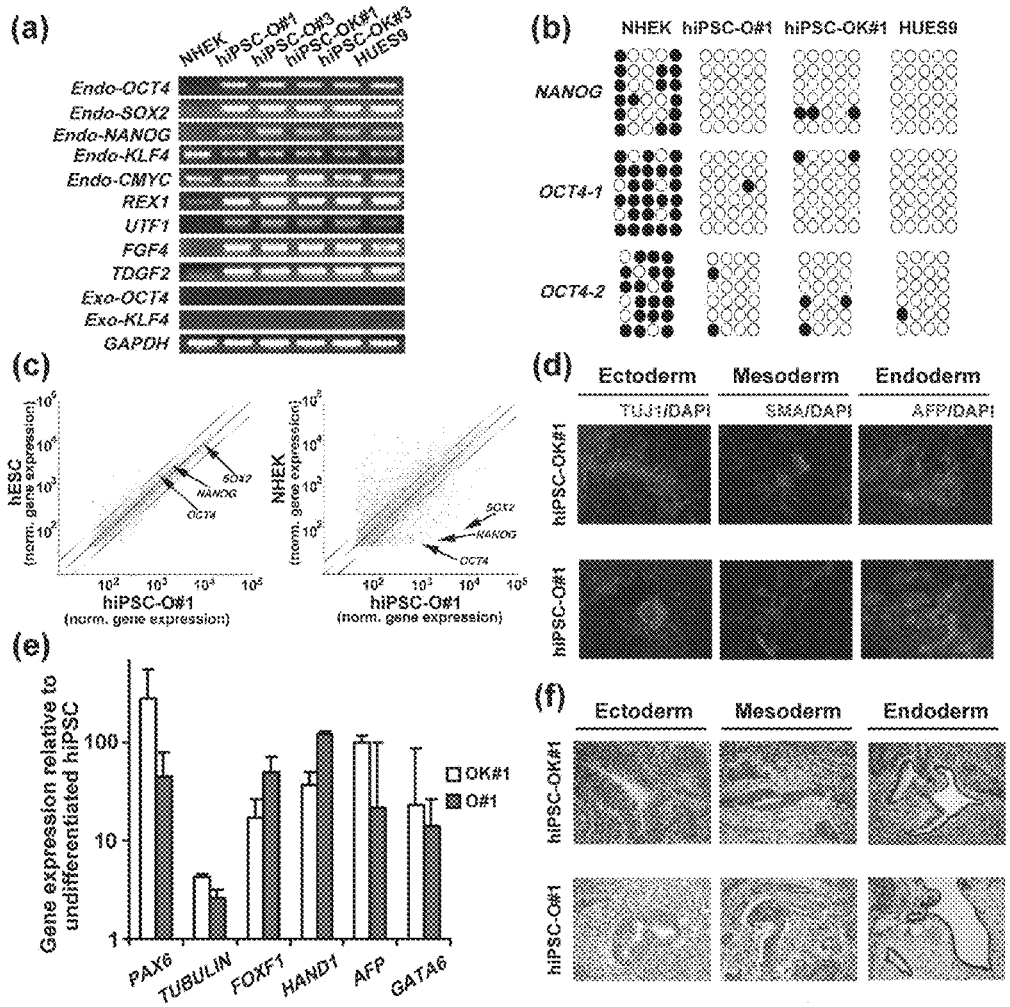
FIG. 2. In depth characterizations of human iPSC-OK and iPSC-O cells. (a) Expression analysis by RT-PCR of the endogenous pluripotency genes and exogenous OCT4 and KLF4. GAPDH was used as an input control. (b) Methylation analysis of the OCT4 and NANOG promoters by bisulfite genomic sequencing. Open circles and closed circles indicate unmethylated and methylated CpGs in the promoter regions, respectively. (c) Scatter plots comparing global gene expression patterns between iPSC-O cells and NHEKs, and hESCs. The positions of the pluripotency genes OCT4, NANOG, and SOX2 are shown by arrows. Black lines indicate the linear equivalent and twofold changes in gene expression levels between the samples. (d) Human iPSC-OK and iPSC-O could effectively differentiate in vitro into cells in the three germ layers, including neural ectodermal cells (βIII tubulin$^+$), mesodermal cells (SMA$^+$), and endodermal cells (AFP$^+$) using EB method. (e) Quantitative PCR test of three germ layer markers from differentiated human iPSCs using EB method: ectoderm (PAX6, βIII TUBULIN), mesoderm (FOXF1, HAND1) and endoderm (AFP, GATA6). Data denotes GAPDH-normalized fold changes relative to undifferentiated parental human iPSCs. (f) Human iPSC-OK and iPSC-O could effectively produce full teratoma, which contains differentiated cells in the three germ layers, in SCID mice.

With such unprecedented efficiency in reprogramming NHEKs under only two TFs, we further explored the possibility of generating iPSCs with OCT4 alone by refining combinations of those small molecules during different treatment windows. Primary NHEKs were transduced with OCT4 and treated with chemicals (FIG. 1c). Among various conditions, small iPSC colonies resembling hESCs (four to six colonies out of 1,000,000 seeded cells) appeared in OCT4 infected NHEKs that were treated with 0.25 mM NaB, 5 µM PS48 and 0.5 µM A-83-01 during the first four weeks, followed by treatment with 0.25 mM NaB, 5 µM PS48, 0.5 µM A-83-01 and 0.5 µM PD0325901 for another four weeks (FIG. 1c). Such TRA-1-81 positive iPSC colonies (FIG. 1d) grew larger under conventional hESC culture media and could be serially passaged to yield stable iPSC clones that were further characterized (FIGS. 1e and 2). In addition, OCT4 only iPSCs could also be generated from human adult keratinocytes by addition of 2 µM Parnate and 3 µM CHIR99021 (which had been shown to improve reprogramming of NHEKs under OK condition) to this chemical cocktail. After the reliable reprogramming of primary keratinocytes to iPSCs by OCT4 and small molecules, we further applied the conditions to other human primary cell types, including HUVECs (differentiated mesoderm cells) and AFDCs (amniotic fluid derived cells). Similarly, TRA-1-81 positive iPSC colonies appeared in OCT4 infected HUVECs and AFDCs that were treated with chemicals. Remarkably, it appeared that reprogramming of HUVECs and AFDCs was more efficient and faster than reprogramming of NHEKs under the OCT4 and small molecule conditions (Table 3). Two clones of iPSCs from each cell type were long-term expanded for over 20 passages under conventional hESC culture condition and further characterized (Table 4).

Figure 3:
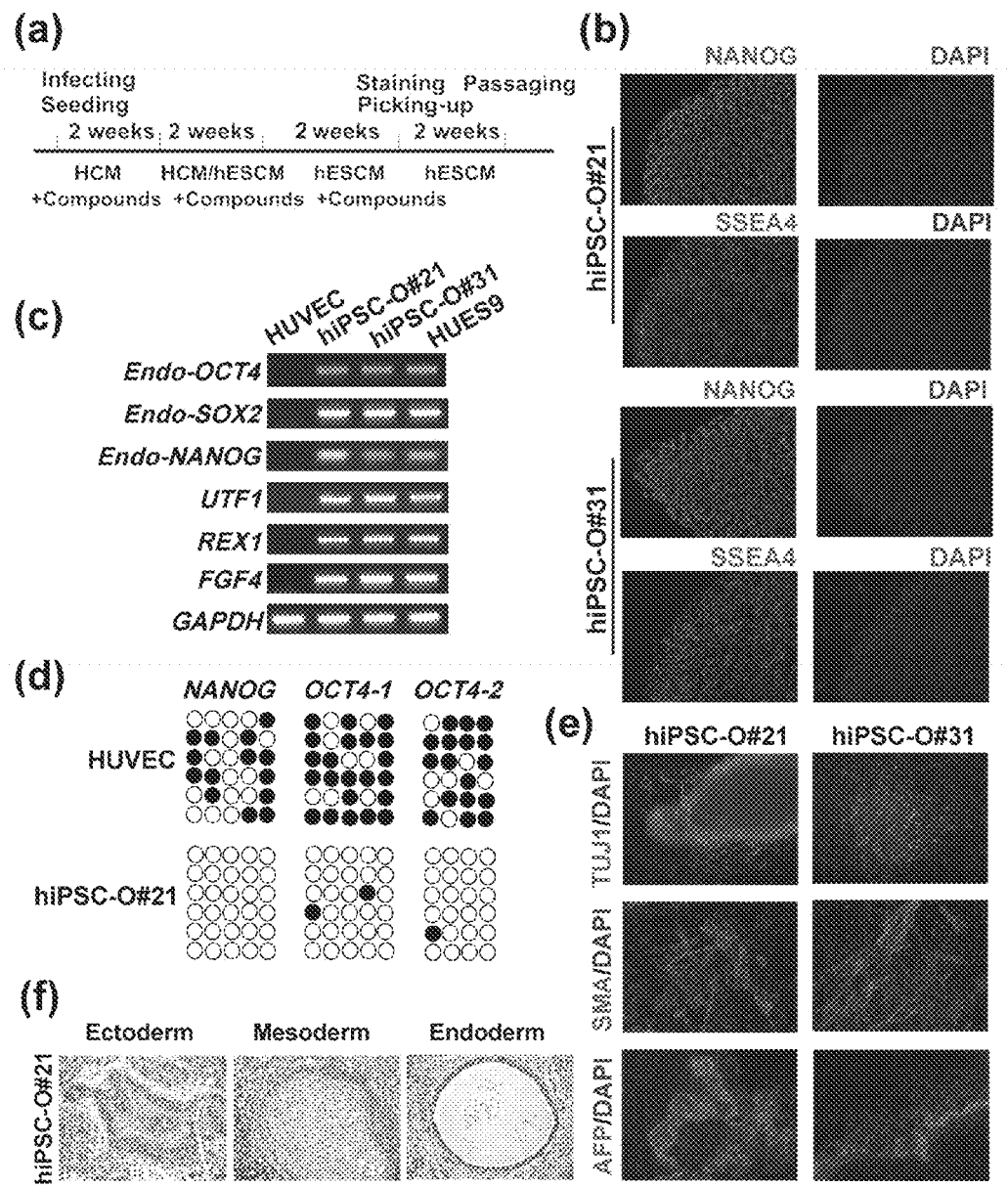
FIG. 3. Generation and characterization of human induced pluripotent stem cells from human umbilical vein endothelial cells by single gene, OCT4, and small molecules. (a) Experimental scheme for generation of human iPSCs from HUVECs transduced by OCT4. HCM, HUVEC culture medium; hESCM, human ESC culture media. (b) The established hiPSC-O cells from HUVECs express typical pluripotency markers, including NANOG and SSEA-4. Nuclei were stained with DAPI. (c) Expression analysis by RT-PCR of the endogenous pluripotency genes. GAPDH was used as an input control. (d) Methylation analysis of the OCT4 and NANOG promoters by bisulfite genomic sequencing. Open circles and closed circles indicate unmethylated and methylated CpGs in the promoter regions, respectively. (e) hiPSC-O cells from HUVECs could effectively differentiate in vitro into cells in the three germ layers, including neural ectodermal cells (βIII tubulin), mesodermal cells (SMA$^+$), and endodermal cells (AFP$^+$) using EB method. (f) hiPSC-O cells could effectively produce full teratoma, which contains differentiated cells in the three germ layers in SCID mice.
Figure 4:
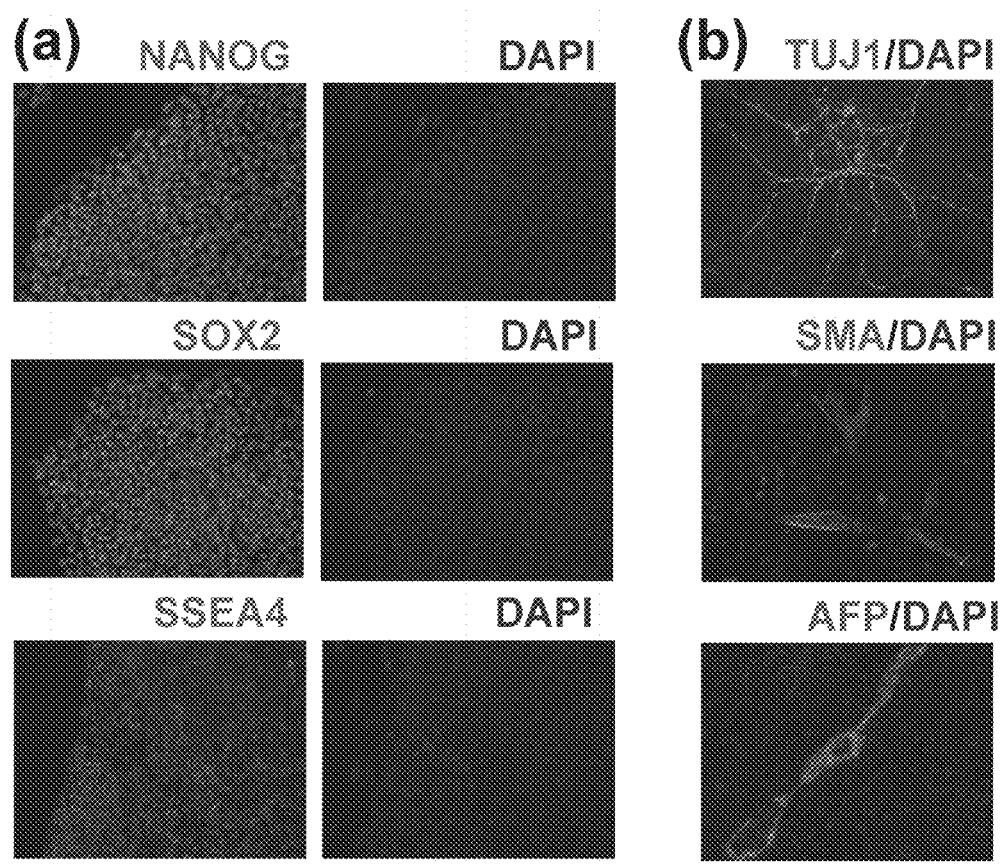
FIG. 4. Characterization of human iPSC-O cells from AHEKs. (a) The established hiPSC-O cells from adult keratinocytes express typical pluripotency markers, including NANOG, SOX2 and SSEA-4. Nuclei were stained with DAPI. (b) These hiPSC-O cells could effectively differentiate in vitro into cells in the three germ layers, including neural ectodermal cells (βIII tubulin$^+$), mesodermal cells (SMA$^+$), and endodermal cells (AFP$^+$) using EB method.
Figure 5:
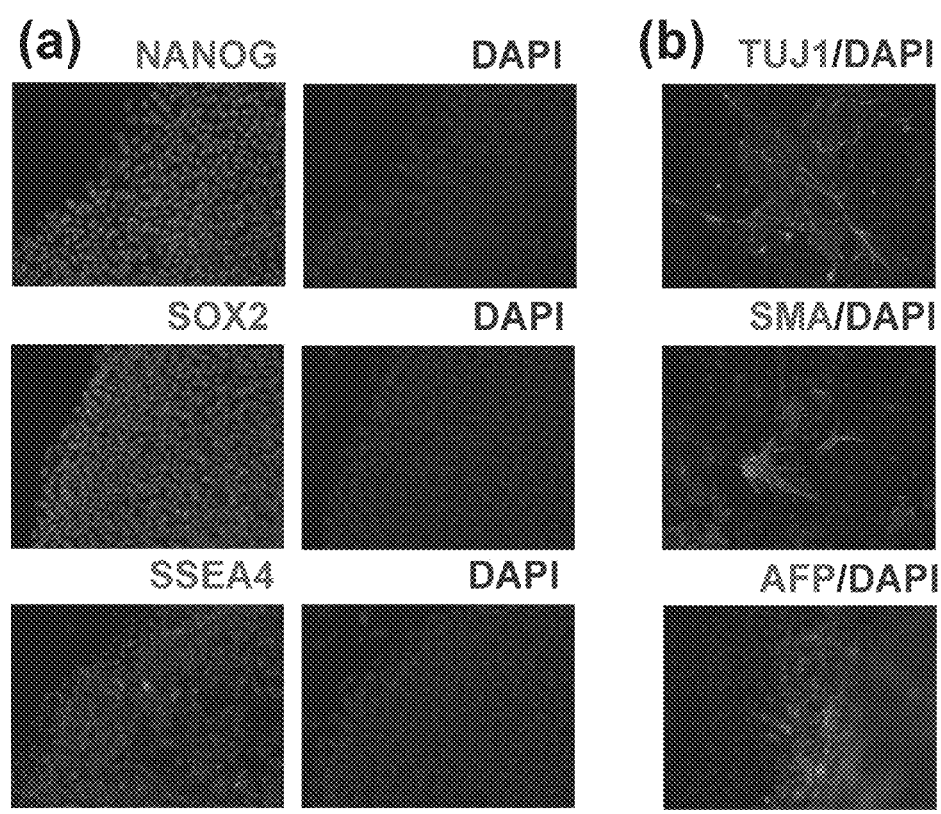
FIG. 5. Characterization of hum an iPSC-O cells from AFDCs. (a) The established hiPSC-O cells from amniotic fluid derived cells express typical pluripotency markers, including NANOG, SOX2 and SSEA-4. Nuclei were stained with DAPI. (b) These hiPSC-O cells could effectively differentiate in vitro into cells in the three germ layers, including neural ectodermal cells (βIII tubulin$^+$), mesodermal cells (SMA$^+$), and endodermal cells (AFP$^+$) using EB method.
Figure 6:
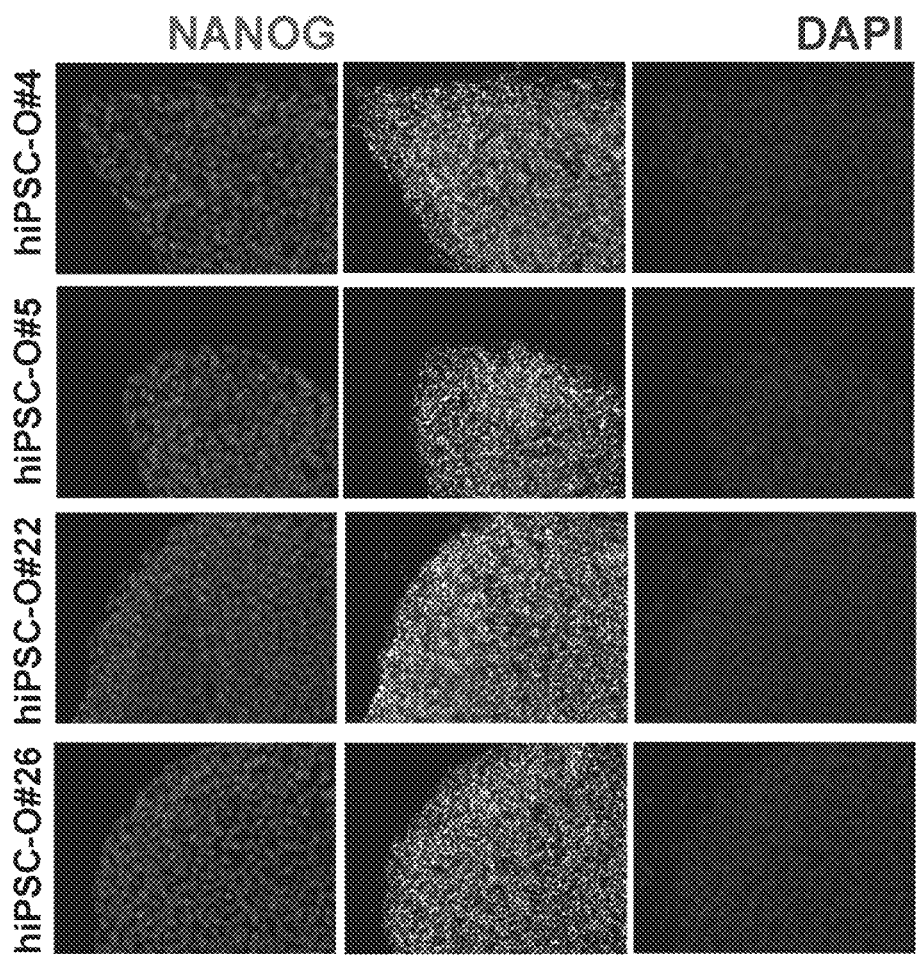
FIG. 6. Additional hiPSC cell lines express typical pluripotency markers. The other established hiPSC-O cell lines express typical pluripotency markers, including NANOG and SSEA-4. Nuclei were stained with DAPI.
Figure 7:
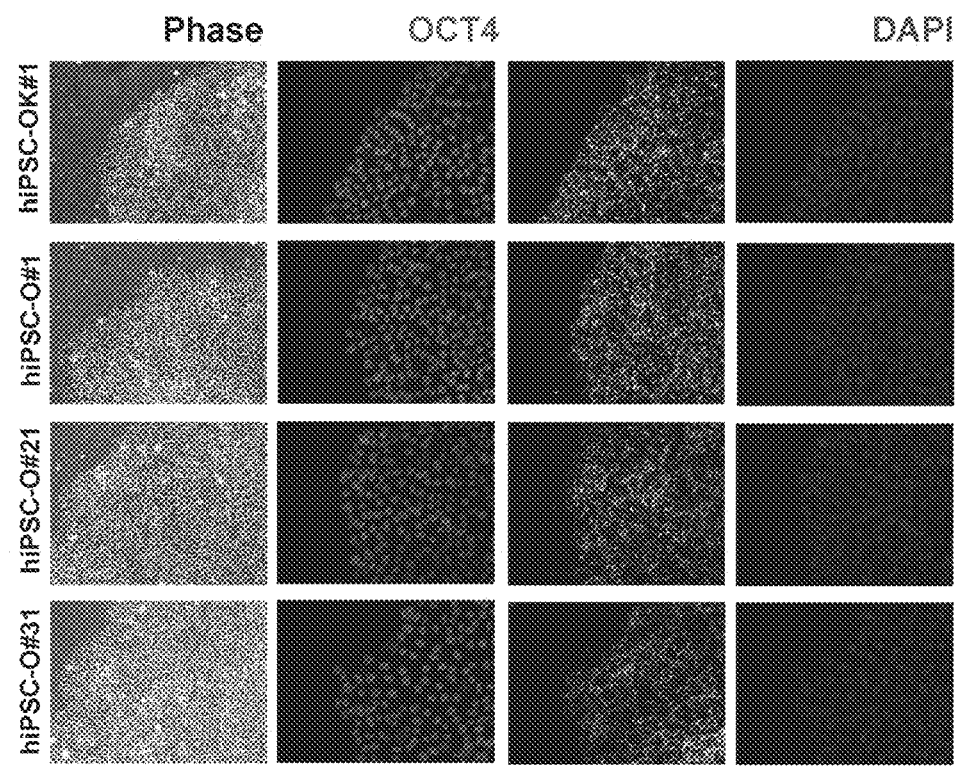
FIG. 7. Feeder-free culture of hiPSC cell lines. hiPSCs were split onto Matrigel/ECM-coated plates in chemically defined hESC medium as previously reported. These hiPSCs could be maintained and expanded in a feeder-free environment. ICC showed the expression of pluripiotency markers, OCT4 and SSEA4. Nuclei were stained with DAPI.
Figure 8:
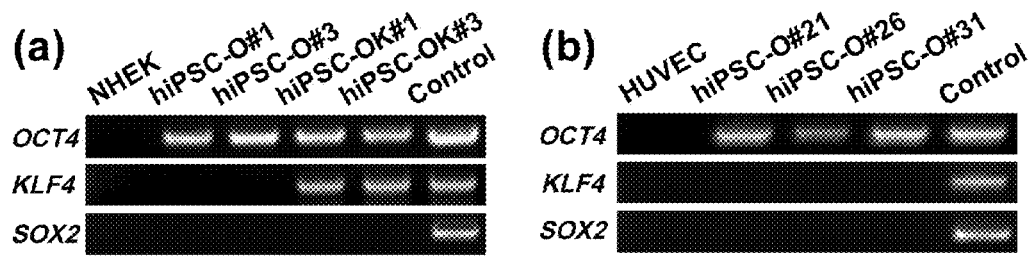
FIG. 8. Genotyping of hiPSCs. RT-PCR analysis using genomic DNA shows that only OCT4 transgene integrated in the genome of hiPSC-O lines (hiPSC-O#1, hiPSC-O#3, hiPSC-O#21, hiPSC-O#26 and hiPSC-O#31). NHEKs (a)

These stably expanded hiPSC-OK and hiPSC-O cells are morphologically indistinguishable from hESCs, and could be cultured on ECM-coated surface under feeder-free and chemically defined conditions (FIG. 1e and FIG. 6). They stained positive for alkaline phosphatase (ALP) and expressed typical pluripotency markers, including OCT4, SOX2, NANOG, TRA-1-81 and SSEA4, detected by immunocytochemistry/ICC (FIG. 1e, 3b, FIGS. 4-5). In addition, RT-PCR analysis confirmed the expression of the endogenous human OCT4, SOX2, NANOG, REX1, UTF1, TDGF2, FGF4 genes, and silencing of exogenous OCT4 and KLF4 (FIGS. 2a and 3c). Furthermore, bisulfite sequencing analysis revealed that the OCT4 and NANOG promoters of hiPSC-OK and hiPSC-O cells are largely demethylated (FIGS. 2b and 3d). This result provides further evidence for reactivation of the pluripotency transcription program in the hiPSC-OK and hiPSC-O cells. Global gene expression analysis of hiPSC-O cells, NHEKs and hESCs showed that hiPSC-O cells are distinct from NHEKs (Pearson correlation value: 0.87) and most similar to hESCs (Pearson correlation value: 0.98) (FIG. 2c). Genotyping analysis showed that hiPSC-O cells only contained the OCT4 transgene without the contamination of transgene KLF4 or SOX2 (FIG. 8). Southern blot analysis showed that there were multiple different integration sites of the OCT4 transgene (FIG. 9) among different clones. In addition, karyotyping result demonstrated that hiPSC-O maintained normal karyotype during the whole reprogramming and expansion process (FIG. 10). Furthermore, DNA fingerprinting test excluded the possibility that these hiPSCs arose from hESC contamination in the laboratory (Table 5).

To examine the developmental potential of these hiPSC-O cells, they were differentiated in vitro by the standard embryoid body (EB) differentiation method. ICC analyses demonstrated that they could effectively differentiate into βIII-tubulin$^+$ characteristic neuronal cells (ectoderm), SMA$^+$ mesodermal cells, and AFP$^+$ endodermal cells (FIGS. 2d and 3e). Quantitative PCR analyses further confirmed the expression of these and additional lineage specific marker genes, including ectodermal cells (βIII-tubulin and NESTIN), mesodermal cells (MSX1 and MLC2a), and endodermal cells (FOXA2 and AFP) (FIG. 2e). Following EB protocol, these hiPSC-OK and hiPSC-O cells could also give rise to rhythmically beating cardiomyocytes. To test their in vivo pluripotency, they were transplanted into SCID mice. Four to six weeks later, these hiPSC-O cells effectively generated typical teratomas containing derivatives of all three germ layers (FIGS. 2f and 3f). Collectively, these in vitro and in vivo characterizations demonstrated that a single transcription factor, OCT4, combined with a defined small molecule cocktail is sufficient to reprogram several human primary somatic cells to iPSCs that are morphologically, molecularly and functionally similar to pluripotent hESCs.

Discussion

The studies presented above have a number of important implications: First, although fetal NSCs were shown to be reprogrammed to iPSCs by ectopic expression of OCT4 alone, there has been significant skepticism about whether exogenous OCT4 gene alone would be sufficient to reprogram other more practical human somatic cells that do not endogenously express SOX2 (one of the two master pluripotency genes in reprogramming), are at later developmental stages (e.g., early embryonic/fetal vs. born/adult), and can be obtained without significant harms to the individual. To our knowledge, our study is the first demonstration that iPSCs can be practically derived from readily available primary human somatic cells (e.g., keratinocytes) transduced with a single exogenous reprogramming gene, OCT4. In contrast to neural stem cells from the brain, keratinocytes are more accessible and can be easily obtained from born individuals with less invasive procedures. This further strengthens the strategy of exploiting various practically accessible human somatic cells for iPSC generation with safer approaches and/or better qualities. Thus, this new method and its further development would significantly facilitate production of patient-specific pluripotent stem cells for various applications.

Second, although small molecules and their combinations have been identified to replace only one or two reprogramming TFs, it becomes exponentially challenging to generate iPSCs when more exogenous reprogramming TFs are omitted together. The identification of this new small molecule cocktail, which functionally replaces three master transcription factors all together (i.e., SOX2, KLF4 and MYC) in enabling generation of iPSCs with OCT4 alone, represents another major step toward the ultimate reprogramming with only small molecules, and further proved and solidified the chemical approach to iPSCs.

Third, this demonstrated single gene condition also has a significant implication for protein-induced pluripotent stem cell (piPSC) technology. A practical challenge for piPSC technology is large-scale and reliable production of the four transducible reprogramming proteins, each of which behaves differently in manufacture (e.g., their expression, folding, stability etc.). Clearly, combining this small molecule cocktail with a single transducible protein would significantly simplify the piPSC technology and facilitate its applications.

Fourth, we identified a new small molecule, PS48, with a new target/mechanism in enhancing reprogramming. PS48 is an allosteric small molecule activator of PDK1 (Hindie, V. et al., *Nat Chem Biol* 4:758-764 (2009)). One mechanism by which PS48 enhances reprogramming appears to be facilitating the metabolic reprogramming from mitochondrial oxidation mainly used by adult somatic cells to glycolysis mainly used by ESCs (which is also known as the Warburg effect) (Manning, B. D. and Cantley, *Cell* 129:1261-1274 (2007); Kondoh, H. et al., *Antioxid Redox Signal* 9:293-299 (2007); Heiden, M. G. V. et al., *Science* 324:1029-1033 (2009)). Such differential use of glycolytic metabolism over mitochondrial respiration by pluripotent stem cells would favor pluripotency by promoting proliferation/cell cycle transition with less oxidative stress. For highly proliferating cells, oxidative phosphorylation would not be able to meet the demand of providing macromolecular precursors for cell replication, but also generates significant amount of reactive oxygen species in mitochondria that could induce excessive oxidative damages. On the other hand, glycolytic metabolism could more effectively generate macromolecular precursors, such as glycolytic intermediates for nonessential amino acids and acetyl-CoA for fatty acids, while provide sufficient energies to meet the needs of proliferating cells (Kondoh, H. et al., *Antioxid Redox Signal* 9:293-299 (2007); Heiden, M. G. V. et al., *Science* 324:1029-1033 (2009)). Interestingly, hypoxic condition and its effector HIF-1α activation not only have been closely linked to promoting glycolytic metabolism, but also were shown to enhance both mouse and human reprogramming (Yoshida, Y. et al., *Cell Stem Cell* 5:237-241 (2009)). Mechanistically, growth factor signaling pathways, hypoxic condition/HIF-1α and reprogramming factor Myc appear to regulate complementary aspects of cellular metabolism, including up-regulating glucose transporters and metabolic enzymes of glycolysis, such as GLUT1, HK2 and PFK1 (Gordan, J. D. et al., *Cancer Cell* 12:108-113 (2007); DeBerardinis, R. J. et al., *Cell Metabolism* 7:11-20 (2008)). Those studies suggest that one potential conserved mechanism of Myc, hypoxic condition/HIF-1α, and growth factors/Akt pathway activation in enhancing reprogramming converge on their essential roles in regulating glycolytic metalolism. Supporting this notion, we found that treatment with PS48 activated down-stream Akt/PKB (FIG. 11a), and up-regulated expression of several key glycolytic genes (FIG. 11d), facilitating the metabolic switch to glycolysis (FIG. 11c). Conversely, we found that inactivation of PDK1 activity by UCN-01 (a PDK1 inhibitor) or inhibition of glycolysis by 2-Deoxy-D-glucose (a glycolysis inhibitor) not only attenuated glycolysis (FIG. 11c) but also blocked reprogramming process (FIG. 11b). Furthermore, several known small molecules that have been widely used to modulate mitochondrial respiration (2,4-dinitrophenol), glycolytic metabolism (Fructose 2,6-bisphosphate and oxalate), or more specifically HIF pathway activation (N-oxaloylglycine and Quercetin) also showed corresponding consistent effects on reprogramming: i.e., compounds facilitating glycolytic metabolism enhance reprogramming (such as 2,4-dinitrophenol and N-oxaloylglycine), while compounds blocking glycolytic metabolism inhibit reprogramming (such as oxalate) (FIG. 11e) (Hewitson, K. S, and Schofield, C. J., *Drug Discov Today* 9:704-711 (2004); Pelicano, H. et al., *Oncogene* 25:4633-4646 (2006)). In conclusion, these results indicated that a metabolic switch to anaerobic glycolysis is critical for and facilitate reprogramming of somatic cells to pluripotent stem cells.

Finally, this new and powerful small molecule cocktail for reprogramming validated the step-wise chemical optimization and screening strategy presented here as a productive approach toward the ultimate purely chemical-induced pluripotent stem cells. Moreover, we found that different small molecules modulating the same target/mechanism could have significantly different effects on reprogramming in a different context, exemplified by A-83-01's and NaB's better reprogramming enhancing activities in human keratinocytes, suggests the importance of "individualized" optimization and treatment with different regimens for specific reprogramming context.

Methods

Cell Culture

Normal Human Epidermal Keratinocytes (Lonza) were maintained in Keratinocyte culturing medium (KCM, Lonza). Human Umbilical Vein Endothelial Cells (HUVECs, Millipore) were maintained in EndoGRO-VEGF Complete Medium (HCM, CHEMICON). Human ESCs and hiPSCs were cultured on MEF feeder cells in conventional human ESC culture media (hESCM: DMEM/F12, 15% Knockout serum replacement, 1% Glutamax, 1% Non-essential amino acids, 1% penicillin/streptomycin, 0.1 mM β-mercaptoethanol and 10 ng/ml bFGF). All cell culture products were from Invitrogen/Gibco BRL except where mentioned.

Lentivirus Production

The lentivirus supernatants were produced and harvested as previously described (Yu, J. et al., *Science* 318:1917-1920 (2007)). The plasmids used for lentivirus production include pSin-EF2-Puro-hOCT4, pSin2-EF2-Puro-hSOX2, pLove-mKlf4, pLove-mMyc, the packaging plasmid psPAX2 and the envelop-coding plasmid pMD2.G (Yu, J. et al., *Science* 318:1917-1920 (2007) and Li, W. et al., *Stem Cells* 27:2992-3000 (2009)).

Reprogramming of NHEKs

NHEKs were cultured in a 100 mm tissue culture dish and transduced 3 times (3-4 hours each transduction) with freshly produced lentivirus supernatants. 1,000,000 transduced NHEKs were seeded on the irradiated x-ray inactivated CF1 MEF feeder cells in a 100-mm dish and cultured in KCM and treated with 5 µM PS48, 0.25 mM NaB (Stemgent) and 0.5 µM A-83-01 (Stemgent) for 2 weeks, followed by changing half volume of media to hESCM and supplementing with 5 µM PS48, 0.25 mM NaB and 0.5 µM A-83-01 for another 2 weeks. Then cell culture media were changed to hESCM and supplemented with 5 µM PS48, 0.25 mM NaB, 0.5 µM A-83-01 and 0.5 µM PD0325901 (Stemgent) for an additional four weeks. The same OCT4 infected keratinocytes cultured in media without chemicals were used as a control. The culture was split by Accutase (Millipore) and treated with 1 µM Thiazovivin (Stemgent) in the first day after splitting. The iPSC colonies stained positive by Alexa Fluor 555 Mouse anti-Human TRA-1-81 antibody (BD Pharmingen) were picked up for expansion on feeder cells in hESCM and cultured routinely.

Reprogramming of HUVECs

HUVECs were cultured in a 100 mm tissue culture dish and transduced 2 times (4-6 hours each transduction) with freshly produced lentivirus supernatants. 200,000 transduced HUVECs were seeded on gelatin coated 100-mm dish, cultured in HCM, and treated with 5 µM PS48, 0.25 mM NaB and 0.5 µM A-83-01 for 2 weeks, followed by changing half volume of media to hESCM and supplementing with 5 µM PS48, 0.25 mM NaB and 0.5 µM A-83-01 for another 2 weeks. Then cell culture media were changed to hESCM and supplemented with 5 µM PS48, 0.25 mM NaB, 0.5 µM A-83-01 and 0.5 µM PD0325901 for additional 1-2 weeks. The iPSC colonies stained positive by Alexa Fluor 555 Mouse anti-Human TRA-1-81 antibody were picked up for expansion on feeder cells in hESCM and cultured routinely. The culture was split by Accutase and treated with 1 µM Thiazovivin in the first day after splitting.

Reprogramming of HUVECs Using Various Metabolism Modulating Compounds

HUVECs were cultured in a 100-mm tissue culture dish and transduced 2 times (4-6 hours each transduction) with freshly produced lentivirus supernatants containing four reprogramming factors (Klf, Sox, Myc, and Oct). About 20,000 transduced HUVECs were seeded on gelatin coated 6-well plate, cultured in HCM, and treated with a metabolism modulating compound for 2 weeks. Then cell culture media were changed to hESCM and supplemented with a metabolism modulating compound for additional 1-2 weeks. The number of iPSC colonies stained positive by Alexa Fluor 555 Mouse anti-Human TRA-1-81 antibody was counted. Various metabolism modulating compounds have been tested, including 10 mM Fructose 2,6-bisphosphate (F2,6P), 10 mM Fructose 6-phosphate (F6P), 10 µM 6-aminonicotinamide (6-AN), 10 µM oxalate (OA), 1 µM 2,4-dinitrophenol (DNP), 1 µM N-oxaloylglycine (NOG), 1 µM Quercetin (QC), 10 µM 2-Hydroxyglutaric acid (2-HA), or 10 µM nicotinic acid (NA).

In Vitro Differentiation

The in vitro differentiation of hiPSCs was carried out by the standard embryoid body (EB) method. Briefly, the hiPSCs were dissociated by Accutase (Millipore), cultured in ultra-low attachment 6-well plate for eight days and then transferred to Matrigel-coated E-well plate in differentiation medium. The cells were fixed for immunocytochemical analysis or harvested for RT-PCR tests eight days later. Differentiation medium: DMEM/F12, 10% FBS, 1% Glutamax, 1% Non-essential amino acids, 1% penicillin/streptomycin, 0.1 mM β-mercaptoethanol.

Alkaline Phosphatase Staining and Immunocytochemistry Assay

Alkaline Phosphatase staining was performed according to the manufacturer's protocol using the Alkaline Phosphatase Detection Kit (Stemgent). Standard immunocytochemistry assay was carried out as previously reported (Li, W. et al., *Stem Cells* 27:2992-3000 (2009)). Primary antibodies used can be found in the Table 2. Secondary antibodies were Alexa Fluor 488 donkey anti-mouse or anti-rabbit IgG (1:1000) (Invitrogen). Nuclei were visualized by DAPI (Sigma-Aldrich) staining. Images were captured using a Nikon Eclipse TE2000-U microscope.

Gene Expression Analysis by RT-PCR and qRT-PCR

For RT-PCR and qRT-PCR analysis, total RNA was extracted from human iPSCs using the RNeasy Plus Mini Kit in combination with QIAshredder (Qiagen). First strand reverse transcription was performed with 2 µg RNA using iScript™ cDNA Synthesis Kit (BioRad). The expression of pluripotency markers was analyzed by RT-PCR using Platinum PCR SuperMix (Invitrogen). The expression of lineage specific markers after differentiation was analyzed by qRT-PCR using iQ SYBR Green Supermix (Bio-Rad). The primers can be found in the Table 1.

Microarray Analysis

The Human Ref-8_v3 expression Beadchip (Illumina, Calif., USA) was used for microarray hybridizations to examine the global gene expression of NHEKs, hiPSC and hES cells. Biotin-16-UTP-labeled cRNA was synthesized from 500 ng total RNA with the Illumina TotalPrep RNA amplification kit (Ambion AMIL1791, Foster City, Calif., USA). The hybridization mix containing 750 ng of labeled amplified cRNA was prepared according to the Illumina BeadStation 500× System Manual (Illumina, San Diego, Calif., USA) using the supplied reagents and GE Healthcare Streptavidin-Cy3 staining solution. Hybridization to the Illumina Human Ref-8_v3 expression Beadchip was for 18 h at 55° C. on a BeadChip Hyb Wheel. The array was scanned using the Illumina BeadArray Reader. All samples were prepared in two biological replicates. Processing and analysis of the microarray data were performed with the Illumina BeadStudio software. The data were subtracted for background and normalized using the rank invariant option.

Bisulfite Genomic Sequencing

Genomic DNAs were isolated using the Non Organic DNA. Isolation Kit (Millipore) and then treated with the EZ DNA Methylation-Gold Kit (Zymo Research Corp., Orange, Calif.). The treated DNAs were then used as templates to amplify sequences of interest. Primers used for OCT4 and NANOG promoter fragment amplification are indicated in Table 1. The resulting fragments were cloned using the TOPO TA Cloning Kit for sequencing (Invitrogen) and sequenced.

Genotyping of hiPSCs

Genotyping of hiPSC lines was performed using RT-PCR of genomic DNA with specific primers (Table 1; Yu, J. et al., *Science* 318:1917-1920 (2007) and Li, W. et al., *Stem Cells* 27:2992-3000 (2009)).

Teratoma Formation

The hiPSC lines were harvested by using 0.05% Trypsin-EDTA. Five million cells were injected under the kidney capsule of SCID mice (n=3). After 4-6 weeks, well developed teratomas were harvested, fixed and then histologically analyzed at TSRI histology core facility.

TABLE 1

Primers used

| Gene | Forward (SEQ ID NO:) | Reverse (SEQ ID NO:) |
|---|---|---|
| For RT-PCR | | |
| Endo-OCT4 | AGTTTGTGCCAGGGTTTT TG (12) | ACTTCACCTTCCCTCCAACC (13) |
| Endo-SOX2 | CAAAAATGGCCATGCAGG TT (14) | AGTTGGGATCGAACAAAAGCTA TT (15) |
| Endo-NANOG | TTTGGAAGCTGCTGGGGA AG (16) | GATGGGAGGAGGGGAGAGGA (17) |
| Endo-KLF4 | ACGATCGTGGCCCCGGAA AAGGACC (18) | GATTGTAGTGCTTTCTGGCTGG GCTCC (19) |
| Endo-cMYC | GCGTCCTGGGAAGGGAGA TCCGGAGC (20) | TTGAGGGGCATCGTCGCGGGAG GCTG (21) |
| REX1 | CAGATCCTAAACAGCTCG CAGAAT (22) | GCGTACGCAAATTAAAGTCCAG A (23) |
| UTF1 | CCGTCGCTGAACACCGCC CTGCTG (24) | CGCGCTGCCCAGAATGAAGCCC AC (25) |
| TDGF2 | CTGCTGCCTGAATGGGGG AACCTGC (26) | GCCACGAGGTGCTCATCCATCA CAAGG (27) |
| FGF4 | CTACAACGCCTACGAGTC CTACA (28) | GTTGCACCAGAAAAGTCAGAGT TG (29) |
| Exo-OCT4 | TGTCTCCGTCACCACTCT GG (30) | ATGCATGCGGATCCTTCG (31) |
| PAX6 | TGTCCAACGGATGTGAG T (32) | TTTCCCAAGCAAAGATGGAC (33) |
| βIII TUBULIN | CAACAGCACGGCCATCCA GG (34) | CTTGGGGCCCTGGGCCTCCGA (35) |
| FOXF1 | AAAGGAGCCACGAAGCAA GC (36) | AGGCTGAAGCGAAGGAAGAGG (37) |
| HAND1 | TCCCTTTTCCGCTTGCTC TC (38) | CATCGCCTACCTGATGGACG (39) |
| AFP | AGCAGCTTGGTGGTGGAT GA (40) | CCTGAGCTTGGCACAGATCCT (41) |
| GATA6 | TGTGCGTTCATGGAGAAG ATCA (42) | TTTGATAAGAGACCTCATGAAC CGACT (43) |
| GAPDH | GTGGACCTGACCTGCCGT CT (44) | GGAGGAGTGGGTGTCGCTGT (45) |
| For bisulfite-sequencing | | |
| OCT4-1 | TTAGGAAAATGGGTAGTA GGGATTT (46) | TACCCAAAAACAAATAAATTA TAAAACCT (47) |
| OCT4-2 | GGATGTTATTAAGATGAA GATAGTTGG (48) | CCTAAACTCCCCTTCAAAATCT ATT (49) |
| NANOG | GAGTTAAAGAGTTTTGTT TTTAAAAATTAT (50) | TCCCAAATCTAATAATTTATCA TATCTTTC (51) |
| For genotyping | | |
| OCT4-Int | CAGTGCCCGAAACCCACA C (52) | AGAGGAACTGCTTCCTTCACGA CA (53) |
| SOX2-Int | TACCTCTTCCTCCCACTC CA (54) | AGAGGAACTGCTTCCTTCACGA CA (55) |
| KLF4-Int | CACCTTGCCTTACACATG AAGAGG (56) | CGTAGAATCGAGACCGAGGAGA (57) |

TABLE 2

Primary antibodies applied

| Antibody | Species | Dilution | Vendor |
|---|---|---|---|
| Anti-OCT4 (1) | Mouse | 1:500 | Santa Cruz Biotechnology |
| Anti-OCT4 (2) | Rabbit | 1:500 | Stemgent |
| Anti-SOX2 | Rabbit | 1:1000 | Chemicon |
| Anti-NANOG | Rabbit | 1:500 | Abcam |
| Anti-SSEA4 | Mouse | 1:500 | Stemgent |
| Anti-TRA-1-81 | Mouse | 1:500 | Stemgent |
| TUJ1 (Anti-βIII TUBULIN) | Mouse | 1:3000 | Covance Research Products |
| Anti-SMA | Mouse | 1:500 | Sigma |
| Anti-AFP | Mouse | 1:500 | Sigma |

TABLE 3

Summary of reprogramming experiments

| Donor Cells | Induction factors | Chemicals | Experiments | TRA-1-81 positive colonies |
|---|---|---|---|---|
| NHEKs (lot number: 0000087940) | OCT4 + KLF4 + SOX2 + MYC | DMSO | #1 | 17 |
| | | | #2 | 20 |
| | | | #3 | 23 |
| | | A83 + PD | #1 | 72 |
| | | | #2 | 104 |
| | | | #3 | 91 |
| | OCT4 + KLF4 + SOX2 | DMSO | #1 | 2 |
| | | | #2 | 3 |
| | | | #3 | 8 |
| | | A83 + PD | #1 | 26 |
| | | | #2 | 35 |
| | | | #3 | 44 |
| | OCT4 + KLF4 | A83 + PD | #1 | 1 |
| | | | #2 | 2 |
| | | | #3 | 0 |
| | | A83 + PS48 + PD | #1 | 15 |
| | | | #2 | 18 |
| | | | #3 | 5 |
| | | A83 + VPA + PD | #1 | 6 |
| | | | #2 | 0 |
| | | | #3 | 3 |
| | | A83 + NaB + PD | #1 | 20 |
| | | | #2 | 17 |
| | | | #3 | 18 |
| | | A83 + PS48 + NaB + PD | #1 | 21 |
| | | | #2 | 30 |
| | | | #3 | 27 |
| | OCT4 | A83 + PS48 + NaB + PD | #1 | 4 |
| | | | #2 | 0 |
| | | | #3 | 3 |
| NHEKs (lot number: 2F0661) | OCT4 | A83 + PS48 + NaB + PD | #1 | 2 |
| | | | #2 | 3 |
| | | | #3 | 0 |
| AHEKs | OCT4 | A83 + PS48 + NaB + PD + Par + CHIR | #1 | 3 |
| | | | #2 | 2 |
| HUVECs | OCT4 | A83 + PS48 + NaB + PD | #1 | 4 |
| | | | #2 | 7 |
| | | | #3 | 4 |
| HUVECs | OCT4 | A83 + PS48 + NaB + PD + Par + CHIR | #1 | 23 |
| | | | #2 | 17 |
| AFDCs | OCT4 | A83 + PS48 + NaB + PD + Par + CHIR | #1 | 5 |
| | | | #2 | 11 |

NHEKs, Neonatal Human Epidermal Keratinocytes; HUVECs, Human Umbilical Vein Endothelial Cells; AHEKs, Adult Human Epidermal Keratinocytes; AFDCs, Amniotic Fluid Derived Cells. Chemical concentration used: PD, 0.5 μM PD0325901; A83, 0.5 μM A-83-01; PS48, 5 μM PS48; VPA, 0.5 mM Valproic acid; NaB, 0.25 mM Sodium butyrate; Par, 2 μM Parnate; CHIR, 3 μM CHIR99021. For four-factor or three-factor induced reprogramming, NHEKs were seeded at a density of 100,000 transduced cells per 10 cm dish and positive colonies were counted four weeks later;

For two-factor induced reprogramming, NHEKs were seeded at a density of 100,000 transduced cells per 10 cm dish and positive colonies were counted six weeks later; and for one-factor induced reprogramming, NHEKs and AHEKs were seeded at a density of 1,000,000 transduced cells per 10 cm dish and positive colonies were counted eight weeks later. HUVECs and AFDCs were seeded at a density of 200,000 transduced cells per 10 cm dish and positive colonies were counted six weeks later.

TABLE 4

Characterization of established human iPSC cell lines

| hiPSC clone | Induction factors | Cell source | Marker expression | RT-PCR test | EB differentiation | Teratoma test |
|---|---|---|---|---|---|---|
| hiPSC-OK#1 | OCT4 + KLF4 | NHEKs | ✓ | ✓ | ✓ | ✓ |
| hiPSC-OK#3 | | | ✓ | ✓ | ✓ | |
| hiPSC-O#1 | OCT4 | NHEKs | ✓ | ✓ | ✓ | ✓ |
| hiPSC-O#3 | | | ✓ | ✓ | ✓ | |
| hiPSC-O#4 | | | ✓ | | | |
| hiPSC-O#5 | | | ✓ | | | |
| 2 more lines | | | | | | |
| hiPSC-O#21 | OCT4 | HUVECs | ✓ | ✓ | ✓ | ✓ |
| hiPSC-O#22 | | | ✓ | | | |
| hiPSC-O#26 | | | ✓ | ✓ | ✓ | |
| hiPSC-O#31 | | | ✓ | ✓ | ✓ | ✓ |
| 7 more lines | | | | | | |
| hiPSC-O#52 | OCT4 | AHEKs | ✓ | | ✓ | |
| hiPSC-O#57 | | | ✓ | | | |
| hiPSC-O#63 | OCT4 | AFDCs | ✓ | | ✓ | |
| hiPSC-O#65 | | | ✓ | | | |

Those cell lines characterized were long-term expanded for over 20 passages under conventional hESC culture condition and further characterized for marker expression and pluripotency; while other cell lines established were stored at passage 5 or 6. Blank entries indicate "not determined."

TABLE 5

DNA fingerprint analysis on Oct4-induced iPSCs and parental cell lines

| Genomic loci | NHEK (pooled) | hiPSC-O#1 | HUVEC | hiPSC-O#21 |
|---|---|---|---|---|
| Amelogenin | X, Y | X, Y | X | X |
| vWA | 11, 15, 17, 18, 19 | 15, 18 | 15; 16 | 15; 16 |
| D8S1179 | 10, 13, 16 | 13, | 10; 13 | 10; 13 |
| TPOX | 8, 9, 11, 12 | 8 | 8 | 8 |
| FGA | 19, 22, 23, 24 | 19, 22 | 24; 27 | 24; 27 |
| D3S1358 | 13, 14, 15, 17 | 17 | 14; 16 | 14; 16 |
| THO1 | 6, 7, 9, 9.3 | 7, 9 | 6 | 6 |
| D21S11 | 24.2, 29, 30.2, 35 | 24.2, 29 | 28; 30.2 | 28; 30.2 |
| D18S51 | 13, 14, 16, 17, 18, 19 | 13, 17 | 13; 18 | 13; 18 |
| Penta E | 5, 8, 13, 14, 19 | 13, 19 | 12 | 12 |
| D5S818 | 8, 11, 12, 13 | 11, 13 | 12; 13 | 12; 13 |
| D13S317 | 8, 9, 11, 12, 13 | 9, 12 | 11; 14 | 11; 14 |
| D7S820 | 8, 9, 10, 11 | 9, 10 | 11 | 11 |
| D16S539 | 9, 10, 11, 12, 13 | 9, 13 | 9; 11 | 9; 11 |
| CSF1PO | 10, 11, 12 | 11, 12 | 11; 12 | 11; 12 |
| Penta D | 2.2, 10, 12 | 10 | 12; 13 | 12; 13 |

Fifteen polymorphic short tandem repeat (STR) DNA loci and the sex chromosome marker amelogenin were investigated.

Example 2

Reprogramming of Human Umbilical Vein Endothelial Cells

We tested the effects of the combination of a HDAC inhibitor, a PDK1 activator, a TGFβ receptor inhibitor, and a MEK inhibitor on HUVECs that were lentivirally transduced with Oct4 alone for their effects on reprogramming kinetics and efficiency.

Methods

Human Umbilical Vein Endothelial Cells (HUVECs, Millipore) were maintained in EndoGRO-VEGF Complete Medium (HCM, CHEMICON). HUVECs were cultured in a 100 mm tissue culture dish and transduced 2 times (4-6 hours/time) with freshly produced lentivirus supernatants. Then 200,000 transduced HUVECs were seeded on gelatin coated 100-mm dish and cultured in HCM and treated with PDK1 activator PS48 (5 µM), HDAC inhibitor NaB (0.25 mM), and TGFβ receptor inhibitor A-83-01(0.5 µM) for 2 weeks, followed by changing half volume of media to hESCM and supplementing with PDK1 activator PS48 (5 µM), HDAC inhibitor NaB (0.25 mM), and TGFβ receptor inhibitor A-83-01(0.5 µM) for another 2 weeks. Then cell culture media were changed to hESCM and supplemented with PDK1 activator PS48 (5 µM), HDAC inhibitor NaB (0.25 mM), and TGFβ receptor inhibitor A-83-01(0.5 µM) and MEK inhibitor PD0325901 (0.5 µM) for additional 2 weeks. The iPSC colonies were stained positive by Alexa Fluor 555 Mouse anti-Human TRA-1-81 antibody (BD Pharmingen). hESCM: DMEM/F12, 15% Knockout serum replacement, 1% Glutamax, 1% Non-essential amino acids, 1% penicillin/streptomycin, 0.1 mM β-mercaptoethanol and 10 ng/ml bFGF.

Results

For HUVECs transduced with Oct4 alone, we tested the effects of the combination of a HDAC inhibitor, a PDK1 activator, a TGFβ receptor inhibitor, a MEK inhibitor on reprogramming efficiency. We found that treatment with the combination of 5 µM PS48, 0.25 mM NaB, 0.5 µM A-83-01 and 0.5 µM PD0325901 results in a ~0.0015% reprogramming efficiency.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method of inducing a non-pluripotent mammalian cell into an induced pluripotent stem cell, the method comprising:
   (a) introducing into the non-pluripotent cell a polynucleotide encoding an Oct4 polypeptide; and
   (b) contacting the non-pluripotent cell with a small molecule 3'-phosphoinositide-dependent kinase-1 (PDK1) activator, a TGFβ receptor/ALK5 inhibitor, and a MEK inhibitor, thereby inducing the non-pluripotent mammalian cell into an induced pluripotent stem cell.

2. The method of claim 1, wherein the small molecule PDK1 activator is:
   (a) an allosteric PDK1 activator; or
   (b) (Z)-5-(4-Chlorophenyl)-3-phenylpent-2-enoic acid ("PS48"), (Z)-5-(4-Bromo-2-fluorophenyl)-3-phenylpent-2-enoic acid ("PS08"), 2-(3-(4-Chlorophenyl)-3-oxo-1-phenylpropylthio)acetic acid, (Z)-5-(Napthalen-2-yl)-3-phenylpent-2-enoic acid ("12Z"), or (Z)-5-(1H-Indol-3-yl)-3-phenylpent-2-enoic acid ("13Z").

3. The method of claim 1, further comprising contacting the non-pluripotent cell with a histone deacetylase (HDAC) inhibitor.

4. The method of claim 1, further comprising one or more of:
   (a) introducing into the non-pluripotent cell a polynucleotide encoding a Klf-4 polypeptide;
   (b) introducing into the non-pluripotent cell a polynucleotide encoding a Sox-2 polypeptide; or
   (c) introducing into the non-pluripotent cell a polynucleotide encoding a c-Myc polypeptide.

5. The method of claim 1, wherein the non-pluripotent cell is a human cell.

6. The method of claim 1, wherein contacting comprises:
   (a) contacting the non-pluripotent cell with a small molecule PDK1 activator in the absence of a MEK inhibitor, followed by contacting the non-pluripotent cell with a small molecule PDK1 activator and a MEK inhibitor; or
   (b) contacting the non-pluripotent cell with a small molecule PDK1 activator, a TGFβ receptor/ALK5 inhibitor, and a histone deacetylase (HDAC) inhibitor in the absence of a MEK inhibitor, followed by contacting the non-pluripotent cell with a small molecule PDK1 activator, a TGFβ receptor/ALK5 inhibitor, a histone deacetylase (HDAC) inhibitor and a MEK inhibitor.

7. A mixture comprising: isolated mammalian cells, a small molecule PDK1 activator, and:
   (a) a TGFβ receptor/ALK5 inhibitor;
   (b) a MEK inhibitor; and
   (c) one or more vectors comprising a polynucleotide encoding one or more exogenous transcription factors selected from the group consisting of an Oct-4 polypeptide, a Klf-4 polypeptide, a c-myc polypeptide, and a Sox-2 polypeptide.

8. The mixture of claim 7, wherein at least 99% of the cells are non-pluripotent cells.

9. The mixture of claim 7, wherein the cells are human cells.

10. The mixture of claim 7, wherein the small molecule PDK1 activator is:
    (a) an allosteric PDK1 activator; or
    (b) (Z)-5-(4-Chlorophenyl)-3-phenylpent-2-enoic acid ("PS48"), (Z)-5-(4-Bromo-2-fluorophenyl)-3-phenylpent-2-enoic acid ("PS08"), 2-(3-(4-Chlorophenyl)-3-oxo-1-phenylpropylthio)acetic acid, (Z)-5-(Napthalen-2-yl)-3-phenylpent-2-enoic acid ("12Z"), or (Z)-5-(1H-Indol-3-yl)-3-phenylpent-2-enoic acid ("13Z").

11. The mixture of claim 7, further comprising a histone deacetylase (HDAC) inhibitor.

* * * * *

SEQUENCE LISTING

<160> NUMBER OF SEQ ID NOS: 57

<210> SEQ ID NO 1
<211> LENGTH: 25
<212> TYPE: PRT
<213> ORGANISM: Artificial Sequence
<220> FEATURE:
<223> OTHER INFORMATION: synthetic delivery enhancing transporter
      peptide sequence of 5-25 contiguous arginines
<220> FEATURE:
<221> NAME/KEY: VARIANT
<222> LOCATION: (6)...(25)
<223> OTHER INFORMATION: Arg may be present or absent

<400> SEQUENCE: 1

Arg Arg Arg Arg Arg Arg Arg Arg Arg Arg Arg Arg Arg Arg Arg Arg
 1               5                   10                  15

Arg Arg Arg Arg Arg Arg Arg Arg Arg
            20                  25

<210> SEQ ID NO 2
<211> LENGTH: 61
<212> TYPE: PRT
<213> ORGANISM: Herpes simplex virus
<220> FEATURE:
<223> OTHER INFORMATION: structural protein VP22 polypeptide sequence
      enhancing transport across membranes

<400> SEQUENCE: 2

Gly Ser Pro Pro Thr Ala Pro Thr Arg Ser Lys Thr Pro Ala Gln Gly
 1               5                   10                  15

Leu Ala Arg Lys Leu His Phe Ser Thr Ala Pro Pro Asn Pro Asp Ala
            20                  25                  30

Pro Trp Thr Pro Arg Val Ala Gly Phe Asn Lys Arg Val Phe Arg Phe
        35                  40                  45

Ser Pro Gln Thr Ala Arg Arg Ala Thr Thr Thr Arg Ile
    50                  55                  60

<210> SEQ ID NO 3
<211> LENGTH: 26
<212> TYPE: PRT
<213> ORGANISM: Artificial Sequence
<220> FEATURE:
<223> OTHER INFORMATION: synthetic Kaposi FGF (kFGF) signal polypeptide
      sequence enhancing transport across membranes

<400> SEQUENCE: 3

Ala Gly Ser Gly Gly Ala Ala Val Ala Leu Leu Pro Ala Val Leu Leu
 1               5                   10                  15

Ala Leu Leu Ala Pro Gly Gly Glu Phe Ala
            20                  25

<210> SEQ ID NO 4
<211> LENGTH: 21
<212> TYPE: PRT
<213> ORGANISM: Artificial Sequence
<220> FEATURE:
<223> OTHER INFORMATION: synthetic protein transduction domain-4 (PTD4)
      polypeptide sequence enhancing transport across membranes

<400> SEQUENCE: 4

Ala Gly Ser Gly Gly Tyr Ala Arg Ala Ala Ala Arg Gln Ala Arg Ala
 1               5                   10                  15

Gly Gly Glu Phe Ala
            20

<210> SEQ ID NO 5
<211> LENGTH: 16
<212> TYPE: PRT
<213> ORGANISM: Artificial Sequence

```
<220> FEATURE:
<223> OTHER INFORMATION: synthetic penetratin polypeptide sequence
      enhancing transport across membranes

<400> SEQUENCE: 5

Arg Gln Ile Lys Ile Trp Phe Gln Gly Arg Arg Met Lys Trp Lys Lys
1               5                   10                  15

<210> SEQ ID NO 6
<211> LENGTH: 11
<212> TYPE: PRT
<213> ORGANISM: Human immunodeficiency virus 1
<220> FEATURE:
<223> OTHER INFORMATION: HIV-1 transcriptional activator protein TAT
      polypeptide sequence enhancing transport across membranes

<400> SEQUENCE: 6

Tyr Gly Arg Lys Lys Arg Arg Gln Arg Arg Arg
1               5                   10

<210> SEQ ID NO 7
<211> LENGTH: 22
<212> TYPE: PRT
<213> ORGANISM: Artificial Sequence
<220> FEATURE:
<223> OTHER INFORMATION: synthetic M918 polypeptide sequence enhancing
      transport across membranes

<400> SEQUENCE: 7

Met Val Thr Val Leu Phe Arg Arg Leu Arg Ile Arg Arg Ala Cys Gly
1               5                   10                  15

Pro Pro Arg Val Arg Val
            20

<210> SEQ ID NO 8
<211> LENGTH: 21
<212> TYPE: PRT
<213> ORGANISM: Artificial Sequence
<220> FEATURE:
<223> OTHER INFORMATION: synthetic transportan-10 polypeptide sequence
      enhancing transport across membranes

<400> SEQUENCE: 8

Ala Gly Tyr Leu Leu Gly Lys Ile Gly Leu Lys Ala Leu Ala Ala Leu
1               5                   10                  15

Ala Lys Lys Ile Leu
            20

<210> SEQ ID NO 9
<211> LENGTH: 8
<212> TYPE: PRT
<213> ORGANISM: Artificial Sequence
<220> FEATURE:
<223> OTHER INFORMATION: synthetic 8-arginine peptide sequence enhancing
      transport across membranes

<400> SEQUENCE: 9

Arg Arg Arg Arg Arg Arg Arg Arg
1               5

<210> SEQ ID NO 10
<211> LENGTH: 11
<212> TYPE: PRT
<213> ORGANISM: Artificial Sequence
<220> FEATURE:
<223> OTHER INFORMATION: synthetic 11 contiguous arginine peptide
      sequence enhancing transport across membranes
```

```
<400> SEQUENCE: 10

Arg Arg Arg Arg Arg Arg Arg Arg Arg Arg
 1               5                  10

<210> SEQ ID NO 11
<211> LENGTH: 20
<212> TYPE: PRT
<213> ORGANISM: Artificial Sequence
<220> FEATURE:
<223> OTHER INFORMATION: synthetic peptide sequence comprising 11
      contiguous arginines enhancing transport across membranes

<400> SEQUENCE: 11

Glu Ser Gly Gly Gly Gly Ser Pro Gly Arg Arg Arg Arg Arg Arg
 1               5                  10                  15

Arg Arg Arg Arg
             20

<210> SEQ ID NO 12
<211> LENGTH: 20
<212> TYPE: DNA
<213> ORGANISM: Artificial Sequence
<220> FEATURE:
<223> OTHER INFORMATION: synthetic RT-PCR forward primer Endo-OCT4

<400> SEQUENCE: 12
agtttgtgcc agggttttg                                                  20

<210> SEQ ID NO 13
<211> LENGTH: 20
<212> TYPE: DNA
<213> ORGANISM: Artificial Sequence
<220> FEATURE:
<223> OTHER INFORMATION: synthetic RT-PCR reverse primer Endo-OCT4

<400> SEQUENCE: 13
acttcacctt ccctccaacc                                                 20

<210> SEQ ID NO 14
<211> LENGTH: 20
<212> TYPE: DNA
<213> ORGANISM: Artificial Sequence
<220> FEATURE:
<223> OTHER INFORMATION: synthetic RT-PCR forward primer Endo-SOX2

<400> SEQUENCE: 14
caaaaatggc catgcaggtt                                                 20

<210> SEQ ID NO 15
<211> LENGTH: 24
<212> TYPE: DNA
<213> ORGANISM: Artificial Sequence
<220> FEATURE:
<223> OTHER INFORMATION: synthetic RT-PCR reverse primer Endo-SOX2

<400> SEQUENCE: 15
agttgggatc gaacaaaagc tatt                                            24

<210> SEQ ID NO 16
<211> LENGTH: 20
<212> TYPE: DNA
<213> ORGANISM: Artificial Sequence
<220> FEATURE:
<223> OTHER INFORMATION: synthetic RT-PCR forward primer Endo-NANOG
```

<400> SEQUENCE: 16
tttggaagct gctggggaag                                                        20

<210> SEQ ID NO 17
<211> LENGTH: 20
<212> TYPE: DNA
<213> ORGANISM: Artificial Sequence
<220> FEATURE:
<223> OTHER INFORMATION: synthetic RT-PCR reverse primer Endo-NANOG

<400> SEQUENCE: 17
gatgggagga ggggagagga                                                        20

<210> SEQ ID NO 18
<211> LENGTH: 25
<212> TYPE: DNA
<213> ORGANISM: Artificial Sequence
<220> FEATURE:
<223> OTHER INFORMATION: synthetic RT-PCR forward primer Endo-KLF4

<400> SEQUENCE: 18
acgatcgtgg ccccggaaaa ggacc                                                  25

<210> SEQ ID NO 19
<211> LENGTH: 27
<212> TYPE: DNA
<213> ORGANISM: Artificial Sequence
<220> FEATURE:
<223> OTHER INFORMATION: synthetic RT-PCR reverse primer Endo-KLF4

<400> SEQUENCE: 19
gattgtagtg ctttctggct gggctcc                                                27

<210> SEQ ID NO 20
<211> LENGTH: 26
<212> TYPE: DNA
<213> ORGANISM: Artificial Sequence
<220> FEATURE:
<223> OTHER INFORMATION: synthetic RT-PCR forward primer Endo-cMYC

<400> SEQUENCE: 20
gcgtcctggg aagggagatc cggagc                                                 26

<210> SEQ ID NO 21
<211> LENGTH: 26
<212> TYPE: DNA
<213> ORGANISM: Artificial Sequence
<220> FEATURE:
<223> OTHER INFORMATION: synthetic RT-PCR reverse primer Endo-cMYC

<400> SEQUENCE: 21
ttgaggggca tcgtcgcggg aggctg                                                 26

<210> SEQ ID NO 22
<211> LENGTH: 24
<212> TYPE: DNA
<213> ORGANISM: Artificial Sequence
<220> FEATURE:
<223> OTHER INFORMATION: synthetic RT-PCR forward primer REX1

<400> SEQUENCE: 22
cagatcctaa acagctcgca gaat                                                   24

```
<210> SEQ ID NO 23
<211> LENGTH: 23
<212> TYPE: DNA
<213> ORGANISM: Artificial Sequence
<220> FEATURE:
<223> OTHER INFORMATION: synthetic RT-PCR reverse primer REX1

<400> SEQUENCE: 23
gcgtacgcaa attaaagtcc aga                                          23

<210> SEQ ID NO 24
<211> LENGTH: 24
<212> TYPE: DNA
<213> ORGANISM: Artificial Sequence
<220> FEATURE:
<223> OTHER INFORMATION: synthetic RT-PCR forward primer UTF1

<400> SEQUENCE: 24
ccgtcgctga acaccgccct gctg                                         24

<210> SEQ ID NO 25
<211> LENGTH: 24
<212> TYPE: DNA
<213> ORGANISM: Artificial Sequence
<220> FEATURE:
<223> OTHER INFORMATION: synthetic RT-PCR reverse primer UTF1

<400> SEQUENCE: 25
cgcgctgccc agaatgaagc ccac                                         24

<210> SEQ ID NO 26
<211> LENGTH: 25
<212> TYPE: DNA
<213> ORGANISM: Artificial Sequence
<220> FEATURE:
<223> OTHER INFORMATION: synthetic RT-PCR forward primer TDGF2

<400> SEQUENCE: 26
ctgctgcctg aatgggggaa cctgc                                        25

<210> SEQ ID NO 27
<211> LENGTH: 27
<212> TYPE: DNA
<213> ORGANISM: Artificial Sequence
<220> FEATURE:
<223> OTHER INFORMATION: synthetic RT-PCR reverse primer TDGF2

<400> SEQUENCE: 27
gccacgaggt gctcatccat cacaagg                                      27

<210> SEQ ID NO 28
<211> LENGTH: 23
<212> TYPE: DNA
<213> ORGANISM: Artificial Sequence
<220> FEATURE:
<223> OTHER INFORMATION: synthetic RT-PCR forward primer FGF4

<400> SEQUENCE: 28
ctacaacgcc tacgagtcct aca                                          23

<210> SEQ ID NO 29
<211> LENGTH: 24
<212> TYPE: DNA
<213> ORGANISM: Artificial Sequence
<220> FEATURE:
<223> OTHER INFORMATION: synthetic RT-PCR reverse primer FGF4
```

<400> SEQUENCE: 29
gttgcaccag aaaagtcaga gttg                                    24

<210> SEQ ID NO 30
<211> LENGTH: 20
<212> TYPE: DNA
<213> ORGANISM: Artificial Sequence
<220> FEATURE:
<223> OTHER INFORMATION: synthetic RT-PCR forward primer Exo-OCT4

<400> SEQUENCE: 30
tgtctccgtc accactctgg                                         20

<210> SEQ ID NO 31
<211> LENGTH: 18
<212> TYPE: DNA
<213> ORGANISM: Artificial Sequence
<220> FEATURE:
<223> OTHER INFORMATION: synthetic RT-PCR reverse primer Exo-OCT4

<400> SEQUENCE: 31
atgcatgcgg atccttcg                                           18

<210> SEQ ID NO 32
<211> LENGTH: 18
<212> TYPE: DNA
<213> ORGANISM: Artificial Sequence
<220> FEATURE:
<223> OTHER INFORMATION: synthetic RT-PCR forward primer PAX6

<400> SEQUENCE: 32
tgtccaacgg atgtgagt                                           18

<210> SEQ ID NO 33
<211> LENGTH: 20
<212> TYPE: DNA
<213> ORGANISM: Artificial Sequence
<220> FEATURE:
<223> OTHER INFORMATION: synthetic RT-PCR reverse primer PAX6

<400> SEQUENCE: 33
tttcccaagc aaagatggac                                         20

<210> SEQ ID NO 34
<211> LENGTH: 20
<212> TYPE: DNA
<213> ORGANISM: Artificial Sequence
<220> FEATURE:
<223> OTHER INFORMATION: synthetic RT-PCR forward primer betaIII TUBULIN

<400> SEQUENCE: 34
caacagcacg gccatccagg                                         20

<210> SEQ ID NO 35
<211> LENGTH: 21
<212> TYPE: DNA
<213> ORGANISM: Artificial Sequence
<220> FEATURE:
<223> OTHER INFORMATION: synthetic RT-PCR reverse primer betaIII TUBULIN

<400> SEQUENCE: 35
cttggggccc tgggcctccg a                                       21

```
<210> SEQ ID NO 36
<211> LENGTH: 20
<212> TYPE: DNA
<213> ORGANISM: Artificial Sequence
<220> FEATURE:
<223> OTHER INFORMATION: synthetic RT-PCR forward primer FOXF1

<400> SEQUENCE: 36
aaaggagcca cgaagcaagc                                                   20

<210> SEQ ID NO 37
<211> LENGTH: 21
<212> TYPE: DNA
<213> ORGANISM: Artificial Sequence
<220> FEATURE:
<223> OTHER INFORMATION: synthetic RT-PCR reverse primer FOXF1

<400> SEQUENCE: 37
aggctgaagc gaaggaagag g                                                 21

<210> SEQ ID NO 38
<211> LENGTH: 20
<212> TYPE: DNA
<213> ORGANISM: Artificial Sequence
<220> FEATURE:
<223> OTHER INFORMATION: synthetic RT-PCR forward primer HAND1

<400> SEQUENCE: 38 tccctttcc gcttgctctc                                                    20

<210> SEQ ID NO 39
<211> LENGTH: 20
<212> TYPE: DNA
<213> ORGANISM: Artificial Sequence
<220> FEATURE:
<223> OTHER INFORMATION: synthetic RT-PCR reverse primer HAND1

<400> SEQUENCE: 39
catcgcctac ctgatggacg                                                   20

<210> SEQ ID NO 40
<211> LENGTH: 20
<212> TYPE: DNA
<213> ORGANISM: Artificial Sequence
<220> FEATURE:
<223> OTHER INFORMATION: synthetic RT-PCR forward primer AFP

<400> SEQUENCE: 40
agcagcttgg tggtggatga                                                   20

<210> SEQ ID NO 41
<211> LENGTH: 21
<212> TYPE: DNA
<213> ORGANISM: Artificial Sequence
<220> FEATURE:
<223> OTHER INFORMATION: synthetic RT-PCR reverse primer AFP

<400> SEQUENCE: 41
cctgagcttg gcacagatcc t                                                 21

<210> SEQ ID NO 42
<211> LENGTH: 22
<212> TYPE: DNA
<213> ORGANISM: Artificial Sequence
<220> FEATURE:
<223> OTHER INFORMATION: synthetic RT-PCR forward primer GATA6
```

```
<400> SEQUENCE: 42
tgtgcgttca tggagaagat ca                                              22

<210> SEQ ID NO 43
<211> LENGTH: 27
<212> TYPE: DNA
<213> ORGANISM: Artificial Sequence
<220> FEATURE:
<223> OTHER INFORMATION: synthetic RT-PCR reverse primer GATA6

<400> SEQUENCE: 43
tttgataaga gacctcatga accgact                                         27

<210> SEQ ID NO 44
<211> LENGTH: 20
<212> TYPE: DNA
<213> ORGANISM: Artificial Sequence
<220> FEATURE:
<223> OTHER INFORMATION: synthetic RT-PCR forward primer GAPDH

<400> SEQUENCE: 44
gtggacctga cctgccgtct                                                 20

<210> SEQ ID NO 45
<211> LENGTH: 20
<212> TYPE: DNA
<213> ORGANISM: Artificial Sequence
<220> FEATURE:
<223> OTHER INFORMATION: synthetic RT-PCR reverse primer GAPDH

<400> SEQUENCE: 45
ggaggagtgg gtgtcgctgt                                                 20

<210> SEQ ID NO 46
<211> LENGTH: 25
<212> TYPE: DNA
<213> ORGANISM: Artificial Sequence
<220> FEATURE:
<223> OTHER INFORMATION: synthetic bisulfite-sequencing forward primer
      OCT4-1

<400> SEQUENCE: 46
ttaggaaaat gggtagtagg gattt                                           25

<210> SEQ ID NO 47
<211> LENGTH: 30
<212> TYPE: DNA
<213> ORGANISM: Artificial Sequence
<220> FEATURE:
<223> OTHER INFORMATION: synthetic bisulfite-sequencing reverse primer
      OCT4-1

<400> SEQUENCE: 47
tacccaaaaa acaaataaat tataaaacct                                      30

<210> SEQ ID NO 48
<211> LENGTH: 27
<212> TYPE: DNA
<213> ORGANISM: Artificial Sequence
<220> FEATURE:
<223> OTHER INFORMATION: synthetic bisulfite-sequencing forward primer
      OCT4-2

<400> SEQUENCE: 48
ggatgttatt aagatgaaga tagttgg                                         27
```

```
<210> SEQ ID NO 49
<211> LENGTH: 25
<212> TYPE: DNA
<213> ORGANISM: Artificial Sequence
<220> FEATURE:
<223> OTHER INFORMATION: synthetic bisulfite-sequencing reverse primer
      OCT4-2

<400> SEQUENCE: 49
cctaaactcc ccttcaaaat ctatt                                          25

<210> SEQ ID NO 50
<211> LENGTH: 30
<212> TYPE: DNA
<213> ORGANISM: Artificial Sequence
<220> FEATURE:
<223> OTHER INFORMATION: synthetic bisulfite-sequencing forward primer
      NANOG

<400> SEQUENCE: 50
gagttaaaga gttttgtttt taaaaattat                                     30

<210> SEQ ID NO 51
<211> LENGTH: 30
<212> TYPE: DNA
<213> ORGANISM: Artificial Sequence
<220> FEATURE:
<223> OTHER INFORMATION: synthetic bisulfite-sequencing reverse primer
      NANOG

<400> SEQUENCE: 51
tcccaaatct aataatttat catatctttc                                     30

<210> SEQ ID NO 52
<211> LENGTH: 19
<212> TYPE: DNA
<213> ORGANISM: Artificial Sequence
<220> FEATURE:
<223> OTHER INFORMATION: synthetic genotyping forward primer OCT4-Int

<400> SEQUENCE: 52
cagtgcccga aacccacac                                                 19

<210> SEQ ID NO 53
<211> LENGTH: 24
<212> TYPE: DNA
<213> ORGANISM: Artificial Sequence
<220> FEATURE:
<223> OTHER INFORMATION: synthetic genotyping reverse primer OCT4-Int

<400> SEQUENCE: 53
agaggaactg cttccttcac gaca                                           24

<210> SEQ ID NO 54
<211> LENGTH: 20
<212> TYPE: DNA
<213> ORGANISM: Artificial Sequence
<220> FEATURE:
<223> OTHER INFORMATION: synthetic genotyping forward primer SOX2-Int

<400> SEQUENCE: 54
tacctcttcc tcccactcca                                                20

<210> SEQ ID NO 55
<211> LENGTH: 24
<212> TYPE: DNA
<213> ORGANISM: Artificial Sequence
```

```
<220> FEATURE:
<223> OTHER INFORMATION: synthetic genotyping reverse primer SOX2-Int

<400> SEQUENCE: 55
agaggaactg cttccttcac gaca                                          24

<210> SEQ ID NO 56
<211> LENGTH: 24
<212> TYPE: DNA
<213> ORGANISM: Artificial Sequence
<220> FEATURE:
<223> OTHER INFORMATION: synthetic genotyping forward primer KLF4-Int

<400> SEQUENCE: 56
caccttgcct tacacatgaa gagg                                          24

<210> SEQ ID NO 57
<211> LENGTH: 22
<212> TYPE: DNA
<213> ORGANISM: Artificial Sequence
<220> FEATURE:
<223> OTHER INFORMATION: synthetic genotyping reverse primer KLF4-Int

<400> SEQUENCE: 57
cgtagaatcg agaccgagga ga                                            22
```